US009725462B2

(12) United States Patent
Burgdorf et al.

(10) Patent No.: US 9,725,462 B2
(45) Date of Patent: Aug. 8, 2017

(54) PYRIDOPYRIMIDINE DERIVATIVES AS PROTEIN KINASE INHIBITORS

(71) Applicant: Merck Patent GmbH, Darmstadt (DE)

(72) Inventors: Lars Burgdorf, Frankfurt am Main (DE); Daniel Kuhn, Rossdorf (DE); Tatjana Ross, Eschborn (DE); Carl Deutsch, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/420,003

(22) PCT Filed: Jul. 10, 2013

(86) PCT No.: PCT/EP2013/002032
§ 371 (c)(1),
(2) Date: Feb. 6, 2015

(87) PCT Pub. No.: WO2014/023385
PCT Pub. Date: Feb. 13, 2014

(65) Prior Publication Data
US 2015/0218186 A1 Aug. 6, 2015

(30) Foreign Application Priority Data
Aug. 7, 2012 (EP) .................................. 12005716

(51) Int. Cl.
*C07D 471/04* (2006.01)
*A61K 31/519* (2006.01)
*C07D 498/04* (2006.01)
*A61K 31/538* (2006.01)
*A61K 31/5383* (2006.01)
*A61P 35/04* (2006.01)
*A61P 29/00* (2006.01)
*A61P 9/00* (2006.01)
*A61P 25/28* (2006.01)
*A61P 3/00* (2006.01)
*A61P 31/00* (2006.01)
*A61P 37/00* (2006.01)

(52) U.S. Cl.
CPC .......... *C07D 498/04* (2013.01); *A61K 31/519* (2013.01); *A61K 31/538* (2013.01); *A61K 31/5383* (2013.01); *C07D 471/04* (2013.01)

(58) Field of Classification Search
CPC ..... C07D 487/04; C07D 71/04; A61K 31/519
See application file for complete search history.

(56) References Cited

U.S. PATENT DOCUMENTS

| 4,959,368 A * | 9/1990 | Awaya ................. A61K 31/505 514/183 |
| 7,998,978 B2 | 8/2011 | Huang |
| 8,404,677 B2 | 3/2013 | Kim et al. |
| 8,530,650 B2 | 9/2013 | Schiemann |
| 2011/0269739 A1 | 11/2011 | Kim et al. |

FOREIGN PATENT DOCUMENTS

| JP | 2009535393 A | 10/2009 |
| JP | 2012510481 A | 5/2012 |
| WO | 2011/053861 A1 | 5/2011 |

OTHER PUBLICATIONS

International Search Report dated Aug. 27, 2013 issued in corresponding PCT/EP2013/002032 application (pp. 1-4).
Y. Chen et al., "Synthesis of 8-Aryl-Substituted 4-(5-Chloropyrido[4,3-d]pyrimidine-2-yl)Morpholines as Intermediates of Potential PI3K Inhibitors Via Selective Suzuki-Miyaura Cross-Coupling Reaction", Arkivoc, vol. XI, XP055075562 (Aug. 16, 2009) pp. 257-267.
1st Office Action corresponding to JP Application No. 2015-525760—Drafting Date: Apr. 20, 2017—Dispatching Date—May 8, 2017.
Chen, Yanhong et al., "Synthesis of 8-aryl-substituted 4-5(chloropyrido[4,3-d]pyrimidine-2-yl)morpholines as intermediaes of potential PI3K inhibitors via selective Suzuki-Miyaura cross-coupling reaction", ARKAT-USA, Inc. ARKIVOC, 2009, No. xi, pp. 257-267.

* cited by examiner

*Primary Examiner* — Susanna Moore
(74) *Attorney, Agent, or Firm* — Millen White Zelano and Branigan, PC; John Sopp; Anthony Zelano

(57) ABSTRACT

Compounds of the formula I

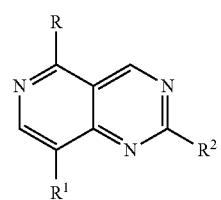

in which R, $R^1$ and $R^2$ have the meanings indicated in claim 1, are inhibitors of Syk, and can be employed, inter alia, for the treatment of cancer, rheumatoid arthritis and/or systemic lupus.

11 Claims, No Drawings

PYRIDOPYRIMIDINE DERIVATIVES AS PROTEIN KINASE INHIBITORS

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the key events in the signaling pathway following the activation of mast cells is activation of the tyrosine kinase Syk. Mast cells play a critical role in asthma and allergic disorders by releasing pro-inflammatory mediators and cytokines. Antigen-mediated aggregation of FcεRJ, the high-affinity receptor for IgE, results in activation of mast cells. This triggers a series of signaling events resulting in the release of mediators, including histamine, proteases, leukotrienes and cytokines. These mediators cause increased vascular permeability, mucus production, bronchoconstriction, tissue degradation and inflammation, thus playing key roles in the etiology and symptoms of asthma and allergic disorders. Syk kinase acts as a central initiator of all subsequent signaling leading to mediator release. The critical role of Syk kinase in the signaling path was demonstrated by the complete inhibition of mediator release by a protein containing the SH2domains of Syk kinase that functioned as an inhibitor of Syk kinase (J. A. Taylor et al, Molec. and Cell Biol, 15: 4149-4157 (1995).

Syk (Spleen-Tyrosine-Kinase) is a 72 kDa non-receptor tyrosine kinase belonging to the subfamily of intracellular tyrosine kinases that comprises ZAP70, Pyk2, Abl, Tie2, KDR and HER, among others. Syk is a major regulator of FcR (FcγRI, II, III, FcεRI, FcαR) and BCR signaling and is expressed throughout hematopoietic lineage, as well as in fibroblasts, osteoclasts, hepatocytes, epithelial and neuronal cells. In addition to the C terminal kinase domain, SYK exhibits two SH2domains and over 10 autophosphorylation sites[1].

By means of both its SH2 domains SYK is specifically recruited to phosphorylated ITAMs (Immunoreceptor Tyrosine-based Activation Motifs present in immunoreceptors such as FcγRI, IIA, IIIA, FcαR, FcεRI and BCR, expressed by monocytes, macrophages, mast cells, neutrophils and B cells) and specifically mediates immunoreceptor signaling triggered by activation of those receptors in mast cells, B cells, macrophages, monocytes, neutrophils, eosinophils, NK cells, DC cells platelets and osteoclasts[1,2].

Upon BCR cross linking, tyrosine residues at the ITAM motifs of the cytosolic tail of the Igα/Igβ are phosphorylated by the Src-family kinase Lyn, generating docking sites for SYK that is thus recruited to the BCR immunocomplex. SYK is then phosphorylated and activated by the Src-family kinase Lyn. Upon activation, SYK will phosphorylate the adaptor protein BLNK allowing its interaction with both BTK and PLCγ$_2$ via their respective SH2 domains. SYK phosphorylated—and thus activated—BTK will in turn phosphorylate and activate PLCγ$_2$ leading to IP$_3$ formation, Ca$^{2+}$ mobilization, PKC and MAPK activation and consequent NFAT, AP-1 and NFκB transcription factor activation, resulting in activation and surface marker expression, cytokine release, survival and proliferation of B cells[3]. In mast cells, allergen activated FcεRI is phosphorylated by LYN and FYN and recruits SYK which is in turn phosphorylated by LYN and further autophosphorylated, becoming fully activated. Activated SYK phosphorylates the two adaptor molecules NTAL and LAT creating more docking sites for SH2 containing proteins such as PLCγ$_1$, vav, and the p85 regulatory subunit of PI3K, resulting in mast cell degranulation and cytokine production[4]. Syk's critical role in signal transduction of mast cells is confirmed by reproducible observation that the 10-15% of basophils (circulating mast cells) from human donors that cannot degranulate have reduced amounts of Syk protein[5,6]. In addition, SYK is required for the bone resorption activity of osteoclasts. Upon stimulation of osteoclasts by αvβ3 integrin, SYK becomes phosphorylated, most likely by c-Src, in a DAP-12/FcγRII dependent mechanism, leading to SPL-76 and Vav3 phosphorylation and subsequent cytoskeletal reorganisation. SYK deficient osteoclasts are inactive and show defective cytoskeletal reorganisation. In correlation with this, SYK deficient embryos show defective skeletal mass[7,8].

BCR-mediated activation of B-cells in the lymph nodes, as well as FcR-mediated activation of dendritic cells, monocytes, macrophages, neutrophils and mast cells in the joints, are essential components of the cellular patho-physiological mechanisms taking place during rheumaoid arthritis (RA). Moreover, activation of osteoclasts leads to the bone and cartilage destruction which are hallmarks of this pathology[9]. SYK signaling should therefore play a pivotal role during the development of arthritis, both at the periphery and on the site of inflammation[10]. Indeed, an orally available Syk inhibitor R406-developed by Rigel-induced a significant improvement of clinical scores and significantly reduced serum cytokine concentrations, as well as bone erosion, in a murine model of RA[11,12]. Moreover, this inhibitor has shown efficacy (ACR scores improvement) and good tolerability in RA Phase II studies in humans[13,14,15].

In SLE B cells contribute essentially towards pathogenesis via production of autoantibodies resulting in immune complex formation, stimulation of Fc receptors and finally in an excessive and chronic activation of inflammation. In a murine model of SLE treatment with a Syk inhibitor resulted in a reduction of numbers of class-switched germinal center, marginal zone, newly formed and follicular B cells and therefore in disease mitigating effects[18].

Although TCR signals are transmitted by the intracellular tyrosine kinase ZAP-70 in thymocytes and naïve T cells, several studies indicate that differentiated effector T cells, such as those involved in the pathophysiology of Multiple sclerosis (MS) or systemic lupus erythematosus (SLE), show a down regulation of the TCRzeta chain and a concomitant upregulation of the TCR/CD3 chain and its interaction with FcRγ. Those studies show that the TCR/CD3/FcRgamma complex in effector cells recruits and activates Syk, instead of ZAP-70, tyrosine kinase. This physiologic switch in TCR signaling occurs exclusively in effector, and not naive or memory T cells[16,17,18.] Not surprisingly then, SYK inhibitors have been shown to delay disease progression and to improve survival in murine models of SLE[17, 18,19,20,21].

SYK inhibitors may also find a use in asthma, allergy, multiple sclerosis and other diseases such as thrombocytopenia purpura and T or B cell lymphomas[1,10, 14,22-35].

Treatment of prediseased NZB/W mice with a Syk inhibitor prevented the development of renal disease demonstrated by reduced glomerular sclerosis, tubular damage, proteinuria and BUN levels[18].

REFERENCES

1. Turner, M., Schweighoffer, E., Colucci, F., Di Santo, J. P. & Tybulewicz, V. L. Tyrosine kinase SYK: essential functions for immunoreceptor signalling. *Immunol Today* 21, 148-154 (2000).
2. Ghosh, D. & Tsokos, G. C. Spleen tyrosine kinase: an Src family of non-receptor kinase has multiple functions and represents a valuable therapeutic target in the treatment of autoimmune and inflammatory diseases. *Autoimmunity* 43, 48-55.
3. Lindvall, J. M., et al. Bruton's tyrosine kinase: cell biology, sequence conservation, mutation spectrum, siRNA modifications, and expression profiling. *Immunol Rev* 203, 200-215 (2005).
4. Gilfillan, A. M. & Tkaczyk, C. Integrated signalling pathways for mast-cell activation. *Nat Rev Immunol* 6, 218-230 (2006).
5. Gomez, G., Schwartz, L. & Kepley, C. Syk deficiency in human non-releaser lung mast cells. *Clin Immunol* 125, 112-115 (2007).
6. Kepley, C. L., Youssef, L., Andrews, R. P., Wilson, B. S. & Oliver, J. M. Syk deficiency in nonreleaser basophils. *J Allergy Clin Immunol* 104, 279-284 (1999).
7. Zou, W., et al. Syk, c-Src, the alphavbeta3 integrin, and ITAM immunoreceptors, in concert, regulate osteoclastic bone resorption. *J Cell Biol* 176, 877-888 (2007).
8. Reeve, J. L., et al. SLP-76 couples Syk to the osteoclast cytoskeleton. *J Immunol* 183, 1804-1812 (2009).
9. Klareskog, L., Catrina, A. I. & Paget, S. Rheumatoid arthritis. *Lancet* 373, 659-672 (2009).
10. Wong, B. R., Grossbard, E. B., Payan, D. G. & Masuda, E. S. Targeting Syk as a treatment for allergic and autoimmune disorders. *Expert Opin Investig Drugs* 13, 743-762 (2004).
11. Braselmann, S., et al. R406, an orally available spleen tyrosine kinase inhibitor blocks fc receptor signaling and reduces immune complex-mediated inflammation. *J Pharmacol Exp Ther* 319, 998-1008 (2006).
12. Pine, P. R., et al. Inflammation and bone erosion are suppressed in models of rheumatoid arthritis following treatment with a novel Syk inhibitor. *Clin Immunol* 124, 244-257 (2007).
13. Tomillero, A. & Moral, M. A. Gateways to clinical trials.*Methods Find Exp Clin Pharmacol* 31, 47-57 (2009).
14. Bajpai, M. Fostamatinib, a Syk inhibitor prodrug for the treatment of inflammatory diseases. *IDrugs* 12, 174-185 (2009).
15. Weinblatt, M. E., et al. Treatment of rheumatoid arthritis with a Syk kinase inhibitor: a twelve-week, randomized, placebo-controlled trial. *Arthritis Rheum* 58, 3309-3318 (2008).
16. Krishnan, S., Warke, V. G., Nambiar, M. P., Tsokos, G. C. & Farber, D. L. The FcR gamma subunit and Syk kinase replace the CD3 zeta-chain and ZAP-70 kinase in the TCR signaling complex of human effector CD4 T cells. *J Immunol* 170, 4189-4195 (2003).
17. Krishnan, S., et al. Differential expression and molecular associations of Syk in systemic lupus erythematosus T cells. *J Immunol* 181, 8145-8152 (2008).
18. Bahjat, F. R., et al. An orally bioavailable spleen tyrosine kinase inhibitor delays disease progression and prolongs survival in murine lupus. *Arthritis Rheum* 58, 1433-1444 (2008).
19. Smith, J., et al. A Spleen Tyrosine Kinase Inhibitor Reduces the Severity of Established Glomerulonephritis. *J Am Soc Nephrol* (2009).
20. Enyedy, E. J., et al. Fc epsilon receptor type I gamma chain replaces the deficient T cell receptor zeta chain in T cells of patients with systemic lupus erythematosus. *Arthritis Rheum* 44, 1114-1121 (2001).
21. Perl, A. Systems biology of lupus: mapping the impact of genomic and environmental factors on gene expression signatures, cellular signaling, metabolic pathways, hormonal and cytokine imbalance, and selecting targets for treatment. *Autoimmunity* 43, 32-47.
22. Smith, J., et al. A spleen tyrosine kinase inhibitor reduces the severity of established glomerulonephritis. *J Am Soc Nephrol* 21, 231-236.
23. Sanderson, M. P., Gelling, S. J., Rippmann, J. F. & Schnapp, A. Comparison of the anti-allergic activity of Syk inhibitors with optimized Syk siRNAs in FcepsilonRI-activated RBL-2H3 basophilic cells. *Cell Immunol* 262, 28-34.
24. Podolanczuk, A., Lazarus, A. H., Crow, A. R., Grossbard, E. & Bussel, J. B. Of mice and men: an open-label pilot study for treatment of immune thrombocytopenic purpura by an inhibitor of Syk. *Blood* 113, 3154-3160 (2009).
25. Bajpai, M., Chopra, P., Dastidar, S. G. & Ray, A. Spleen tyrosine kinase: a novel target for therapeutic intervention of rheumatoid arthritis. *Expert Opin Investig Drugs* 17, 641-659 (2008).
26. Friedberg, J. W., et al. Inhibition of Syk with fostamatinib disodium has significant clinical activity in non-Hodgkin lymphoma and chronic lymphocytic leukemia. *Blood* 115, 2578-2585.
27. Gao, C., et al. Eptifibatide-induced thrombocytopenia and thrombosis in humans require FcgammaRIIa and the integrin beta3 cytoplasmic domain. *J Clin Invest* 119, 504-511 (2009).
28. Marjon, K. D., Marnell, L. L., Mold, C. & Du Clos, T. W. Macrophages activated by C-reactive protein through Fc gamma RI transfer suppression of immune thrombocytopenia. *J Immunol* 182, 1397-1403 (2009).
29. Chen, L., et al. SYK-dependent tonic B-cell receptor signaling is a rational treatment target in diffuse large B-cell lymphoma. *Blood* 111, 2230-2237 (2008).
30. Ponzoni, M., et al. Syk expression patterns differ among B-cell lymphomas. *Leuk Res* (2010).
31. Pechloff, K., et al. The fusion kinase ITK-SYK mimics a T cell receptor signal and drives oncogenesis in conditional mouse models of peripheral T cell lymphoma. *J Exp Med* 207, 1031-1044 (2009).
32. Uckun, F. M., Ek, R. O., Jan, S. T., Chen, C. L. & Qazi, S. Targeting SYK kinase-dependent anti-apoptotic resistance pathway in B-lineage acute lymphoblastic leukaemia (ALL) cells with a potent SYK inhibitory pentapeptide mimic. *Br J Haematol* 149, 508-517 (2010).

33. Wilcox, R. A., et al. Inhibition of Syk protein tyrosine kinase induces apoptosis and blocks proliferation in T-cell non-Hodgkin's lymphoma cell lines. *Leukemia* 24, 229-232 (2009).
34. Feldman, A. L., et al. Overexpression of Syk tyrosine kinase in peripheral T-cell lymphomas. *Leukemia* 22, 1139-1143 (2008).
35. Wang, L., et al. Alternative splicing disrupts a nuclear localization signal in spleen tyrosine kinase that is required for invasion suppression in breast cancer. *Cancer Res* 63, 4724-4730 (2003).

In addition to mast cells, Syk is expressed in other hematopoietic cells including B cells, where it is thought to play an essential role in transducing signals required for the transition of immature B cells into mature recirculating B cells (M. Turner et al, Immunology Today, 21: 148 (2000). B cells are reported to play an important role in some inflammatory conditions such as lupus (0. T. Chan et al., Immunological Rev, 169: 107-121 (1999) and rheumatoid arthritis (A. Cause et al, Biodrugs, 15(2): 73-79 (2001).

Syk was also reported to be an element of the signaling cascade in beta-amyloid and prion fibrils leading to production of neurotoxic products (C. K. Combs et al., J. Neuroscl, 19: 928-939 (1999). Furthermore, an inhibitor of Syk blocked the production of these neurotoxic products. Thus furopyridine derivatives would potentially be useful in the treatment of Alzheimer's disease and related neuroinflammatory diseases. Another report (Y. Kuno et al., Blood, 97, 1050-1055 (2001) demonstrates that Syk plays an important role in malignant progression. A TEL-Syk fusion protein was found to transform hematopoietic cells suggesting a role in the pathogenesis of hematopoietic malignancies. Therefore compounds of formula I may be useful in the treatment of certain types of cancers.

Other protein tyrosine kinases involved in hematologic malignancies include ABL (ABLI), ARG (ABL2), PDGFβR, PDGFaR, JAK2, TRKC, FGFRI, FGFR3, FLT3, and FRK.

The Janus kinases (JAK) are a family of tyrosine kinases consisting of JAKI, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas (for a review of the pharmaceutical intervention of the JAK/STAT pathway see Frank, Mol. Med. 5, 432:456 (1999), and Seidel et al, Oncogene 19, 2645-2656 (2000). JAK2 is a well validated target with strong potential in the treatment of myeloproliferative disorders (MPDs), which include polycythemia vera (PV), essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Fms-like tyrosine kinase 3 (FLT3), which is also known as FLK-2 (fetal liver kinase 2) and STK-I (stem cell kinase 1), plays an important role in the proliferation and differentiation of hematopoietic stem cells. FLT3 receptor kinase is expressed in normal hematopoietic cells, placenta, gonads, and brain. However, this enzyme is expressed at very high levels on the cells of more than 80% of myelogenous patients and of a fraction of acute lymphoblastic leukemia cells. Furthermore, the enzyme can also be found on cells from patients with chronic myelogenous leukemia in lymphoid blast crisis. It has been reported that FLT3 kinase is mutated in 30% of acute myeloid leukemia (AML) and in a subset of acute lymphoblastic leukemia (ALL) as well (Gilliland et al, Blood 100, 1532-1542 (2002); Stirewalt et al, Nat. Rev. Cancer, 3, 650-665 (2003). The most common activating mutations in FLT3 are internal tandem duplications within the juxtamembrane region, while point mutations, insertions, or deletions in the kinase domain are less common. Some of these mutant FLT3 kinases are constitutively active. FLT3 mutations have been associated with a poor prognosis (Malempati et al., Blood, 104, 11 (2004). More than a dozen known FLT3 inhibitors are being developed and some have shown promising clinical effects against AML (Levis et al Int. J. Hematol, 52, 100-107 (2005).

It has been reported that some of small-molecule FLT3 inhibitors are effective in inducing apoptosis in cell lines with FLT3-activating mutations and prolonging survival of mice that express mutant FLT3 in their bone marrow cells (Levis et al, Blood, 99, 3885-3891 (2002); Kelly et al, Cancer Cell, 1, 421-432 (2002); Weisberg et al, Cancer Cell, 1, 433-443 (2002); Yee et al, Blood, 100, 2941-2949 (2002).

In particular, the present invention relates to compounds and to the use of compounds in which the inhibition, regulation and/or modulation of signal transduction by Syk plays a role.

The synthesis of small compounds which specifically inhibit, regulate and/or modulate signal transduction by tyrosine kinases in particular Syk, is therefore desirable and an aim of the present invention.

Moreover, aim of this invention is the synthesis of new compounds for the prevention and treatment of rheumatoid arthritis, systemic lupus, asthma, allergic rhinitis, ITP, multiple sclerosis, leukemia, breast cancer and maligna melanoma. Surprisingly we have identified furopyridines that inhibit selectively SYK, BTK, KDR, Src, Zap70, Fak, Pyk2, Flt3 or Jak or inhibit a selection of these kinases.

Moreover, compounds of formula I inhibit serin kinase GCN2.

Many strategies of cancer treatment of solid tumors focus on the surgically removal of the tumor mass as far as possible and the subsequent eradication of any residual tumor cells by radiotherapy and chemotherapy with cytotoxic agents or inhibitors that target cancer cell pathways more specifically. However, the success of such approach is limited and often does not persist. This is mainly due to the narrow therapeutic window for such cytotoxic agents (specificity and side effects) and to the capability of cancer calls to adapt to the selective pressure applied by cytotoxic or other inhibitory agents. The survival of a small number of tumor (stem) cells that acquired resistance to the initial treatment can be sufficient to seed the regrowth of a tumor. These relapses are in most cases more difficult to treat compared to that of the initial tumors. As a consequence the more successful targeting of tumor cells may require targeting multiple survival and escape mechanism of tumor cells in parallel (Muller & Prendegast 2007).

Development of malignancies is accompanied by a major roll up of the cellular physiology. During this process several qualities are acquired by the cancer cells that are basis for immortalization or insensitivity to growth inhibitory signals. In addition the tumor cells also modify the interaction with the microenvironment and beyond. The latter area includes the strategies of tumor cells to escape from the immunological surveillance (Muller & Prendegast 2007). The immune surveillance limits malignant growth but also provides a selective pressure triggering the evolution of mechanisms for evading the immune response as reviewed by [Dunn et al. 2004]. Essentially it has been frequently observed that ablation of T cell immunity is sufficient to increase tumor incidence [Shankaran et al. 2001] and it is believed that immune escape is affecting tumor dormancy versus progression, promoting invasion and metastasis and negatively impacts on therapeutic response.

Several mechanistic studies discovered that immune escape has an important interface with metabolic alterations within the tumor microenvironment. Here important roles in mediating immune tolerance to antigens have been associated to the catabolism of the essential amino acids tryptophan and arginine, carried out by the enzymes indoleamine 2,3-dioxygenase (IDO) and arginase I (ARG), respectively (Bronte and Zanovello, 2005; Muller et al., 2005b; Muller and Prendergast, 2007; Munn and Mellor, 2007; Popovic et al., 2007).

IDO is a single-chain oxidoreductase that catalyzes the degradation of tryptophan to kynurenine. IDO is not responsible for catabolizing excess dietary tryptophan but to modulate tryptophan level in a local environment. Elevations in tryptophan catabolism in cancer patients manifest in significantly altered serum concentration of tryptophan or catabolites and this was correlated to IDO which is commonly elevated in tumors and draining lymph nodes. According to several publications IDO overexpression is associated with poor prognosis in cancer [Okamoto et al 2005; Brandacher et al, 2006].

T cells appear to be preferentially sensitive to IDO activation, such that when starved for tryptophan they cannot divide and as a result cannot become activated by an antigen presented to them. Munn and Mellor and their colleagues, revealed that IDO modulates immunity by suppressing T-cell activation and by creating peripheral tolerance to tumor antigens (Mellor and Munn, 2004). These mechanism encompass the subversion of immune cells recruited by the tumor cell to its immediate microenvironment or to the tumor-draining lymph nodes Here the tumor antigens that were scavenged by antigen-presenting cells are cross-presented to the adaptive immune system. In addition to being directly tolaragenic, mature DCs have the capacity to expand regulatory Tcells (Tregs) [Moser 2003].

Beside tryptophan catabolism the conversion of arginine is increased in a tumor-conditioned microenvironment, and numerous reports indicate a role for the activation of arginases during tumor growth and development. In tumor-infiltrating myeloid cells, arginine is converted by arginase I (ARG1), arginase II (ARG2) to urea and ornithine and oxidized by the inducible form of nitric oxide synthase (NOS2) to citrulline and nitric oxide (NO). Increased ARG activity is frequently observed in patients with colon, breast, lung, and prostate cancer [Cederbaum 2004] correlating with the overexpression of ARG and NOS found in prostate cancers [Keskinege et al. 2001, Aaltoma et al. 2001, Wang et al. 2003]. It was shown that ARG activity in infiltrating macrophages impairs antigen-specific T cell responses and the expression of the CD3 receptor. Moreover the cumulative activity of ARG and NOS in tumor associated myeloid cells can generate inhibitory signals to antigen-specific T lymphocytes that eventually lead to apoptosis [Bronte 2003 a; 2003b].

Both, the IDO and the ARG related mechanism merge at the point of sensing the depleted concentration of the respective amino acid concentration. During amino acid deprivation, the eIF2 kinase EIF2AK4 called general control nonderepressible 2 (GCN2) is interacting with the intracellular accumulating deacylated tRNA. As a consequence the GCN2 is assumed to change from an auto-inhibited to an active conformation and further activate by auto-phosphorylation. Then the only known substrate protein eIF2a becomes phosphorylated and as a consequence the complex for translation initiation is inhibited [Harding et al. 2000,]. This diminishes the general Cap-dependent translation initiation and by this the corresponding protein production. On the other hand this induces the specific expression of stress related target genes mainly by cap-independent initiation via the activating transcription factor 4 (ATF4). By expressing the respective stress response proteins, e.g. enzymes in the in amino acid metabolism, the cell tries to compensate the particular cell stress [Wek et al. 2006]. If the stress persists, the same pathway will switch to promoting cell death via transcription of the pro-apoptotic transcription factor, CCAAT/enhancer-binding protein homologous protein (CHOP) [Oyadomari 2004]. It was shown that, tryptophan starvation triggers a GCN2-dependent stress signaling pathway In T cells altering eIF2aphosphorylation and translational initiation leading to a cell growth arrest (Munn et al. 2005). Sharma, et al. published on the direct IDO-induced and GCN2-dependent activation of mature Tregs. Similarly Fallarino et al[2006] found a GCN2-dependent conversion of CD4+CD25-cells to CD25+FoxP3+Tregs producing IL-10 and TGFβ. Rodriguez et al. [2007] identified that activation of the GCN2 pathway via tryptophan or arginine depletion in combination with TCR signaling leads to CD3 ζ chain down regulation, cell cycle arrest and anergy.

Importantly the GCN2 pathway is not only important for the tumoral immune escape but also plays an active role in modulating tumor survival directly. Ye et al[2010] found that the aforementioned transcription factor ATF4 is over-expressed inhuman solid tumors, suggesting an important function in tumour progression. Amino acid and glucose deprivation are typical stresses found in solid tumours and activated the GCN2 pathway to up-regulate ATF4 target genes involved in amino acid synthesis and transport. GCN2 activation/overexpression and increased phospho-eIF2a were observed in human and mouse tumors compared with normal tissues and abrogation of ATF4 or GCN2 expression significantly inhibited tumor growth in vivo. It was concluded that the GCN2-eIF2a-ATF4 pathway is critical for maintaining metabolic homeostasis in tumor cells.

Over all the present biology makes an interference with the ARG/IDO pathway attractive for braking up the tumoral immune escape by adaptive mechanism. The interference of GCN2 function is here of particular interest as it is a merging point of the two pathways, the IDO and ARG, as well as it provides additional opportunities to impede with the tumor metabolism directly.

Several pathway inhibitors are already considered as immune modulators. These inhibitors address mainly the enzymatic function of the IDO or ARG proteins (Muller and Scherle, 2006). The application of the arginase inhibitor, N-hydroxy-nor-L-Arg blocks growth of s.c. 3LL lung carcinoma in mice [Rodriguez 2004]. The NO-donating aspirins like NCX 4016 (2-(acetyloxy)benzoic acid 3-(nitrooxymethyl) phenyl ester) have been reported to interfer with the inhibitory enzymatic activities of myeloid cells. Orally administered NO aspirin normalized the immune status of tumor-bearing hosts, increased the number and function of tumor-antigen-specific T lymphocytes, and enhanced the preventive and therapeutic effectiveness of the antitumor immunity elicited by cancer vaccination (DeSanto 2005) The substrate analogue 1 methyl-tryptophan (1 MT)

and related molecules have been used widely to target IDO in the cancer context and other settings. Studies by Friberg et al. (2002) and Uyttenhove et al. (2003) demonstrated that 1 MT can limit the growth of tumors over-expressing IDO. However 1 MT was unable to elicit tumor regression in several tumor models, suggesting only modest antitumor efficacy when IDO inhibition was applied as a monotherapy. In contrast, the combinatory treatment with 1 MT and a variety of cytotoxic chemotherapeutic agents elicited regression of established MMTV-neu/HER2 tumors, which responded poorly to any single-agent therapy [Muller et al 2005a]. Immunodepletion of CD4+ or CD8+ T cells from the mice, before treatment abolished the combinatorial efficacy observed in this model, confirming the expectation that 1 MT acted indirectly through activation of T cell-mediated antitumor immunity. Important evidence that IDO targeting is essential to 1 MT action was provided by the demonstration that 1 MT lacks antitumor activity in mice that are genetically deficient for IDO [Hou et al., 2007]

The inhibition of GCN2 would enable to combine the two pathway branches of amino acrid starvation induced immunoediting and would reduce the options for the tumor to circumvent the inhibition of either branch. Moreover, as detailed above, the GCN2 inhibition provides the opportunity for interfering with the tumor metabolism at the same time what may enhance the efficacy of a monotherapy or a combination therapy with other anticancer approaches.

LITERATURE

1. Aaltoma, S. H., P. K. Lipponen, and V. M. Kosma. 2001. Inducible nitric oxide synthase (iNOS) expression and its prognostic value in prostate cancer. Anticancer Res. 21:3101-3106.
2. Brandacher, G.; Perathoner, A.; Ladurner, R.; Schneeberger, S.; Obrist, P.; Winkler, C.; Werner, E. R.; Werner-Felmayer, G.; Weiss, H. G.; Gobel, G.; Margreiter, R.; Konigsrainer, A.; Fuchs, D.; Amberger, A. Prognostic value of indoleamine 2,3-dioxygenase expression in colorectal cancer: effect on tumorinfiltrating T cells. Clin. Cancer Res. 2006, 12, 1144-1151.
3. Bronte V, Zanovello P. (2005). Regulation of immune responses by L-arginine metabolism. Nat Rev Immunol 5: 641-654.
4. Bronte, V., P. Serafini, C. De Santo, I. Marigo, V. Tosello, A. Mazzoni, D. M. Segal, C. Staib, M. Lowel, G. Sutter, et al. 2003a. IL-4-induced arginase 1 suppresses alloreactive T cells in tumor-bearing mice. J. Immunol. 170: 270-278.
5. Bronte, V., P. Serafini, A. Mazzoni, D. M. Segal, and P. Zanovello. 2003b. L-arginine metabolism in myeloid cells controls T-lymphocyte functions. Trends Immunol. 24:302-306
6. Carmela De Santo, Paolo Serafini, Ilaria Marigo, Luigi Dolcetti, Manlio Bolla, § Piero Del Soldato, Cecilia Melani, Cristiana Guiducci, Mario P. Colombo, Manuela lezzi, Piero Musiani, Paola Zanovello, and Vincenzo Bronte. Nitroaspirin corrects immune dysfunction in tumor-bearing hosts and promotes tumor eradication by cancer vaccination. Proc Natl Acad Sci USA. 2005 March 15; 102(11): 4185-4190
7. Cederbaum, S. D., H. Yu, W. W. Grody, R. M. Kern, P. Yoo, and R. K. Iyer. 2004. Arginases I and II: do their functions overlap? Mol. Genet. Metab. 81: S38-44.
8. Dey, M., Cao, C., Sicheri, F. and T. E. Dever. Conserved Intermolecular Salt Bridge Required for Activation of Protein Kinases PKR, GCN2, and PERK. JBC 282(9): 6653, 2007.
9. Dunn, G. P.; Old, L. J.; Schreiber, R. D. The immunobiology of cancer immunosurveillance and immunoediting. Immunity 2004, 21, 137-148.
10. Fallarino, F. U. Grohmann, S. You, B. C. et al. The combined effects fo tryptophan starvation and tryptophan catabolites down-regulate T cell receptor zeta-chain and induce a regulatory phenotype in naïve T cells. J. Immunol. 176:6752, 2006.
11. Friberg M, Jennings R, Alsarraj M, Dessureault S, Cantor A, Extermann M et al. (2002). Indoleamine 2,3-dioxygenase contributes to tumor cell evasion of T cell-mediated rejection. Int. J Cancer 101: 151-155
12. Harding H P, Novoa I, Zhang Y, Zeng H, Wek R, Schapira M, Ron D. Regulated translation initiation controls stress-induced gene expression in mammalian cells. Mol Cell. 2000 November; 6(5):1099-108.
13. Hou D Y, Muller A J, Sharma M D, DuHadaway J, Banerjee T, Johnson M et al. (2007). Inhibition of indoleamine 2,3-dioxygenase in dendritic cells by stereoisomers of 1-methyl-tryptophan correlates with antitumor responses. Cancer Res 67: 792-801.
14. Keskinege, A., S. Elgun, and E. Yilmaz. 2001. Possible implications of arginase and diamine oxidase in prostatic carcinoma. Cancer Detect. Prev. 25:76-79.
15. Mellor A L, Munn D H. (2004). IDO expression by dendritic cells: tolerance and tryptophan catabolism. Nat Rev Immunol 4: 762-774.
16. Moser, M. Dendritic cells in immunity and tolerance-do they display opposite functions? Immunity 2003, 19, 5-8.
17. Muller, A. J. and P. A. Scherle. Targeting the mechanisms of tumoral immune tolerance with small-molecule inhibitors. Nat. Rev. Cancer. 6:613, 2006.
18. Muller A J, Prendergast G C. (2007). Indoleamine 2,3-dioxygenase in immune suppression and cancer. Curr Cancer Drug Targets 7: 31-40.
19. Muller A J, DuHadaway J B, Sutanto-Ward E, Donover P S, Prendergast G C. (2005a). Inhibition of indoleamine 2,3-dioxygenase, an immunomodulatory target of the tumor suppressor gene Bin1, potentiates cancer chemotherapy. Nature Med 11: 312-319.
20. Muller A J, Malachowski W P, Prendergast G C. (2005b). Indoleamine 2,3-dioxygenase in cancer: targeting pathological immune tolerance with small-molecule inhibitors. Expert Opin Ther Targets 9:831-849.
21. Munn, D. H., M. D. Sharma, B. Baban, H. P. Harding, Y. Zhang, D. Ron, A. L. Mellor. GCN2 kinase in T cells mediates proliferative arrest and anergy induction in response to indoleamine 2,3-dioxygenase. Immunity. 22:633, 2005
22. Okamoto, A.; Nikaido, T.; Ochiai, K.; Takakura, S.; Saito, M.; Aoki, Y.; Ishii, N.; Yanaihara, N.; Yamada, K.; Takikawa, O.; Kawaguchi, R.; Isonishi, S.; Tanaka, T.; Urashima, M. Indoleamine 2,3-dioxygenase serves as a marker of poor prognosis in gene expression profiles of serous ovarian cancer cells. Clin. Cancer Res. 2005, 11, 6030-6039.
23. Oyadomari S, Mori M. Roles of CHOP/GADD153 in endoplasmic reticulum stress. Cell Death Differ. 2004 April; 11(4):381-9.
24. G C Prendergast, Immune escape as a fundamental trait of cancer: focus on IDO. Oncogene (2008) 27, 3889-3900
25. Popovic P J, Zeh III H J, Ochoa J B. (2007). Arginine and immunity. J Nutr 137:1681S-1686 S.

26. Rodriguez, P. C., D. G. Quiceno, J. Zabaleta, B. Ortiz, A. H. Zea, M. B. Piazuelo, A. Delgado, P. Correa, J. Brayer, E. M. Sotomayor, S. Antonia, J. B. Ochoa, and A. C. Ochoa. Arginase I Production in the Tumor Microenvironment by Mature Myeloid Cells Inhibits T-Cell Receptor Expression and Antigen-Specific T-Cell Responses. Canc. Res. 64:5839, 2004
27. Rodriguez, P. C., D. G. Quiceno, and A. C. Ochoa. L-arginine availability regulates T-lymphocyte cell-cycle progression. Blood. 109:1568, 2007.
28. Shankaran, V.; Ikeda, H.; Bruce, A. T.; White, J. M.; Swanson, P. E.; Old, L. J.; Schreiber, R. D. IFNgamma and lymphocytes prevent primary tumour development and shape tumour immunogenicity. Nature 2001, 410, 1107-1111.
29. Sharma, M. D., B. Baban, P. Chandler, D-Y. Hou, N. Singh, H. Yagita, M. Azuma, B. R. Blazar, A. L. Mellor, and D. H. Munn. Plasmacytoid dendritic cells from mouse tumor-draining lymph nodes directly activate mature Tregs via indoleamine 2,3-dioxygenase. J. Clin. Invest. 117:2570, 2007.
30. Uyttenhove C, Pilotte L, Theate I, Stroobant V, Colau D, Parmentier N et al. (2003). Evidence for a tumoral immune resistance mechanism based on tryptophan degradation by indoleamine 2,3-dioxygenase. Nat Med 9:1269-1274
31. Wang, J., M. Torbenson, Q. Wang, J. Y. Ro, and M. Becich. 2003. Expression of inducible nitric oxide synthase in paired neoplastic and non-neoplastic primary prostate cell cultures and prostatectomy specimen. Urol. Oncol. 21:117-122.
32. Wek R C, Jiang H Y, Anthony T G. Coping with stress: eIF2 kinases and translational control. Biochem Soc Trans. 2006 February; 34 (Pt 1):7-11.
33. Ye J, Kumanova M, Hart L S, Sloane K, Zhang H, De Panis D N, Bobrovnikova-Marjon E, Diehl J A, Ron D, Koumenis C. The GCN2-ATF4 pathway is critical for tumour cell survival and proliferation in response to nutrient deprivation. EMBO J. 2010 June 16; 29(12): 2082-96.

It has been found that the compounds according to the invention and salts thereof have very valuable pharmacological properties while being well tolerated.

The present invention specifically relates to compounds of the formula I which inhibit, regulate and/or modulate signal transduction by Syk, to compositions which comprise these compounds, and to processes for the use thereof for the treatment of Syk-induced diseases and complaints.

The compounds of the formula I can furthermore be used for the isolation and investigation of the activity or expression of Syk. In addition, they are particularly suitable for use in diagnostic methods for diseases in connection with unregulated or disturbed Syk activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

PRIOR ART

Other heterocyclic compounds are described in WO 2011/075699, U.S. Pat. No. 7,732,446, WO 2009/046448, WO 2009/134973.

Other heterocyclic Syk inhibitors are described in WO2008/118823, WO2009/136995, WO 2010/027500.

SUMMARY OF THE INVENTION

The invention relates to compounds of the formula I

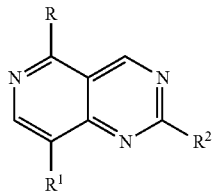

in which
R denotes H, OH, A or NR$^4$R$^{4'}$,
R$^1$ denotes Ar$^1$, Het$^1$, CN, A or —C≡C—Ar$^1$,
R$^2$ denotes Het$^2$, NR$^3$Cyc, NR$^3$CR$^3$CON(R$^3$)$_2$, NR$^3$[C(R$^3$)$_2$]$_p$CR$^3$(NH$_2$)CH$_2$OA or NR$^3$[C(R$^3$)$_2$]$_p$N(R$^3$)$_2$,
Ar$^1$ denotes phenyl, which is mono-, di- or trisubstituted by A, (CH$_2$)$_n$Het$^3$, [C(R$^3$)$_2$]$_n$OR$^3$, [C(R$^3$)$_2$]$_n$N(R$^3$)$_2$, NO$_2$, CN, Hal, COOR$^3$, CON(R$^3$)$_2$, NR$^3$COA, NR$^3$SO$_2$A, SO$_2$N(R$^3$)$_2$ and/or S(O)$_m$A,
Het$^1$ denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]oxazinyl, 4H-benzo[1,4]-oxazinyl, benzimidazolyl, pyridyl, pyrimidinyl, imidazolyl, pyrazolyl, furyl, thiazolyl, triazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, SO$_2$NH$_2$, (CH$_2$)$_n$NH$_2$, (CH$_2$)$_n$NHA, (CH$_2$)$_n$NA$_2$ and/or =O,
Het$^2$ denotes piperidinyl, piperazinyl, pyrrolidinyl, morpholinyl, tetrahydropyranyl, pyrazolyl, indazolyl, azetidinyl or octahydro-benzimidazolyl, each of which is mono-, di- or trisubstituted by Hal, A, (CH$_2$)$_n$NH$_2$, (CH$_2$)$_n$NHA, (CH$_2$)$_n$NA$_2$, (CH$_2$)$_n$OH and/or (CH$_2$)$_n$OA,
Het$^3$ denotes piperidinyl, piperazinyl, pyrrolidinyl, morpholinyl, imidazolidinyl, pyridyl, pyrimidinyl, imidazolyl, pyrazolyl, furyl, thiazolyl or triazolyl, each of which is unsubstituted or mono- or disubstituted by A and/or =O,
R$^3$ denotes H or alkyl having 1, 2, 3 or 4 C-atoms,
R$^4$, R$^{4'}$ each, independently of one another, denote H or A,
A denotes unbranched or branched alkyl having 1-10 C atoms, in which 1-7H atoms may be replaced by F and/or in which one or two non-adjacent CH$_2$ groups may be replaced by O and/or NH, or
cyclic alkyl having 3-7 C atoms,
Cyc denotes cyclic alkyl having 3-7 C atoms, which may be unsubstituted or monosubstituted by NH$_2$, CN, CONH$_2$ or OH,
m denotes 0, 1 or 2,
n denotes 0, 1, 2, 3 or 4,
p denotes 1, 2, 3 or 4,
and pharmaceutically acceptable solvates, salts, enantiomers, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides. It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Claimed compounds such as N2-((cis)-2-Amino-cyclohexyl)-8-(1-methyl-1H-pyrazol-4-yl)-pyrido[4,3-d]pyrimidine-2,5-diamine refers to the two enantiomers of the claimed cis-compound.

A claimed compound such as (3-fluoro-piperidin-3-ylmethyl)-[8-(6-trifluoromethyl-1H-indol-3-yl)-pyrido[4,3-d]pyrimidin-2-yl]-amine refers to the two enantiomers ("A78" and "A79").

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution, such as

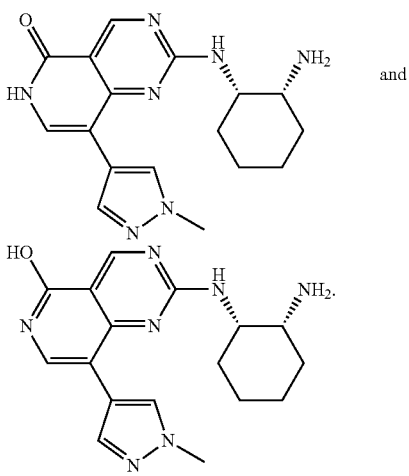

The invention relates to the compounds of the formula I and salts thereof and to a process for the preparation of compounds of the formula I and pharmaceutically acceptable salts, solvates, enantiomers, tautomers and stereoisomers thereof, characterised in that
a) for the preparation of compounds of the formula I, wherein
R denotes $NR^4R^{4'}$ and
$R^2$ denotes $NR^3Cyc$, $NR^3CR^3CON(R^3)_2$, $NR^3[C(R^3)_2]_pCR^3(NH_2)CH_2OA$ or
$NR^3[C(R^3)_2]_pN(R^3)_2$,
a compound of the formula II

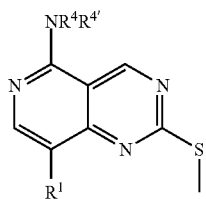

II in which $R^1$, $R^4$, $R^{4'}$ have the meanings indicated in claim 1, is reacted with a compound of the formula III

III $R^2$-$NHR^3$ in which $R^2$ and $R^3$ have the meanings indicated in claim 1, or
b) for the preparation of compounds of the formula I, wherein
R denotes H,
a compound of the formula IV

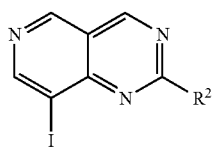

IV in which $R^1$, $R^4$, $R^{4'}$ have the meanings indicated in claim 1, is reacted with a compound of the formula V

V $R^1$-L in which $R^1$ has the meaning indicated in claim 1, and L denotes a boronic acid or a boronic acid ester group, in a Suzuki-type coupling,
and/or
a base or acid of the formula I is converted into one of its salts.

Above and below, the radicals R, $R^1$ and $R^2$ have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $OCH_2CH_2OCH_3$, $NHCH_2CH_2OH$, $CH_2CH_2OH$, $CH_2NHCH_2$ or $NHCH_2CH_3$.

Cyclic alkyl (cycloalkyl) preferably denotes cyclopropyl, cyclobutyl, cyclopentyl, cyclohexyl or cycloheptyl.

Cyc denotes cyclic alkyl having 3-7 C atoms, preferably denotes cyclopropyl, cyclobutyl, cyclopentyl, cyclohexyl or cycloheptyl.

R preferably denotes H, $NR^4R^{4'}$, OH, methyl or $CHF_2$.
$R^3$ preferably denotes H or methyl.
Hal preferably denotes F, Cl or Br, but also I, particularly preferably F or Cl.
$Ar^1$ preferably denotes phenyl, which is mono-, di- or trisubstituted by A, $(CH_2)_nHet^3$ and/or $SO_2NH_2$.

$Het^1$ preferably denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]oxazinyl, 4H-benzo[1,4]oxazinyl, benzimidazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, and/or =O.

$Het^2$ preferably denotes piperidinyl or octahydro-benzimidazolyl, each of which is monosubstituted by A, $(CH_2)_nOH$ or $(CH_2)_nOA$.

$Het^3$ preferably denotes triazolyl.

Accordingly, the invention relates, in particular, to the compounds of the formula I in which at least one of the said radicals has one of the preferred meanings indicated above. Some preferred groups of compounds may be expressed by the following sub-formulae Ia to Ie, which conform to the formula I and in which the radicals not designated in greater detail have the meaning indicated for the formula I, but in which
in Ia $Ar^1$ denotes phenyl, which is mono-, di- or trisubstituted by A, $(CH_2)_nHet^3$ and/or $SO_2NH_2$;
in Ib $Het^1$ denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]-oxazinyl, 4H-benzo[1,4]oxazinyl, benzimidazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, and/or =O;

in Ic Het² denotes piperidinyl or octahydro-benzimidazolyl, each of which is monosubstituted by A, $(CH_2)_nOH$ or $(CH_2)_nOA$;
in Id Het³ denotes triazolyl;
in Ie R denotes H, OH, A or $NR^4R^{4'}$,
R¹ denotes Ar¹, Het¹, CN, A or —C≡C—Ar¹,
R² denotes Het², $NR^3Cyc$, $NR^3CR^3CON(R^3)_2$, $NR^3[C(R^3)_2]_p$ $CR^3(NH_2)CH_2OA$ or $NR^3[C(R^3)_2]_pN(R^3)_2$,
Ar¹ denotes phenyl, which is mono-, di- or trisubstituted by A, $(CH_2)_nHet^3$ and/or $SO_2NH_2$,
Het¹ denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]-oxazinyl, 4H-benzo[1,4]oxazinyl, benzimidazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, and/or =O,
Het² denotes piperidinyl or octahydro-benzimidazolyl, each of which is monosubstituted by A, $(CH_2)_nOH$ or $(CH_2)_nOA$,
Het³ denotes triazolyl,
R³ denotes H or alkyl having 1, 2, 3 or 4 C-atoms,
$R^4$, $R^{4'}$ each, independently of one another, denote H or A,
A denotes unbranched or branched alkyl having 1-10 C atoms, in which 1-7H atoms may be replaced by F and/or in which one or two non-adjacent $CH_2$ groups may be replaced by O and/or NH,
or
cyclic alkyl having 3-7 C atoms,
Cyc denotes cyclic alkyl having 3-7 C atoms, which may be unsubstituted or monosubstituted by $NH_2$, CN, $CONH_2$ or OH,
m denotes 0, 1 or 2,
n denotes 0, 1, 2, 3 or 4,
p denotes 1, 2, 3 or 4;
and pharmaceutically acceptable salts, solvates, enantiomers, tautomers and stereoisomers thereof, including mixtures thereof in all ratios.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise. Use can also be made here of variants known per se which are not mentioned here in greater detail.

The starting compounds of the formulae II, III, IV and V are generally known. If they are novel, however, they can be prepared by methods known per se.

Compounds of the formula I can preferably be obtained by reacting a compound of the formula IV with a compound of the formula V.

In the compounds of the formula V, L preferably denotes

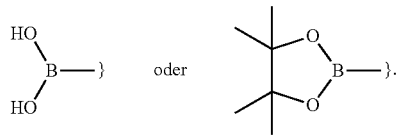

The reaction is generally carried out under conditions of a Suzuki-type coupling. Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon di-sulfide; carboxylic acids, such as formic acid or acetic acid; nitro compounds, such as nitromethane or nitrobenzene; esters, such as ethyl acetate, or mixtures of the said solvents.

Particular preference is given to ethanole, toluene, dimethoxyethane, 1,4-dioxane and/or water.

Moreover, compounds of the formula I can preferably be obtained by reacting a compound of the formula II with a compound of the formula III. The reaction is generally carried out under conditions known to the skilled artisan and which are known and suitable for the said reaction.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an $NH_2$ group.

Preference is furthermore given to starting materials which carry a hydroxylprotecting group instead of the H atom of a hydroxyl group, for example those which conform to the formula I, but contain an R"O-phenyl group (in which R" is a hydroxylprotecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxy-methyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred aminoprotecting groups are BOC and Mtr, furthermore CBZ, Fmoc, benzyl and acetyl.

The term "hydroxylprotecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxylprotecting groups are not crucial since they are removed again after the desired chemical reaction or reaction sequence; preference is given to groups having 1-20, in particular 1-10, carbon atoms. Examples of hydroxylprotecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like.

Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, formate, fumarate, galacterate (from mucic acid), galacturonate, gluco-heptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanol-amine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1$-$C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner.

The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Exam-ples of isotopes which are readily commercially available and which can be incorporated into a compound of the formula I by well-known methods include isotopes of hydrogen, carbon, nitrogen, oxygen, phos-phorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other iso-topes of other atoms is intended to be part of the present invention. An isotope-labelled compound of the formula I can be used in a number of beneficial ways. For example, an isotope-labelled compound of the formula I into which, for example, a radioisotope, such as $^3$H or $^{14}$C, has been incorporated is suitable for medicament and/or substrate tissue distribution assays. These radioisotopes, i.e. tritium ($^3$H) and carbon-14 ($^{14}$C), are particularly preferred owing to simple preparation and excellent detectability. Incor-po-ra-tion of heavier isotopes, for example deuterium ($^2$H), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodi-ment of the present invention. An isotope-labelled compound of the formula I can usually be prepared by carrying out the procedures dis-closed in the synthesis schemes and the related description, in the example part and in the preparation part in the present text, replacing a non-isotope-labelled reactant by a readily available isotope-labelled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materi-als costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determi-nations enable favourable and accurate determination of the extent of the extent to which the improve-ment in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for admin-istration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates, enantiomers, tautomer and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-capro-lactone, polyhydroxybutyric acid, polyorthoesters, polyacetals, polydihydroxypyrans, polycyanoacrylates and crosslinked or amphipathic block co-polymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The disclosed compounds of the formula I can be administered in combination with other known therapeutic agents including agents for the treatment of RA (rheumatoid arthritis). As used here, the term "agents for the treatment of RA" relates to any agent which is administered to a patient with RA for the purposes of treating the RA.

The medicaments below are preferably, but not exclusively, combined with the compounds of the formula I:
1. NSAIDs (non-steroidal anti-inflammatory drugs) and analgesics
2. Glucocorticoids (low oral doses)
3. Conventional disease-modifying antirheumatic drugs (DMARDs)
    Methotrexate
    Leflunomide
    Sulfasalazine
    Hydroxycloroquine
    Azathioprine
    Ciclosporin
    Minocycline
    Gold
4. Biologic response modifiers (BRMs) →target molecules/immune cells involved in the inflammatory process, and include the following agents:
    TNF inhibitors
        etanercept (Enbrel)
        infliximab (Remicade)
        adalimumab (Humira)
    B-cell-directed therapy
        rituximab (Rituxan)
    T-cell/B-cell coactivation signal inhibitor
        abatacept (Orencia)
    IL-1 receptor antagonist
        anakinra (Kineret)

| | MECHANISM OF ACTION |
|---|---|
| Golimumab | Fully humanized monoclonal antibody to TNF |
| Certolizumab pegol | Anti-TNF agent with just the Fab portion attached to the polyethylene glycol |
| Tocilizumab | Humanized monoclonal anti-IL-6 antibody that binds to the soluble and membrane-expresses IL-6 receptor |
| Ocrelizumab | Humanized-second generation anti-CD20 antibody that depletes B cells |
| Ofatumumab | Human monoclonal anti-CD20 IgG1 antibody |
| Denosumab | Fully humanized monoclonal antibody that binds to and inhibits the receptor activator for nuclear factor-kB ligand |
| TRU-015 | New class of CD20-directed protein therapeutics |
| Oral small molecules (JAK, Syk, MAP kinase inhibitors) | Cytoplasmic targets |
| Tolerogens (dnaJP1) | Immunotherapy based on T-cell tolerization |

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates, enantiomers, tautomers and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically acceptable salts, solvates, enantiomers, tautomers and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates, enantiomers, tautomers and stereoisomers thereof, including mixtures thereof in all ratios,
and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer, metabolic conditions or conditions treatable or preventable by inhibition of a kinase or a kinase pathway, in one embodiment, the Syk, FLT-3, JAK1 and/or JAK2 pathway. In one embodiment an effective amount of a compound of formula (I) is an amount that inhibits a kinase in a cell, such as, for example, in vitro or in vivo. In some embodiments, the effective amount of the compound of formula (I) inhibits the kinase in a cell by 10%, 20%, 30%, 40%, 50%, 60%, 70%, 80%, 90% or 99%, compared to the activity of the kinase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of tyrosine kinase-induced diseases.

The present invention encompasses the use of the compounds of the formula I and/or physiologically acceptable salts and solvates thereof for the preparation of a medicament for the treatment or prevention of rheumatoid arthritis, systemic lupus, asthma, allergic rhinitis, ITP, multiple sclerosis, leukemia, breast cancer and maligna melanoma.

Examples of inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The present invention specifically relates to compounds of the formula I and pharmaceutically acceptable salts, solvates, tautomers and stereoisomers thereof, including mixtures thereof in all ratios,
for the use for the treatment of diseases in which the inhibition, regulation and/or modulation inhibition of Syk plays a role.

The present invention specifically relates to compounds of the formula I and pharmaceutically acceptable salts, solvates, tautomers and stereoisomers thereof, including mixtures thereof in all ratios, for the use for the inhibition of Syk.

The present invention relates to a method of treating a proliferative, autoimmune, anti inflammatory or infectious disease disorder that comprises administering to a subject in need thereof a therapeutically effective amount of a compound of formula I.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bi-calutamide, flutamide, nilutamide and cyproterone acetate), LHRH antago-nists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metallo-proteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro- 4-fluorophenyl)-7-methoxy-6-(3-morpholinopropoxy) quinazolin-4-amine (gefitinib, AZD1839), N-(3-ethynyl-phenyl)-6,7-bis (2-methoxyethoxy)quinazolin-4-amine (erlotinib, OSI-774) and 6-acrylamido-N-(3-chloro-4-fluorophenyl)- 7-(3-morpholinopropoxy)-quinazolin-4-amine (Cl 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide<br>Busulfan<br>Ifosfamide<br>Melphalan<br>Hexamethylmelamine<br>Thiotepa<br>chloroambucil<br>Dacarbazine<br>Carmustine | Lomustine<br>Procarbazine<br>Altretamine<br>Estramustine phosphate<br>Mechloroethamine<br>Streptozocin<br>Temozolomide<br>Semustine |
| Platinum agents | Cisplatin<br>Oxaliplatin<br>Spiroplatin<br>Carboxyphthalatoplatinum<br>Tetraplatin<br>Ormiplatin<br>Iproplatin | Carboplatin<br>ZD-0473 (AnorMED)<br>Lobaplatin (Aetema)<br>Satraplatin (Johnson Matthey)<br>BBR-3464<br>(Hoffmann-La Roche)<br>SM-11355 (Sumitomo)<br>AP-5280 (Access) |
| Anti-metabolites | Azacytidine<br>Gemcitabine<br>Capecitabine<br>5-fluorouracil<br>Floxuridine<br>2-chlorodesoxyadenosine<br>6-Mercaptopurine<br>6-Thioguanine<br>Cytarabine<br>2-fluorodesoxycytidine<br>Methotrexate<br>Idatrexate | Tomudex<br>Trimetrexate<br>Deoxycoformycin<br>Fludarabine<br>Pentostatin<br>Raltitrexed<br>Hydroxyurea<br>Decitabine (SuperGen)<br>Clofarabine (Bioenvision)<br>Irofulven (MGI Pharma)<br>DMDC (Hoffmann-La Roche)<br>Ethynylcytidine (Taiho) |
| Topoiesomeras inhibitors | Amsacrine<br>Epirubicin<br>Etoposide<br>Teniposide or mitoxantrone<br>Irinotecan (CPT-11)<br>7-ethyl-10-hydroxycamptothecin<br>Topotecan<br>Dexrazoxanet (TopoTarget)<br>Pixantrone (Novuspharma)<br>Rebeccamycin analogue (Exelixis)<br>BBR-3576 (Novuspharma) | Rubitecan (SuperGen)<br>Exatecan mesylate (Daiichi)<br>Quinamed (ChemGenex)<br>Gimatecan (Sigma-Tau)<br>Diflomotecan (Beaufour-lpsen)<br>TAS-103 (Taiho)<br>Elsamitrucin (Spectrum)<br>J-107088 (Merck & Co)<br>BNP-1350 (BioNumerik)<br>CKD-602 (Chong Kun Dang)<br>KW-2170 (Kyowa Hakko) |
| Antitumour antibiotics | Dactinomycin (Actinomycin D)<br>Doxorubicin (Adriamycin)<br>Deoxyrubicin<br>Valrubicin<br>Daunorubicin (Daunomycin)<br>Epirubicin<br>Therarubicin<br>Idarubicin<br>Rubidazon<br>Plicamycinp<br>Porfiromycin<br>Cyanomorpholinodoxo-rubicin<br>Mitoxantron (Novantron) | Amonafide<br>Azonafide<br>Anthrapyrazole<br>Oxantrazole<br>Losoxantrone<br>Bleomycin sulfate (Blenoxan)<br>Bleomycinic acid<br>Bleomycin A<br>Bleomycin B<br>Mitomycin C<br>MEN-10755 (Menarini)<br>GPX-100 (Gem Pharmaceuticals) |
| Antimitotic agents | Paclitaxel<br>Docetaxel<br>Colchicine<br>Vinblastine<br>Vincristine<br>Vinorelbine<br>Vindesine<br>Dolastatin 10 (NCI)<br>Rhizoxin (Fujisawa)<br>Mivobulin (Warner-Lambert)<br>Cemadotin (BASF)<br>RPR 109881A (Aventis)<br>TXD 258 (Aventis)<br>Epothilone B (Novartis)<br>T 900607 (Tularik)<br>T 138067 (Tularik)<br>Cryptophycin 52 (Eli Lilly) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTA Medica)<br>ER-86526 (Eisai)<br>Combretastatin A4 (BMS)<br>Isohomohalichondrin-B (PharmaMar)<br>ZD 6126 (AstraZeneca)<br>PEG-Paclitaxel (Enzon)<br>AZ10992 (Asahi)<br>!DN-5109 (Indena) |

TABLE 1-continued

| Category | Column A | Column B |
|---|---|---|
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | Formestan |
| | | YM-511 (Yamanouchi) |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metallo-proteinase inhibitors | Neovastat (Aeterna Laboratories) | CMT-3 (CollaGenex) |
| | Marimastat (British Bio-tech) | BMS-275291 (Celltech) |
| | | Tezacitabine (Aventis) |
| Ribo-nucleoside reductase inhibitors | Gallium maltolate (Titan) | Didox (Molecules for Health) |
| | Triapin (Vion) | |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | | β-Alethin (Dovetail) |
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol chlorotrianisene | Prednisolone |
| | | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | ZDI839 (AstraZeneca) | CEP-751 (Cephalon) |
| | Erlotinib (Oncogene Science) | MLN518 (Millenium) |
| | | PKC412 (Novartis) |
| | Canertjnib (Pfizer) | Phenoxodiol O |
| | Squalamine (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |
| | GW2016 (GlaxoSmithKline) | IMC-1C11 (ImClone) |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | |
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol™ (triclosan mouthwash, Endo) |
| | AG-2037 (GART inhibitor, Pfizer) | Triacetyluridine (uridine prodrug, Wellstat) |
| | WX-UK1 (plasminogen activator inhibitor, Wilex) | SN-4071 (sarcoma agent, Signature BioScience) |
| | PBI-1402 (PMN, stimulant ProMetic LifeSciences) | TransMID-107™ (immunotoxin, KS Biomedix) |
| | Bortezomib (proteasome inhibitor, Millennium) | PCK-3145 (apoptosis promoter, Procyon) |
| | SRL-172 (T-cell stimulant, SR Pharma) | Doranidazole (apoptosis promoter, Pola) |
| | TLK-286 (glutathione-S transferase inhibitor, Telik) | CHS-828 (cytotoxic agent, Leo) |
| | PT-100 (growth factor agonist, Point Therapeutics) | Trans-retinic acid (differentiator, NIH) |
| | Midostaurin (PKC inhibitor, Novartis) | MX6 (apoptosis promoter, MAXIA) |
| | Bryostatin-1 (PKC stimulant, GPC Biotech) | Apomine (apoptosis promoter, ILEX Oncology) |

TABLE 1-continued

| | |
|---|---|
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

The present invention specifically relates to compounds of the formula I and pharmaceutically acceptable salts, solvates, tautomers and stereoisomers thereof, including mixtures thereof in all ratios, for the use for the treatment of rheumatoid arthritis, systemic lupus, asthma, allergic rhinitis, ITP, multiple sclerosis, leukemia, breast cancer, maligna melanoma.

The present invention specifically relates to methods for treating or preventing an inflammatory condition, immunological condition, autoimmune condition, allergic condition, rheumatic condition, thrombotic condition, cancer, infection, neurodegenerative disease, neuroinflammatory disease, cardiovascular disease or metabolic condition, comprising administering to a subject in need thereof an effective amount of a compound of formula I or a pharmaceutically acceptable salt, tautomer, stereoisomer or solvate thereof.

In another aspect provided herein are methods of inhibiting a kinase in a cell expressing said kinase, comprising contacting said cell with an effective amount of a compound of formula I or a pharmaceutically acceptable salt, tautomer, stereoisomer or solvate thereof. In one embodiment the kinase is Syk, FLT3, JAK1 or JAK2 or JAK3 or BTK, or mutants or isoforms thereof, or combinations of two or more thereof.

Representative immunological conditions that compounds of formula I are useful for treating or preventing include, but are not limited to, Behcet's syndrome, non-allergy mast cell diseases (e.g., mastocytosis and treatment of anaphylaxis), ankylosing spondylitis, osteoarthritis, rheumatoid arthritis (RA), multiple sclerosis, lupus, inflammatory bowel disease, ulcerative colitis, Crohn's disease, myasthenia gravis, Grave's disease, transplant rejection, humoral transplant rejection, non-humoral transplant rejection, cellular transplant rejection, immune thrombocytopenic purpura (ITP), idiopathic thrombocytopenic purpura, diabetes, immunological response to bacterial, parasitic, helminth infestation or viral infection, eczema, dermatitis, graft versus host disease, Goodpasture's disease, hemolytic disease of the newborn, autoimmune hemolytic anemia, anti-phospholipid syndrome, ANCA-associated vasculitis, Churg-Strauss syndrome, Wegeners granulomatosus, pemphigus vulgaris, serum sickness, mixed cryoglobulinemia, peripheral neuropathy associated with IgM antibody, microscopic polyangiitis, Hashimoto's thyroiditis, Sjogrens syndrome, fibrosing conditions (such as those dependent on the innate or adaptive immune systems or local mesenchyma cells) or primary biliary cirrhosis.

Representative autoimmune conditions that compounds of formula I are useful for treating or preventing include, but are not limited to, autoimmune hemolytic anemia (A1HA), Behcet's syndrome, Crohn's disease, type I diabetes, Goodpasture's disease, Grave's disease, Hashimoto's thyroiditis, idiopathic thrombocytopenic purpura, lupus, multiple sclerosis, amyotrophic lateral sclerosis, myasthenia gravis, pemphigus vulgaris, primary biliary cirrhosis, rheumatoid arthritis, scleroderma, Sjogren's syndrome, ulcerative colitis, or Wegeners granulomatosus.

Representative allergic conditions that compounds of formula I are useful for treating or preventing include, but are not limited to, anaphylaxis, hay fever, allergic conjunctivitis, allergic rhinitis, allergic asthma, atopic dermatitis, eczema, urticaria, mucosal disorders, tissue disorders and certain gastrointestinal disorders.

Representative rheumatic conditions that compounds of formula I are useful for treating or preventing include, but are not limited to, rheumatoid arthritis, gout, ankylosing spondylitis, or osteoarthritis.

Representative inflammatory conditions that compounds of formula I are useful for treating or preventing include, but are not limited to, non-ANCA (anti-neutrophil cytoplasmic autoantibody) vasculitis (e.g., wherein Syk function is associated with neutrophil adhesion, diapedesis and/or activation), psoriasis, asthma, allergic rhinitis, allergic conjunctivitis, chronic urticaria, hives, anaphylaxis, bronchitis, chronic obstructive pulmonary disease, cystic fibrosis, inflammatory bowel disease, irritable bowel syndrome, gout, Crohn's disease, mucous colitis, ulcerative colitis, allergy to intestinal antigens (such as gluten enteropathy), diabetes (e.g., Type I diabetes and Type II diabetes) and obesity. In some embodiments, the inflammatory condition is a dermatologic condition, such as, for example, psoriasis, urticaria, hives, eczema, scleroderma, or dermatitis. In other embodiments, the inflammatory condition is an inflammatory pulmonary condition, such as, for example, asthma, bronchitis, chronic obstructive pulmonary disease (COPD), or adult/acute respiratory distress syndrome (ARDS). In other embodiments, the inflammatory condition is a gastrointestinal condition, such as, for example, inflammatory bowel disease, ulcerative colitis, Crohn's disease, idiopathic inflammatory bowel disease, irritable bowel syndrome, or spastic colon.

Representative infections that compounds of formula I are useful for treating or preventing include, but are not limited to, bacterial, parasitic, prion, viral infections or helminth infestation.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

Representative metabolic conditions that compounds of formula I are useful for treating or preventing include, but are not limited to, obesity and diabetes (e.g., Type I and II diabetes). In a particular embodiment, provided herein are methods for the treatment or prevention of insulin resistance. In certain embodiments, provided herein are methods for the treatment or prevention of insulin resistance that leads to diabetes (e.g., Type II diabetes). In another embodiment, provided herein are methods for the treatment or prevention of syndrome X or metabolic syndrome. In another embodiment, provided herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., impaired glucose metabolism), cystic fibrosis related diabetes, hemochromatosis and ketosis-resistant diabetes.

Representative neurodegenerative and neuroinflammatory diseases that compounds of formula I are useful for treating or preventing include, but are not limited to, Huntington's disease, Alzheimer's disease, viral (e.g., HIV) or bacterial-associated encephalitis and damage.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

In another embodiment, provided herein are methods for the treatment or prevention of diseases associated with thrombotic events such as but not limited to atherosclerosis, myocardial infarction and ischemic stroke.

The present invention specifically relates to compounds of the formula I and pharmaceutically acceptable salts, solvates, tautomers and stereoisomers thereof, including mixtures thereof in all ratios, for the use for the treatment and/or prevention of inflammatory conditions, immunological conditions, autoimmune conditions, allergic conditions, rheumatic conditions, thrombotic conditions, cancer, infections, neurodegenerative diseases, neuroinflammatory diseases, cardiovascular diseases, and metabolic conditions, the methods comprising administering to a subject in need thereof an effective amount of a compound of claim 1.

Moreover, the present invention specifically relates to compounds for the use for the treatment and/or prevention of cancer, where the cancer to be treated is a solid tumour or a tumour of the blood and immune system.

Moreover, the present invention specifically relates to compounds, for the use for the treatment and/or prevention of cancer, where the where the tumour originates from the group of acute myeloid leukaemia, chronic myeloid leukaemia, acute lymphatic leukaemia and/or chronic lymphatic leukaemia.

Moreover, the present invention specifically relates to compounds, for the use for the treatment and/or prevention of cancer, where the solid tumour originates from the group of tumours of the epithelium, the bladder, the stomach, the kidneys, of head and neck, the esophagus, the cervix, the thyroid, the intestine, the liver, the brain, the prostate, the urogenital tract, the lymphatic system, the stomach, the larynx, the bones, including chondosarcoma and Ewing sarcoma, germ cells, including embryonal tissue tumours, and/or the lung, from the group of monocytic leukaemia, lung adenocarcinoma, small-cell lung carcinomas, pancreatic cancer, glioblastomas, neurofibroma, angiosarcoma, breast carcinoma and/or maligna melanoma.

Moreover, the present invention specifically relates to for the use for the treatment and/or prevention of diseases selected from the group rheumatoid arthritis, systemic lupus, asthma, multiple sclerosis, osteoarthritis, ischemic injury, giant cell arteritis, inflammatory bowel disease, diabetes, cystic fibrosis, psoriasis, Sjogrens syndrome and transplant organ rejection.

Moreover, the present invention specifically relates to compounds for the use for the treatment and/or prevention of diseases selected from the group Alzheimer's disease, Down's syndrome, hereditary cerebral hemorrhage with amyloidosis-Dutch Type, cerebral amyloid angiopathy, Creutzfeldt-Jakob disease, frontotemporal dementias, Huntington's disease, Parkinson's disease.

Moreover, the present invention specifically relates to compounds for the use for the treatment and/or prevention of diseases selected from the group leishmania, mycobacteria, including *M. leprae, M. tuberculosis* and/or *M. avium, leishmania, plasmodium*, human immunodeficiency virus, Epstein Barr virus, Herpes simplex virus, hepatitis C virus.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays

SYK Flash Plate Assay

The kinase assay is performed either as 384-well Flashplate assay (for e.g. Topcount measurement) or as 384-well Image-Flashplate assay (for LEADseeker measurement).

2.5 nM SYK, 400 nM Biotin-Aha-Aha-KEDPDYEWP-SAKK and 10 μM ATP (spiked with 0.3 μCi 33P-ATP/well) are incubated in a total volume of 50 μl (60 mM Hepes, 10 mM $MgCl_2$, 1.2 mM Dithiothreitol, 0.02% Brij35, 0.1% BSA, pH 7.5) with or without test compound for 1 hours at 30° C. The reaction is stopped with 25 μl 200 mM EDTA. After 30 Min at 30° C. the liquid is removed and each well washed thrice with 100 μl 0.9% sodium chloride solution. Non-specific reaction is determined in presence of 0.1 μM Staurosporine. Radioactivity is measured with Topcount (when using Flashplates) or with LEADseeker (when using Image-Flashplates) respectively. Results (e.g. IC50-values) are calculated with program tools provided by the IT-department (e.g. Symyx Assay Explorer, Genedata Screener).

In Vivo Assays

CIA

For induction of collagen-induced arthritis (CIA) male DBA/1 mice are injected with 500 μl pristane i.p. on day-21. On day 0 mice are immunized with 100 μg chicken collagen type II (CII) in Complete Freund's Adjuvant (CFA) intradermally, distributed over pinnae and one site on the back on day 0. On day 21, mice will receive an i.p. booster immunization (100 μg) with soluble CII in PBS. Dosing of Syk inhibitor will be prophylactic: starting day 0 and continued until day 10 and before boost starting on day 20 and continued until day 30. Compounds will be administered orally twice a day at doses of 3, 10 and 30mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

GIA

For induction of Glucose-6-phosphate isomerase-induced arthritis (GIA) female DBA/1 mice are immunized with 100 μg G6PI in Complete Freund's Adjuvant (CFA) intradermally, distributed over pinnae and one site on the back on day 0. Dosing of Syk inhibitor will be prophylactic starting day 0 and continued until day 14. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

HPLC data provided in the examples described below (retention time given) were obtained as follow:

method A: 1 min 99% A, in 2.5 min from 99% A to 100% B, followed by 1.5 min 100% B and 1 min 99% A. Column: Chromolith SpeedRod RP-18e; 50-4.6 mm; detection 220 nM (solvent A: $H_2O$ (0.1% TFA), solvent B: ACN (0.1% TFA).

method F: In 8 min from 98% A to 100% B, within 0.1 min to 98% A, during 1.9 min 98% A (solvent A $H_2O$ (0.1% TFA), solvent B: ACN (0.1% TFA)); column: Xbridge C8 5 μM, 4.6×50 mm; flow rate: 2 mL/min.

method H: 0.2 min 99% A; within 2.6 min from 1% B to 100% B, followed by 0.6 min 100% B and within 0.1 min to 99% A. Column Chromolith Performance RP18e 100-3 mm, flow rate 2 ml/min, detection 220 nM; Solvent A: H2O (0.05% HCOOH), Solvent B: ACN (0.04% HCOOH).

method I: in 9 min from 95% A to 95% B; solvent A: $H_2O$+0.2% TFA, solvent B: CAN+0.2% TFA; column: Chromolith SpeedROD (RP-18e, 50-4.6 mm), detection: 220 nm; flow rate: 2 ml/min.

method J: 0.2 min 99% A, in 3.6 min from 99% A to 100% B, followed by 0.6 min 100% B and 0.4 min 99% A. Column: Chromolith SpeedRod RP-18e; 100-3 mm; detection 220 nM (solvent A: $H_2O$ (0.1% TFA), solvent B: ACN (0.1% TFA)

method K: 0.2 min 99% A, in 3.6 min from 99% A to 100% B, followed by 0.6 min 100% B and 0.4 min 99% A. Column: Waters-Sunfire-C18; 100-3 mm; detection 220 nM (solvent A: $H_2O$ (0.1% TFA), solvent B: ACN (0.1% TFA). Preparative HPLC was performed on a Agilent 1200. Column: Chromolith prep RP 18e Merck KGaA. Mobile phase: 0.1% formic acid in water/0.1% formic acid in acetonitrile.

LCMS data provided in the examples are given with retention time, purity and/or mass in m/z. The results were obtained as followed: mass spectrum: LC/MS Waters ZMD (ESI) or Hewlett Packard System of the HP 1100 series (ion source: electrospray (positive mode); scan: 100-1000 m/z; fragmentation-voltage: 60 V; gas-temperature: 300° C., DAD: 220 nm; flow rate: 2.4 ml/min. The used splitter reduced the flow rate after the DAD for the MS to 0.75 ml/min; column: Chromolith Speed ROD RP-18e 50-4.6; solvent: LiChrosolv-quality from the company Merck KGaA or as mentioned in the method.

method B: A-0.1% HCOOH, B-MeOH: flow-1.0 ml/min.; column: Atlantis C8 (50×4.6 mm 5 Um, +ve mode).

method C: A-10 mM, B— MeOH: flow 1.0 ml/min, column: XBridge C8 (30×2.1 mm 3.5 Um, +ve mode).

method D: A-0.1% TFA in $H_2O$, B-0.1% TFA in ACN: flow-2.0 ml/min; column: XBridge C8 (50×4.6 mm 3.5 Um, +ve mode.

method E: within 2.8 min from 96% C to 100% D, followed by 0.5 min 100% D and within 0.1 min to 96% C; column Chromolith SpeedRod RP-18e; 50-4.6 mm; detection 220 nM; solvent C: $H_2O$ (0.05% HCOOH), solvent D: ACN (0.05% HCOOH).

method G: Within 2.8 min from 96% C to 100% D, followed by 0.5 min 100% D and within 0.1 min to 96% C. Column Chromolith SpeedRod RP-18e; 50-4.6 mm; detection 220 nM; Solvent C: $H_2O$ (0.1% TFA), Solvent D: ACN (0.1% TFA)

$^1$H NMR was recorded on Bruker DPX-300, DRX-400 or AVII-400 spectrometer, using residual signal of deuterated solvent as internal reference. Chemical shifts (δ) are reported in ppm relative to the residual solvent signal (δ=2.49 ppm for 1H NMR in DMSO-$d_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

The microwave chemistry is performed on a single mode microwave reactor Emrys™ Optimiser from Personal Chemistry.

EXAMPLES

General synthetic route for preparation of amino-pyridopyrimidine derivatives:

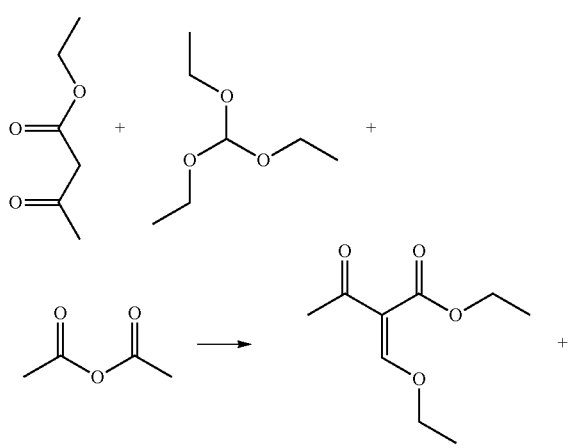

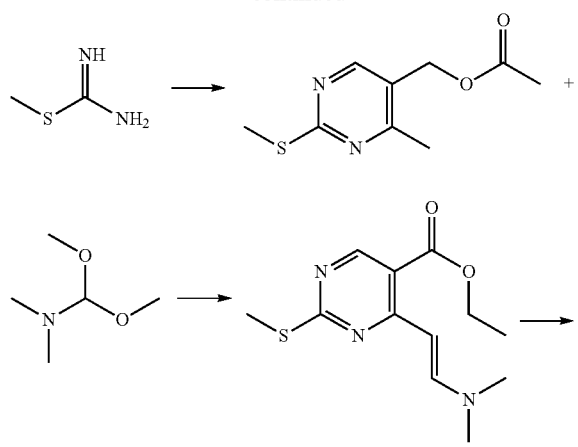

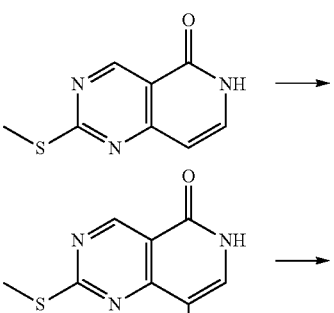

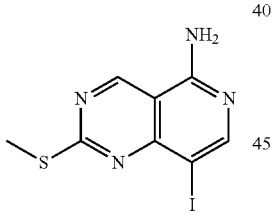

Preparation of intermediates

2-[1-Ethoxy-meth-(Z)-ylidene]-3-oxo-butyric acid ethyl ester

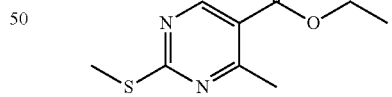

Ethyl acetoacetate (600 ml, 4.75 mol, 1 eq) is treated with triethyl orthoformate (780 ml, 4.74 mol, 1 eq) and acetic anhydride (900 ml, 9.52 mol, 2 eq) at rt. The resulting suspension is heated to 120° C. for 2 h and monitored by IPC. Upon completion, the reaction is cooled to rt and evaporated in vacuo. For further purification the liquid is destillated 84° C.-120° C., 0.7-0.4 mbar) to give the title compound (674 g, 72%) as a light yellow liquid;

HPLC (method I): Rt 2.07 min (purity 94%); LCMS (ESI$^+$) (method E): Rt 1.984 min, M+H$^+$187.1 m/z.

4-Methyl-2-methylsulfanyl-pyrimidine-5-carboxylic acid ethyl ester

2-[1-Ethoxy-meth-(Z)-ylidene]-3-oxo-butyric acid ethyl ester (666 g, 3.58 mol, 1 eq) is dissolved in ethanol (3.5 L, 17 eq), TEA (515 ml, 3.7 mol, 1 eq) and S-methyl-isothiouronium sulfate (560 g, 2.01 mol, 0.6 eq) are added. Under vigorous stirring the reaction is heated to reflux for 2 h. At 0° C. 3 L water are added to the reaction mixture and the black suspension is stirred overnight at rt. The suspension is cooled to 0° C. and suctioned by vacuum. The precipitate is washed with water and dried for 14 h at 35° C. under vacuum giving 612 g (81%) of the title compound as an off-white solid;

HPLC (method I): Rt 3.06 min (purity 99.9%); LCMS (ESI$^+$) (method E): Rt 2.355 min, M+H$^+$212.3 m/z.

4-((E)-2-Dimethylamino-vinyl)-2-methylsulfanyl-pyrimidine-5-carboxylic acid ethyl ester

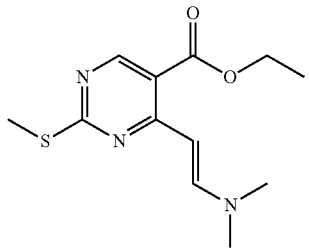 [SMILES: CCOC(=O)c1cnc(SC)nc1/C=C/N(C)C]

4-Methyl-2-methylsulfanyl-pyrimidine-5-carboxylic acid ethyl ester (615 g, 2.9 mol, 1 eq) is suspended in DMF (2.8 L) and N,N-dimethylformamide dimethylacetal (780 ml, 2 eq) is added dropwise. The reaction is heated to reflux for 1.5 h. After completion the reaction mixture is cooled down and suspended in 9 L of an ice/water mixture. A yellow precipitate is suctioned by vacuum. The precipitate is washed with water and dried for 14 h at 40° C. A mixture of E and Z 4-(2-dimethylamino-vinyl)-2-methylsulfanyl-pyrimidine-5-carboxylic acid ethyl ester (745 g, 75%) is obtained as yellow solid; HPLC (method I): Rt 2.767 min (purity 78.3%); LCMS (ESI$^+$) (method E): Rt 2.158 min, M+H$^+$ 268.1 m/z.

2-Methylsulfanyl-6H-pyrido[4,3-d]pyrimidin-5-one

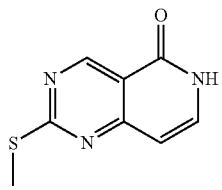

4-((E)-2-Dimethylamino-vinyl)-2-methylsulfanyl-pyrimidine-5-carboxylic acid ethyl ester (316 g, 1.18 mol, 1 eq) is suspended in EtOH (3 L) and ammonium acetate (911 g, 11.82 mol, 10 eq) is added. The orange suspension is heated up to 78° C. After 20 min of reflux an almost clear red solution is obtained which starts to become a red-orange suspension after 1.5 h of reflux. HPLC shows 85% of product. The heating system is switch off and the reaction mixture is allowed to cool down. The red-orange suspension is filtered and washed with ethanol, suspended in 600 ml water and stirred for 60 min. The suspension is filtered and the precipitate is washed with water and 150 ml EtOH. The obtained red-orange crystals are dried in vacuum at 35° C. with under nitrogen flow, to give 174 g (73%) of the title compound;

HPLC (method I): Rt 1.837 min (purity 95.9%); LCMS (ESI$^+$) (method E): Rt 1.437 min, M+H$^+$194 m/z.

8-Iodo-2-methylsulfanyl-6H-pyrido[4,3-d]pyrimidin-5-one

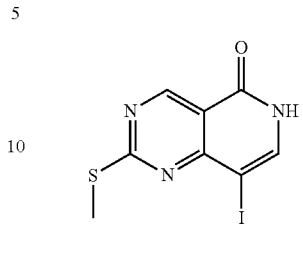

2-Methylsulfanyl-6H-pyrido[4,3-d]pyrimidin-5-one (84 g, 0.42 mol, 1 eq) is dissolved in dry acetonitrile (2.2 L) and potassium carbonate (116 g, 0.84 mol, 2 eq) is added at rt. To the reaction mixture N-iodosuccinimide (118 g, 0.53 mol, 1.3 eq) is added in portions. The resulting suspension is heated to 75° C. for 3 h and monitored by HPLC MS. Upon completion, the reaction is cooled to rt and the precipitate is collected by suction. The precipitate is rinsed with acetonitrile, then suspended in a minimum amount of water and treated by ultra sonification. The solids are again collected by suction and dried in vacuum at 35° C. to give the title compound (115 g, 82%) as pale yellow crystals;

HPLC (method A): Rt 2.48 min (purity 70.1%); LCMS (ESI$^+$) (method G): Rt 1.687 min, M+H$^+$319.9 m/z.

5-Chloro-8-iodo-2-methylsulfanyl-pyrido[4,3-d]pyrimidine

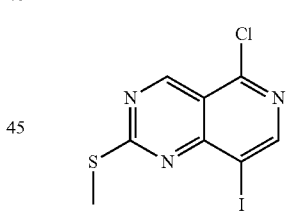

8-Iodo-2-methylsulfanyl-6H-pyrido[4,3-d]pyrimidin-5-one (208 g, 0.63 mol, 1 eq) is suspended in acetonitrile and benzyltriethylammonium chloride (280 g, 1.23 mol, 2 eq) is added. DIPEA (137 ml, 0.81 mol, 1.3 eq) is added to the suspension, followed by slow addition of phosphorylchloride (118 ml, 1.29 mol; 204.62 mol %) within 15 min. The reaction mixture is refluxed for 14 h. The suspension is cooled to 30° C. and slowly poured into 3 L ice water. The resulting brown suspension is stirred for 20 min and filtered. The precipitate is washed with 2 L water, withdrawn by suction and dried at 35° C. under a nitrogen flow. The title compound (201 g, 88%) is obtained as a pale brown solid;

HPLC (method I): Rt 3.853 min (purity 97.8%); LCMS (ESI$^+$) (method E): Rt 2.695 min, M+H$^+$338 m/z.

8-Iodo-2-methylsulfanyl-pyrido[4,3-d]pyrimidin-5-ylamine

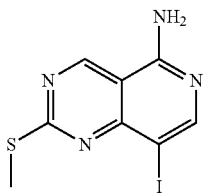

5-Chloro-8-iodo-2-methylsulfanyl-pyrido[4,3-d]pyrimidine (31 g, 85 mmol, 1 eq) suspended in dioxane (220 ml) is treated with an ammonia solution 32% (106 ml, 30 eq) and heated in a closed vessel at 100° C. for 15 minutes. At rt the solids are withdrawn by suction, washed with water and dried for 14 h at 35° C. under vacuum. The title compound (21.2 g, 59%) is obtained as off-white amorphous solid;

HPLC (method A): Rt 2.36 min (purity 82.2%); LCMS (ESI$^+$) (method G): Rt 1.42 min, M+H$^+$318.9 m/z.

8-(1-Methyl-1H-pyrazol-4-yl)-2-methylsulfanyl-pyrido[4,3-d]pyrimidin-5-ylamine

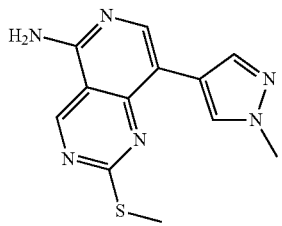 [SMILES: CSc1ncc2c(N)ncc(-c3cnn(C)c3)c2n1]

Process A:

A microwave vial is charged with 8-iodo-2-methylsulfanyl-pyrido[4,3-d]pyrimidin-5-ylamine (1 eq.), 1-methylpyrazole-4-boronic acid (1.50 eq.), palladium(II)-acetate (47% Pd) (5 mol %.), 2-dicyclohexylphosphino-2',6'-dimethoxybiphenyl (10 mol-%.), potassium carbonate (3 eq.), ethylenglycoldimethylether (1 mL/mmol.), water (0.5 ml/mmol) and is degassed for 5 min. The suspension is heated at 150° C. for 45 min under microwave irradiation and monitored via HPLC MS. Upon completion, the suspension is cooled to rt, filtered over a pad of Celite and washed with methanol. The filtrate is concentrated in vacuo. The crude material is purified by flash chromatography. The title compound (99% yield) is obtained as an orange solid.

N2-((cis)-2-Amino-cyclohexyl)-8-(1-methyl-1H-pyrazol-4-yl)-pyrido[4,3-d]-pyrimidine-2,5-diamine ("A1")

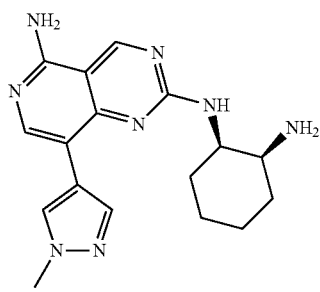 [SMILES: Cn1cc(-c2cnc(N)c3cnc(N[C@@H]4CCCC[C@@H]4N)nc23)cn1]

8-(1-Methyl-1H-pyrazol-4-yl)-2-methylsulfanyl-pyrido [4,3-d]pyrimidin-5-ylamine (245 mg, 0.68 mmol, 1 eq) is treated with cis-1,2-cyclohexanediamine (824 µl, 6.8 mmol, 10 eq) and stirred for 5.5 h at 150° C. The mixture is cooled to rt, diluted with acetonitrile and purified via prep. HPLC to give the title compound (180 mg, 78%) as a brown solid.

One obtains the mixture of the two cis-enantiomers.

The enantiomers are separated via chiral HPLC.

Enantiomer 1 (the compound which eluates first from the column):

HPLC (method A): Rt 2.24 min (purity 98%); LCMS (ESI+) (method G): Rt 1.243 min., MH+339.20; HCl salt: $^1$H NMR (500 MHz, DMSO-d$_6$) δ [ppm] 9.35-9.23 (m, 1H), 8.60-8.37 (m, 1H), 8.34-8.21 (m, 2H), 8.08-7.97 (m, 1H), 7.29-7.03 (m, 1H), 7.00-6.86 (m, 2H), 6.52-6.43 (m, 1H), 3.98-3.90 (m, 1H), 3.86 (s, 3H), 3.19-3.13 (m, 1H), 2.55 (q, J=7.1, 2H), 1.72-1.63 (m, 2H), 1.62-1.54 (m, 2H), 1.42-1.31 (m, 2H).

General synthetic route for preparation of des-amino-pyridopyrimidine derivatives:

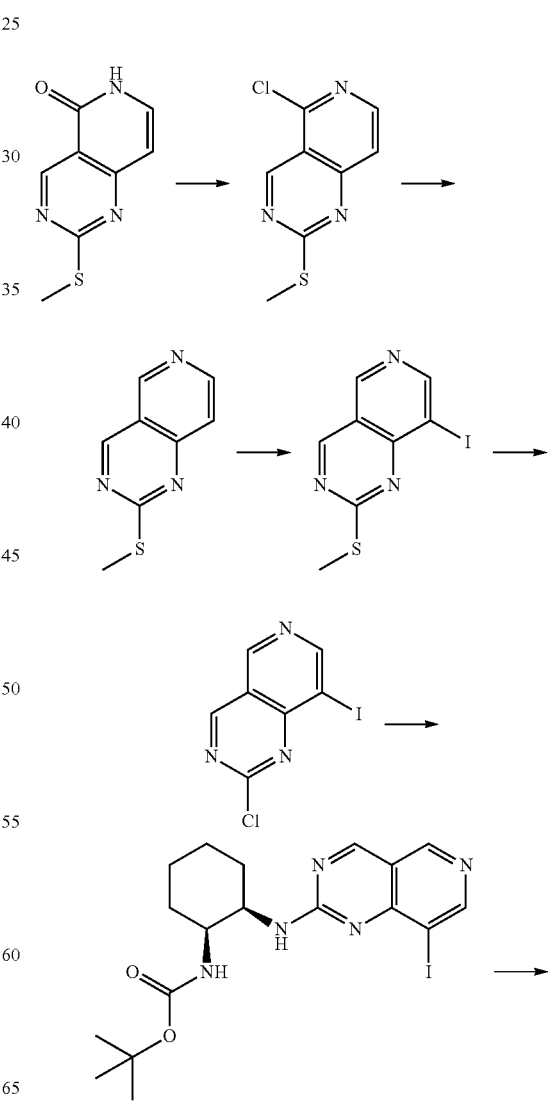

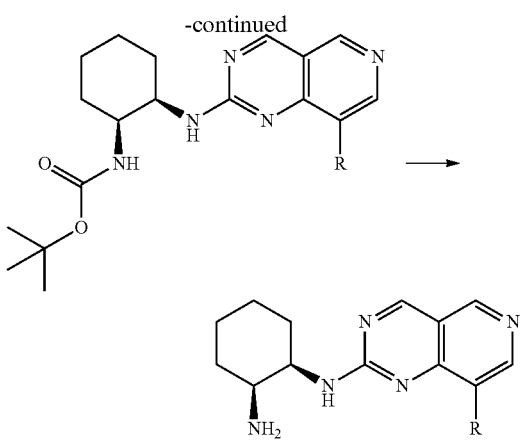

→

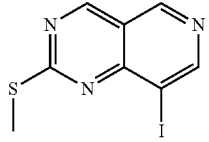

Preparation of intermediates

5-Chloro-2-methylsulfanyl-pyrido[4,3-d]pyrimidine

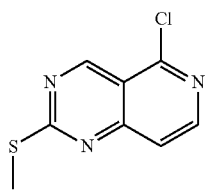

2-Methylsulfanyl-6H-pyrido[4,3-d]pyrimidin-5-one (72 g, 0.37 mol, 1 eq) is suspended in phosphorylchloride (420 ml) and refluxed for 1.5 h. At rt the reaction mixture is evaporated in vacuo. To the residue is added 450 ml of ice water and stirred for a while. The solid is filtered by vacuum and dried for 14 h at 40° C. under vacuum. The title compound (54 g, 63%) is obtained as a light brown solid;

HPLC (method A): Rt 2.57 min (purity 98.7%); LCMS (ESI⁺) (method G): Rt 1.95 min, M+H⁺212.1 m/z.

2-Methylsulfanyl-pyrido[4,3-d]pyrimidine

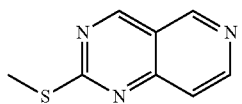

A microwave vial is charged with 5-chloro-2-methylsulfanyl-pyrido[4,3-d]-pyrimidine (1 g, 4.66 mmol, 1 eq) dissolved in MeOH (18 ml) and palladium-activated carbon (10% Pd, 452 mg, 0.42 mmol, 0.1 eq), ammonium formate (606 mg, 9.33 mmol, 2 eq) are added. The suspension is heated twice at 100° C. for 1 h under microwave irradiation and monitored by HPLC. Upon completion, the suspension is cooled to rt, filtered over a pad of Celite by suction and the solvent is removed in vacuum. The precipitate is dissolved in DCM/MeOH, absorbed on silica gel and purified by flash chromatography (n-heptane→n-heptane/ethyl acetate 1:3) yielding title compound (826 mg, 54%) as white solid;

HPLC (method A): Rt 2.15 min (purity 100%); LCMS (ESI⁺) (method G): Rt 1.06 min, M+H⁺178.1 m/z.

8-Iodo-2-methylsulfanyl-pyrido[4,3-d]pyrimidine

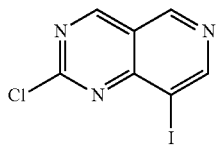 [SMILES: Clc1ncc2cncc(I)c2n1]

2-Methylsulfanyl-pyrido[4,3-d]pyrimidine (17 g, 96 mmol, 1 eq.) are suspended in N,N-dimethylformamide (340 ml, 4.37 mol, 46 eq.). Trifluoroacetic acid (9 ml, 115 mmol, 1.2 eq.) and N-iodosuccinimide (22 g, 97 mmol, 1 eq.) are added to the reaction mixture and stirred at 50° C. for 4 d. Another portion of NIS (4.3 g, 19 mmol, 0.2 eq) is added and stirring at 50° C. is continued for 3 d. Upon completion the reaction mixture is poured into water and diluted sodium thiosulphate solution is added. After 20 min the suspension turned violet. The solids are filtered by suction, washed with water. The residue is dissolved, transferred in a round bottom flask and concentrated in vacuo. The residue is further dried under vacuum to yield the title compound (30 g, 85%) as yellow solid;

HPLC (method A): Rt 2.60 min (purity 100%); LCMS (ESI⁺) (method G): Rt 2.02 min, M+H⁺304 m/z.

2-Chloro-8-iodo-pyrido[4,3-d]pyrimidine

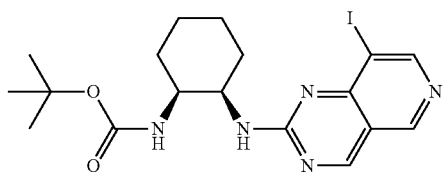 [SMILES: CC(C)(C)OC(=O)N[C@H]1CCCC[C@H]1Nc1ncc2cncc(I)c2n1]

8-Iodo-2-methylsulfanyl-pyrido[4,3-d]pyrimidine (2.40 g, 7.34 mmol, 1 eq.) is suspended in acetonitrile (56.00 ml). At 0° C. DCM (72 ml, 1.13 mol, 153 eq.) is added which turned the suspension in a clear solution. Sulfuryl chloride (6 ml, 73.40 mmol, 10 eq.) is added which results in an immediate precipitation. The suspension is stirred for 2 h at 0° C. The precipitate is filtered, washed with acetonitrile and dried under vacuum at 50° C. for 1 h. 2-Chloro-8-iodo-pyrido-[4,3-d]pyrimidine (1.86 g; 6.38 mmol) is obtained as an orange solid; HPLC (method A): Rt 2.45 min (purity 100%); LCMS (ESI⁺) (method G): Rt 1.75 min, M+H⁺291.9 m/z.

[(1S,2R)-2-(8-Iodo-pyrido[4,3-d]pyrimidin-2-ylamino)-cyclohexyl]-carbamic acid tea-butyl ester 2-Chloro-8-iodo-pyrido[4,3-d]pyrimidine (2.26 g, 7.24 mmol, 1 eq.) is dissolved in triethylamine (1.51 ml, 10.86 mmol, 1.5 eq.) and ethanol (4.82 ml, 82.68 mmol, 11.4 eq.). ((1S,2R)-2-Amino-cyclohexyl)-carbamic acid tert-butyl ester (1.86 g, 8.69 mmol, 1.2 eq.) is added to the reaction mixture which is heated for 5 min at 120° C. in a microwave reactor. The reaction mixture is evaporated in vacuo, dissolved in ethyl acetate and sonicated. The solids (triethylammonium chloride) are withdrawn by suction. The filtrate is evaporated in vacuo. The obtained residue is suspended in acetonitrile, sonicated and filtered by suction to remove byproducts. Again, the filtrate is evaporated in vacuo. The obtained residue is dissolved in ethyl acetate and filtered over a plug of amino functionalized silica gel. The filtrate is evaporated in vacuo to give the title compound (2.17 g, 50%) as orange solid; HPLC (method A): Rt 2.49 min (purity 99.6%); LCMS (ESI$^+$) (method G): Rt 1.95 min, M+H$^+$470.1 m/z.

{(1S,2R)-2-[8-(1-Methyl-1H-pyrazol-4-yl)-pyrido[4,3-d]pyrimidin-2-ylamino]-cyclohexyl}-carbamic acid tert-butyl ester

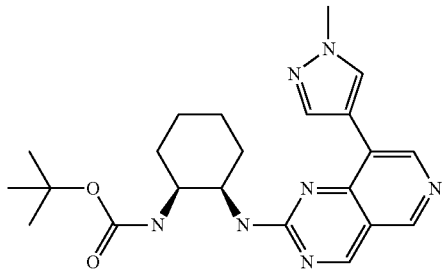 [SMILES: Cn1cc(-c2cncc3cnc(N[C@@H]4CCCC[C@@H]4NC(=O)OC(C)(C)C)nc23)cn1]

The Suzuki coupling is performed by reacting [(1S,2R)-2-(8-iodo-pyrido[4,3-d]pyrimidin-2-ylamino)-cyclohexyl]-carbamic acid tert-butyl ester with 1-methylpyrazole-4-boronic acid analogously to "process A". The title compound (41.6% yield) is obtained as yellow solid.

(1R,2S)—N-[8-(1-Methyl-1H-pyrazol-4-yl)-pyrido[4,3-d]pyrimidin-2-yl]-cyclohexane-1,2-diamine hydrochloride ("A2")

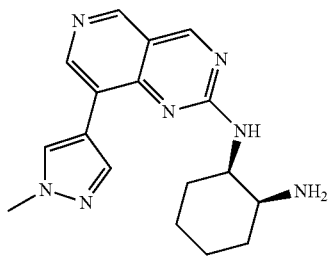 [SMILES: Cn1cc(-c2cncc3cnc(N[C@@H]4CCCC[C@@H]4N)nc23)cn1]

{(1S,2R)-2-[8-(1-Methyl-1H-pyrazol-4-yl)-pyrido[4,3-d]pyrimidin-2-ylamino]-cyclohexyl}-carbamic acid tert-butyl ester (18.8 mg, 0.044 mmol, 1 eq.) is dissolved in ethyl acetate (1.0 ml) and HCl solution (1 N, 222 µl, 0.222 mmol, 5 eq.) are added. The reaction mixture is vigorously stirred for 4 h at 40° C. Ethyl acetate is removed by a nitrogen flow. The remaining aqueous solution is diluted with water and lyophylized to give the title compound (15 mg, 94%) as yellow solid;

HPLC (method A): Rt 2.28 min (purity 100.0%); LCMS (ESI$^+$) (method G): Rt 1.21 min, M+H$^+$324.3 m/z;

HPLC (method A): Rt 2.28 min (purity 100%); LCMS (ESI+) (Method G): Rt 1.241 min., MH+324.20; HCl salt: $^1$H NMR (500 MHz, DMSO-d$_6$) δ [ppm] 9.66-9.54 (m, 1H), 9.44-9.29 (m, 1H), 9.29-9.00 (m, 1H), 8.98 (s, 1H), 8.70-8.45 (m, 1H), 8.34 (s, 1H), 8.27-8.17 (m, 2H), 4.56-4.49 (m, 1H), 3.97 (s, 3H), 3.76 (s, 1H), 2.11-1.94 (m, 2H), 1.84-1.62 (m, 4H), 1.57-1.41 (m, 2H).

Analogous reaction gives the following compounds:

| nr. | name and/or structure |
|---|---|
| "A3" | N2-(cis-2-Amino-cyclohexyl)-8-(3-[1,2,3]triazol-2-yl-phenyl)-pyrido[4,3-d]pyrimidine-2,5-diamine 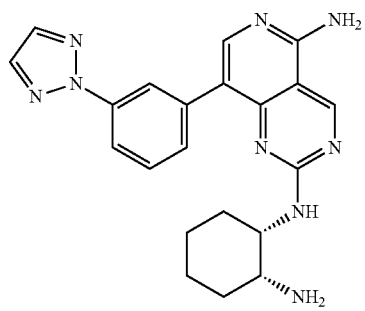 [SMILES: Nc1ncc(-c2cccc(-n3nccn3)c2)c2nc(N[C@H]3CCCC[C@H]3N)ncc12] HPLC (method A): Rt 2.31 min (purity 100%); LCMS (ESI+) (method G): Rt 1.350 min., MH+ 402.20; HCl salt: $^1$H NMR (400 MHz, DMSO-d$_6$) δ [ppm] 9.70 (s, 1H), 9.14 (s, 1H), 8.96-8.87 (m, 1H), 8.55-8.33 (m, 3H), 8.19 (s, 1H), 8.02-8.02 (m, 1H), 7.99-7.90 (m, 2H), 7.82-7.75 (m, 1H), 7.74-7.66 (m, 2H), 3.58-3.45 (m, 2H), 1.88-1.61 (m, 4H), 1.60-1.50 (m, 2H), 1.48-1.35 (m, 1H), 1.33-1.16 (m, 1H) |
| "A4" | N2-((cis)-2-Amino-cyclohexyl)-8-(1-methyl-1H-pyrazol-4-yl)-pyrido[4,3-d]pyrimidine-2,5-diamine 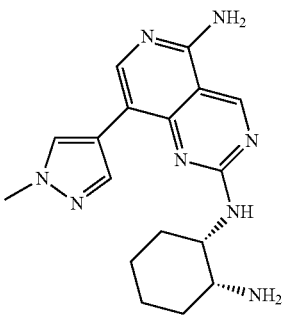 [SMILES: Cn1cc(-c2cnc(N)c3cnc(N[C@H]4CCCC[C@H]4N)nc23)cn1] Enantiomer 2 (the compound which eluates second from the column) HPLC (method A): Rt 2.27 min (purity 98%); LCMS (ESI+) (method G): Rt 1.271 min., MH+ 339.20; HCl salt: $^1$H NMR (500 MHz, DMSO-d$_6$) δ [ppm] 9.35-9.23 (m, 1H), 8.60-8.37 (m, 1H), 8.34-8.21 (m, 2H), 8.08-7.97 (m, 1H), 7.29-7.03 (m, 1H), 7.00-6.86 (m, 2H), 6.52-6.43 (m, 1H), 3.98-3.90 (m, 1H), 3.86 (s, 3H), 3.19-3.13 (m, 1H), 2.55 (q, J = 7.1, 2H), 1.72-1.63 (m, 2H), 1.62-1.54 (m, 2H), 1.42-1.31 (m, 2H) |

| nr. | name and/or structure |
|---|---|
| "A5" | {1-[5-Amino-8-(1-methyl-1H-pyrazol-4-yl)-pyrido[4,3-d]pyrimidin-2-yl]-piperidin-4-yl}-methanol |

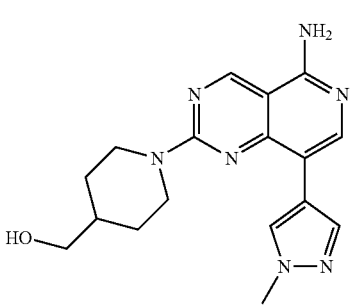 [SMILES: Cn1cc(-c2cnc(N)c3cnc(N4CCC(CO)CC4)nc23)cn1]

HPLC (Method J): Rt 1.82 min (purity 97%); LCMS (ESI+) (Method G): Rt 1.363 min., MH+ 340.20:
$^1$H NMR (500 MHz, DMSO-$d_6$) δ [ppm] 9.33 (s, 1H), 8.23 (s, 1H), 8.15 (s, 1H), 7.97 (s, 1H), 6.99 (s, 2H), 4.89-4.75 (m, 2H), 4.47 (s, 1H), 3.87 (s, 3H), 3.32-3.26 (m, 2H), 3.00 (td, J = 12.7, 2.7, 2H), 1.85-1.76 (m, 2H), 1.73 (td, J = 6.4, 3.5, 1H), 1.21-1.08 (m, 2H)

| nr. | name and/or structure |
|---|---|
| "A6" | N2-(2-Amino-ethyl)-8-(1-methyl-1H-pyrazol-4-yl)-pyrido[4,3-d]-pyrimidine-2,5-diamine |

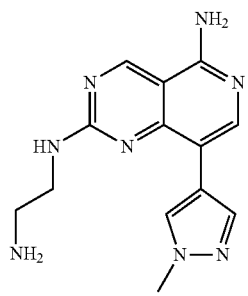 [SMILES: Cn1cc(-c2cnc(N)c3cnc(NCCN)nc23)cn1]

HPLC (method A): Rt 2.20 min (purity 100%); LCMS (ESI+) (method G): Rt 1.060 min., MH+ 285.20;
HCl salt: $^1$H NMR (500 MHz, DMSO-$d_6$) δ [ppm] 9.73-9.57 (m, 1H), 9.05-8.76 (m, 2H), 8.68-8.59 (m, 1H), 8.33 (s, 1H), 8.15-8.05 (m, 3H), 8.03 (s, 1H), 3.96-3.88 (m, 3H), 3.75 (q, J = 6.1, 2H), 3.18-3.10 (m, 1H), 3.10-3.03 (m, 1H)

| nr. | name and/or structure |
|---|---|
| "A7" | N2-(cis-2-Amino-cyclohexyl)-8-(4-tert-butyl-phenyl)-pyrido[4,3-d]pyrimidine-2,5-diamine |

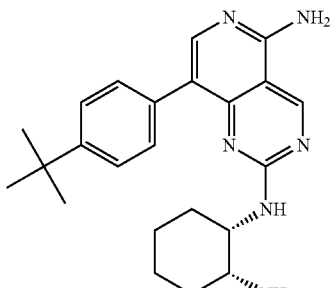

HPLC (method J): Rt 2.236 min (purity 100%); LCMS (ESI+) (method G): Rt 1.790 min., MH+ 391.30

| nr. | name and/or structure |
|---|---|
| "A8" | N2-(cis-2-Amino-cyclohexyl)-8-(1-isobutyl-1H-pyrazol-4-yl)-pyrido[4,3-d]pyrimidine-2,5-diamine |

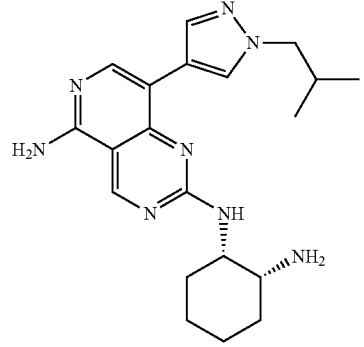 [SMILES: CC(C)Cn1cc(-c2cnc(N)c3cnc(N[C@H]4CCCC[C@H]4N)nc23)cn1]

HPLC (method J): Rt 1.89 min (purity 97%); LCMS (ESI+) (method G): Rt 1.526 min., MH+ 381.30;
HCl salt: $^1$H NMR (500 MHz, DMSO-$d_6$) δ [ppm] 9.74-9.66 (m, 1H), 9.05-8.94 (m, 2H), 8.49 (d, J = 7.3, 1H), 8.37 (s, 1H), 8.33-8.26 (m, 1H), 8.22-8.12 (m, 3H), 8.05 (s, 1H), 4.48-4.40 (m, 1H), 4.03-3.96 (m, 2H), 3.66-3.60 (m, 1H), 2.22-2.11 (m, 1H), 2.06-1.88 (m, 2H), 1.82-1.58 (m, 4H), 1.49-1.41 (m, 2H), 0.90-0.84 (m, 6H)

| nr. | name and/or structure |
|---|---|
| "A9" | 5-Amino-2-(cis2-amino-cyclohexylamino)-pyrido[4,3-d]pyrimidine-8-carbonitrile |

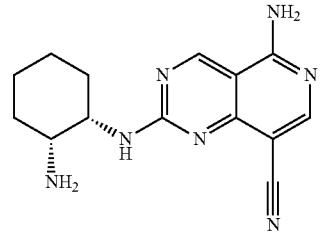 [SMILES: N#Cc1cnc(N)c2cnc(N[C@H]3CCCC[C@H]3N)nc12]

HPLC (method J): Rt 1.526 min (purity 56%); LCMS (ESI+) (method G): Rt 1.209 min., MH+ 284.10;
formate salt: $^1$H NMR (500 MHz, DMSO-$d_6$) δ [ppm] 9.39-9.28 (m, 1H), 8.38 (s, 1H), 8.32-7.90 (m, 4H), 7.89-7.78 (m, 1H), 7.78-7.54 (m, 1H), 4.15 (s, 1H), 3.41-3.36 (m, 1H), 1.88-1.71 (m, 2H), 1.68-1.51 (m, 4H), 1.42-1.31 (m, 2H)

| nr. | name and/or structure |
|---|---|
| "A10" | N2-(cis-2-Amino-cyclohexyl)-8-(1H-indol-2-yl)-pyrido[4,3-d]pyrimidine-2,5-diamine |

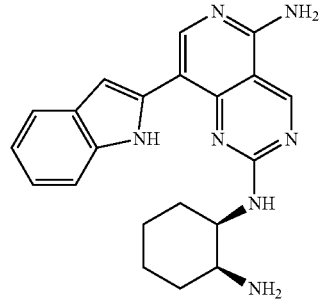 [SMILES: Nc1ncc(-c2cc3ccccc3[nH]2)c2nc(N[C@@H]3CCCC[C@@H]3N)ncc12]

HPLC (method A): Rt 2.40 min (purity 100%); LCMS (ESI+) (method G): Rt 1.636 min., MH+ 374.20:
$^1$H NMR (500 MHz, DMSO-$d_6$) δ [ppm] 1.62 (s, 1H), 9.35 (s, 1H), 8.62 (s, 1H), 7.63-7.50 (m, 1H), 7.50-7.34 (m, 3H), 7.34-7.09 (m, 3H), 7.08-6.90 (m, 3H), 4.10-4.02 (m, 1H), 3.27-3.20 (m, 1H), 1.87-1.27 (m, 8H)

| nr. | name and/or structure |
|---|---|
| "A11" | 2-((cis)-3-Methyl-octahydro-benzoimidazol-1-yl)-8-(1-methyl-1H-pyrazol-4-yl)-pyrido[4,3-d]pyrimidin-5-ylamine Enantiomer 2 (the compound which eluates second from the column)
HPLC (method A): Rt 2.28 min (purity 100%); LCMS (ESI+) (method G): Rt 1.221 min., MH+ 365.20:
$^1$H NMR (500 MHz, DMSO-$d_6$) δ [ppm] 9.33 (d, J = 6.4, 1H), 8.48-8.25 (m, 2H), 8.24 (s, 1H), 8.09-7.95 (m, 1H), 7.09-6.91 (m, 2H), 4.79-4.68 (m, 1H), 4.27-4.16 (m, 1H), 3.89-3.83 (m, 3H), 3.34-3.27 (m, 3H), 2.36-2.24 (m, 3H), 2.20-1.89 (m, 2H), 1.73-1.50 (m, 2H), 1.48-1.19 (m, 4H) |
| "A12" | N2-(cis2-Amino-cyclohexyl)-8-methyl-pyrido[4,3-d]pyrimidine-2,5-diamine HPLC (method A): Rt 2.24 min (purity 94%); LCMS (ESI+) (method G): Rt 1.295 min., MH+ 273.20; HCl salt |
| "A13" | N2-((cis)-2-Amino-cyclohexyl)-8-(4-trifluoromethoxy-phenyl)-pyrido[4,3-d]pyrimidine-2,5-diamine Enantiomer 1 (the compound which eluates first from the column)
HPLC (method A): Rt 2.40 min (purity 99%); LCMS (ESI+) (method G): Rt 1.715 min., MH+ 419.20;
HCl salt: $^1$H NMR (500 MHz, DMSO-$d_6$) δ [ppm] 9.68 (s, 1H), 9.15 (s, 2H), 8.46 (d, J = 6.4, 1H), 8.05 (s, 1H), 8.04-7.95 (m, 2H), 7.83-7.75 (m, 2H), 7.46 (d, J = 8.2, 2H), 4.05-3.96 (m, 1H), 3.63-3.56 (m, 1H), 1.93-1.77 (m, 2H), 1.72-1.50 (m, 4H), 1.45-1.30 (m, 2H) |
| "A14" | N2-((cis)-2-Amino-cyclohexyl)-8-(4-trifluoromethoxy-phenyl)-pyrido[4,3-d]pyrimidine-2,5-diamine Enantiomer 2 (the compound which eluates second from the column)
HPLC (method A): Rt 2.40 min (purity 99%); LCMS (ESI+) (method G): Rt 1.712 min., MH+ 419.20;
HCl salt: $^1$H NMR (500 MHz, DMSO-$d_6$) δ [ppm] 9.68 (s, 1H), 9.15 (s, 2H), 8.46 (d, J = 6.4, 1H), 8.05 (s, 1H), 8.04-7.95 (m, 2H), 7.83-7.75 (m, 2H), 7.46 (d, J = 8.2, 2H), 4.05-3.96 (m, 1H), 3.63-3.56 (m, 1H), .93-1.77 (m, 2H), 1.72-1.50 (m, 4H), 1.45-1.30 (m, 2H) |
| "A15" | {1-[5-Cyclopropylamino-8-(1-methyl-1H-pyrazol-4-yl)-pyrido[4,3-d]pyrimidin-2-yl]-piperidin-4-yl}-methanol HPLC (method J): Rt 1.94 min (purity 100%); LCMS (ESI+) (method G): Rt 1.515 min., MH+ 380.20; HCl salt |
| "A16" | {1-[5-Diethylamino-8-(1-methyl-1H-pyrazol-4-yl)-pyrido[4,3-d]pyrimidin-2-yl]-piperidin-4-yl}-methanol HPLC (method J): Rt 2.03 min (purity 100%); LCMS (ESI+) (method G): Rt 1.588 min., MH+ 396.30; HCl salt |

| nr. | name and/or structure |
|---|---|
| "A17" | N2-((1R,2S)-2-Amino-cyclohexyl)-8-phenyl-pyrido[4,3-d]-pyrimidine-2,5-diamine |

HPLC (method A): Rt 2.32 min (purity 96%); LCMS (ESI+) (method G): Rt 1.468 min., MH+ 335.20;
$^1$H NMR (500 MHz, DMSO-$d_6$) δ [ppm] 9.37 (s, 1H), 8.12 (s, 1H), 7.85-7.58 (m, 2H), 7.43 (t, J = 7.6, 2H), 7.36-7.29 (m, 1H), 7.27-7.19 (m, 1H), 7.17-7.07 (m, 4H), 3.83 (s, 1H), 3.17-3.10 (m, 1H), 1.78-1.45 (m, 6H), 1.43-1.22 (m, 2H)

| "A18" | N2-(cis-2-Amino-cyclohexyl)-8-(7-methoxy-1H-indol-2-yl)-pyrido[4,3-d]pyrimidine-2,5-diamine |

HPLC (method A): Rt 2.39 min (purity 100%); LCMS (ESI+) (method G): Rt 1.669 min., MH+ 404.20;
formate salt: $^1$H NMR (500 MHz, DMSO-$d_6$) δ [ppm] 11.44 (s, 1H), 9.55 (s, 1H), 8.57 (s, 1H), 8.43-8.02 (m, 2H), 7.98-7.73 (m, 3H), 7.14 (d, J = 7.6, 2H), 6.95 (t, J = 7.8, 1H), 6.69 (d, J = 7.7, 1H), 4.46-4.39 (m, 1H), 3.96 (s, 3H), 3.73 (s, 1H), 2.04-1.87 (m, 2H), 1.85-1.74 (m, 2H), 1.73-1.61 (m, 2H), 1.57-1.45 (m, 2H)

| "A19" | N2-(cis-2-Amino-cyclohexyl)-8-(5-methoxy-1H-indol-2-yl)-pyrido[4,3-d]pyrimidine-2,5-diamine |

HPLC (method A): Rt 2.36 min (purity 98%); LCMS (ESI+) (method G): Rt 1.591 min., MH+ 404.30;
$^1$H NMR (500 MHz, DMSO-$d_6$) δ [ppm] 11.80 (s, 1H), 11.52 (s, 1H), 9.35 (s, 1H), 8.58 (s, 1H), 7.63-7.53 (m, 1H), 7.48-7.35 (m, 1H), 7.32-7.16 (m, 3H), 7.03-6.92 (m, 2H), 6.74-6.65 (m, 1H), 4.09-4.01 (m, 1H), 3.76 (s, 3H), 3.24-3.19 (m, 1H), 1.88-1.54 (m, 6H), 1.50-1.31 (m, 2H)

| nr. | name and/or structure |
|---|---|
| "A20" | N2-((R)-2-Amino-3-methoxy-propyl)-8-(1-methyl-1H-pyrazol-4-yl)-pyrido[4,3-d]pyrimidine-2,5-diamine |

HPLC (method J): Rt 1.51 min (purity 100%); LCMS (ESI+) (method G): Rt 1.146 min., MH+ 329.20;
HCl salt: $^1$H NMR (500 MHz, DMSO-$d_6$) δ [ppm] 9.89-9.58 (m, 1H), 8.64-8.54 (m, 1H), 8.49-7.99 (m, 3H), 4.39-4.06 (m, 1H), 4.03-3.94 (m, 3H), 3.91-3.70 (m, 2H), 3.68-3.56 (m, 2H), 3.44-3.32 (m, 3H)

| "A21" | N2-((cis)-2-Amino-cyclohexyl)-8-m-tolyl-pyrido[4,3-d]pyrimidine-2,5-diamine |

Enantiomer 1 (the compound which eluates first from the column)
HPLC (method A): Rt 2.33 min (purity 98%); LCMS (ESI+) (method G): Rt 1.542 min., MH+ 349.20;
HCl salt: $^1$H NMR (500 MHz, DMSO-$d_6$) δ [ppm] 9.66 (s, 1H), 9.21-8.87 (m, 1H), 8.52 (s, 1H), 8.40 (d, J = 6.5, 1H), 8.01-7.92 (m, 3H), 7.50-7.42 (m, 2H), 7.34 (t, J = 7.6, 1H), 7.25-7.18 (m, 1H), 4.06-3.97 (m, 1H), 3.63-3.55 (m, 1H), 2.95-2.86 (m, 2H), 2.38 (s, 3H), 1.94-1.85 (m, 2H), 1.65-1.56 (m, 2H), 1.44-1.32 (m, 2H)

| "A22" | N2-((cis)-2-Amino-cyclohexyl)-8-m-tolyl-pyrido[4,3-d]pyrimidine-2,5-diamine |

Enantiomer 2 (the compound which eluates second from the column)
HPLC (method A): Rt 2.33 min (purity 99%); LCMS (ESI+) (method G): Rt 1.541 min., MH+ 349.30;
HCl salt: $^1$H NMR (500 MHz, DMSO-$d_6$) δ [ppm] 9.66 (s, 1H), 9.21-8.87 (m, 1H), 8.52 (s, 1H), 8.40 (d, J = 6.5, 1H), 8.01-7.92 (m, 3H), 7.50-7.42 (m, 2H), 7.34 (t, J = 7.6, 1H), 7.25-7.18 (m, 1H), 4.06-3.97 (m, 1H), 3.63-3.55 (m, 1H), 2.95-2.86 (m, 2H), 2.38 (s, 3H), 1.94-1.85 (m, 2H), 1.65-1.56 (m, 2H), 1.44-1.32 (m, 2H)

| nr. | name and/or structure |
|---|---|
| "A23" | 2-[5-Amino-2-((cis)-2-amino-cyclohexylamino)-pyrido[4,3-d]-pyrimidin-8-yl]-1H-indole-5-carbonitrile |

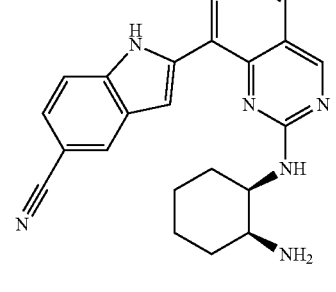

HPLC (method A): Rt 2.37 min (purity 100%); LCMS (ESI+) (method G): Rt 1.657 min., MH+ 399.20
$^1$H NMR (500 MHz, DMSO-d$_6$) δ [ppm] 12.18 (s, 1H), 9.47-9.26 (m, 2H), 8.66-8.54 (m, 1H), 7.98-7.91 (m, 1H), 7.75-7.62 (m, 1H), 7.59-7.50 (m, 1H), 7.48-7.40 (m, 1H), 7.39-7.33 (m, 2H), 7.28-7.21 (m, 2H), 4.10-4.03 (m, 1H), 3.96 (s, 1H), 1.79-1.65 (m, 2H), 1.50-1.33 (m, 2H), 1.09-0.87 (m, 4H)

| "A24" | N2-(cis-2-Amino-cyclohexyl)-8-(1H-indol-3-yl)-pyrido[4,3-d]pyrimidine-2,5-diamine |

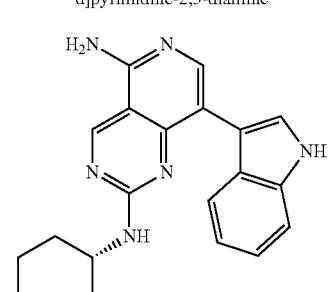

HPLC (method J): Rt 1.93 min (purity 89%); LCMS (ESI+) (method G): Rt 1.560 min., MH+ 374.20;
HCl salt: $^1$H NMR (500 MHz, DMSO-d$_6$) δ [ppm] 12.94 (s, 1H), 11.49 (s, 1H), 9.66 (s, 1H), 9.01-8.90 (m, 1H), 8.43 (d, J = 6.7, 1H), 8.07 (s, 1H), 7.98-7.82 (m, 4H), 7.68-7.63 (m, 1H), 7.48 (d, J = 8.0, 1H), 7.20-7.13 (m, 1H), 7.13-7.06 (m, 1H), 4.13-4.06 (m, 1H), 3.54-3.48 (m, 1H), 1.91-1.68 (m, 2H), 1.66-1.58 (m, 2H), 1.57-1.41 (m, 1H), 1.38-1.26 (m, 3H)

| "A25" | cis-N-[8-(1,3-Dimethyl-1H-pyrazol-4-yl)-pyrido[4,3-d]pyrimidin-2-yl]-cyclohexane-1,2-diamine |

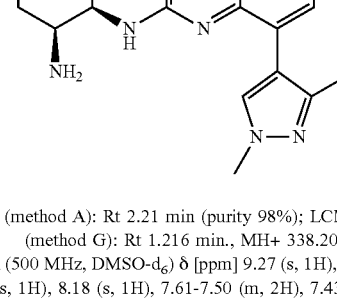

HPLC (method A): Rt 2.21 min (purity 98%); LCMS (ESI+) (method G): Rt 1.216 min., MH+ 338.20;
$^1$H NMR (500 MHz, DMSO-d$_6$) δ [ppm] 9.27 (s, 1H), 8.90 (s, 1H), 8.60 (s, 1H), 8.18 (s, 1H), 7.61-7.50 (m, 2H), 7.43-7.23 (m, 1H), 3.97-3.90 (m, 1H), 3.85 (s, 3H), 3.17-3.10 (m, 1H), 2.32 (s, 3H), 1.70-1.61 (m, 4H), 1.58-1.49 (m, 2H), 1.40-1.27 (m, 2H)

| nr. | name and/or structure |
|---|---|
| "A26" | (1S,2R)-[8-(1-Isopropyl-1H-pyrazol-4-yl)-pyrido[4,3-d]pyrimidin-2-yl]-cyclohexane-1,2-diamine |

HPLC (method A): Rt 2.31 min (purity 98%); LCMS (ESI+) (method G): Rt 1.430 min., MH+ 352.20;
$^1$H NMR (500 MHz, DMSO-d$_6$) δ [ppm] 9.56 (s, 1H), 9.31-9.28 (m, 1H), 9.01 (s, 1H), 8.73 (s, 1H), 8.37 (s, 1H), 8.34-8.29 (m, 1H), 8.22-8.13 (m, 2H), 4.66-4.51 (m, 2H), 3.76-3.68 (m, 1H), 2.10-1.95 (m, 2H), 1.83-1.72 (m, 2H), 1.72-1.58 (m, 2H), 1.54-1.42 (m, 8H)

| "A27" | (1S,2R)-N-[8-(1H-Indol-3-yl)-pyrido[4,3-d]pyrimidin-2-yl]-cyclohexane-1,2-diamine |

HPLC (method J): Rt 1.87 min (purity 100%); LCMS (ESI+) (method G): Rt 1.439 min., MH+ 359.20;
$^1$H NMR (500 MHz, DMSO-d$_6$) δ [ppm] 11.54 (s, 1H), 9.28 (s, 1H), 8.93 (s, 1H), 8.88 (s, 1H), 8.23-8.14 (m, 1H), 7.86 (d, J = 8.0, 1H), 7.55 (d, J = 7.7, 1H), 7.48 (d, J = 8.0, 1H), 7.21-7.14 (m, 1H), 7.13-7.06 (m, 1H), 3.98-3.90 (m, 1H), 3.15-3.09 (m, 1H), 1.81-1.42 (m, 6H), 1.37-1.19 (m, 2H)

| "A28" | 3-[2-((1R,2S)-2-Amino-cyclohexylamino)-pyrido[4,3-d]pyrimidin-8-yl]-benzenesulfonamide |

HPLC (method A): Rt 2.27 min (purity 100%); LCMS (ESI+) (method G): Rt 1.237 min., MH+ 399.10; HCl salt

| nr. | name and/or structure |
|---|---|
| "A29" | (1S,2R)-N48-(4,4-Dimethyl-chroman-7-yl)-pyrido[4,3-d]pyrimidin-2-yl]-cyclohexane-1,2-diamine |

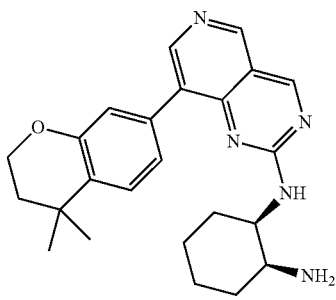 [SMILES: CC1(C)CCOc2cc(-c3cncc4cnc(N[C@@H]5CCCC[C@@H]5N)nc34)ccc21]

HPLC (method A): Rt 2.37 min (purity 100%); LCMS (ESI+) (method G): Rt 1.657 min., MH+ 404.30;
HCl salt: $^1$H NMR (300 MHz, DMSO-d$_6$) δ [ppm] 9.36 (s, 1H), 9.09-9.03 (m, 1H), 8.64 (s, 1H), 7.99-7.61 (m, 2H), 7.58-7.44 (m, 1H), 7.43-7.33 (m, 1H), 7.29-7.21 (m, 1H), 7.21-7.16 (m, 1H), 4.25-4.14 (m, 3H), 3.69 (s, 1H), 1.97-1.82 (m, 4H), 1.78-1.58 (m, 4H), 1.57-1.39 (m, 2H), 1.36 (s, 6H)

| "A30" | (R)-3-Methoxy-N1-(8-m-tolyl-pyrido[4,3-d]pyrimidin-2-yl)-propane-1,2-diamine |

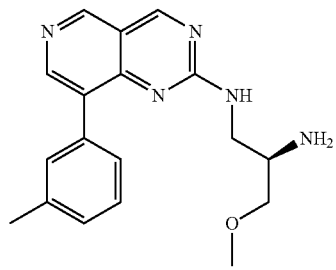 [SMILES: COC[C@H](N)CNc1ncc2cncc(-c3cccc(C)c3)c2n1]

HPLC (method A): Rt 2.29 min (purity 99%); LCMS (ESI+) (method G): Rt 1.341 min., MH+ 324.20;
HCl salt: $^1$H NMR (500 MHz, DMSO-d$_6$) δ [ppm] 9.52 (s, 1H), 9.33 (s, 1H), 8.88-8.77 (m, 1H), 8.72 (s, 1H), 8.22-8.16 (m, 2H), 7.65-7.60 (m, 2H), 7.46-7.39 (m, 1H), 7.31 (d, J = 7.8, 1H), 3.79-3.73 (m, 1H), 3.70-3.40 (m, 3H), 3.31 (s, 1H), 3.24 (s, 3H), 2.42 (s, 3H)

| "A31" | (1S,2R)-N-(8-m-Tolyl-pyrido[4,3-d]pyrimidin-2-yl)-cyclohexane-1,2-diamine |

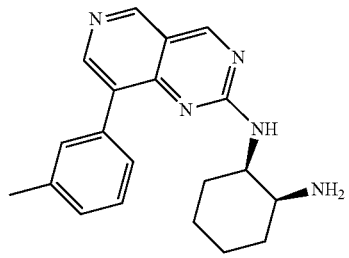 [SMILES: Cc1cccc(-c2cncc3cnc(N[C@@H]4CCCC[C@@H]4N)nc23)c1]

HPLC (method A): Rt 2.33 min (purity 99%); LCMS (ESI+) (method G): Rt 1.478 min., MH+ 334.20;
HCl salt: $^1$H NMR (500 MHz, DMSO-d$_6$) δ [ppm] 9.59 (s, 1H), 9.43 (s, 1H), 8.93 (d, J = 6.5, 1H), 8.76 (s, 1H), 8.19-8.12 (m, 2H), 7.68-7.60 (m, 2H), 7.43 (t, J = 7.6, 1H), 7.35-7.30 (m, 1H), 4.15-4.06 (m, 1H), 3.72-3.64 (m, 1H), 2.42 (s, 3H), 2.03-1.91 (m, 2H), 1.77-1.54 (m, 4H), 1.47-1.31 (m, 2H)

| nr. | name and/or structure |
|---|---|
| "A32" | (R)-4-Methyl-2-(8-m-tolyl-pyrido[4,3-d]pyrimidin-2-ylamino)-pentanoic acid amide |

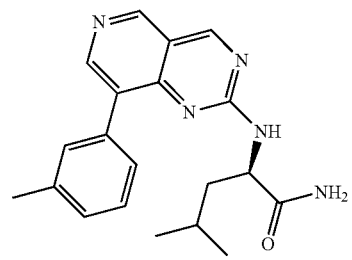 [SMILES: Cc1cccc(-c2cncc3cnc(N[C@H](CC(C)C)C(N)=O)nc23)c1]

HPLC (method A): Rt 2.41 min (purity 99%); LCMS (ESI+) (method G): Rt 1.696 min., MH+ 350.20;
$^1$H NMR (500 MHz, DMSO-d$_6$) δ [ppm] 9.33 (s, 1H), 9.01 (s, 1H), 8.63 (s, 1H), 7.94 (d, J = 8.2, 1H), 7.64-7.57 (m, 2H), 7.35 (t, J = 7.6, 1H), 7.24-7.18 (m, 1H), 7.10 (s, 1H), 6.97 (s, 1H), 4.42-4.35 (m, 1H), 2.39 (s, 3H), 1.71-1.59 (m, 3H), 0.88 (d, J = 6.4, 3H), 0.81 (d, J = 6.3, 3H)

| "A33" | (1S,2R)-N-[8-(4,5,6,7-Tetrahydro-pyrazolo[1,5-a]pyridin-2-yl)-pyrido[4,3-d]pyrimidin-2-yl]-cyclohexane-1,2-diamine |

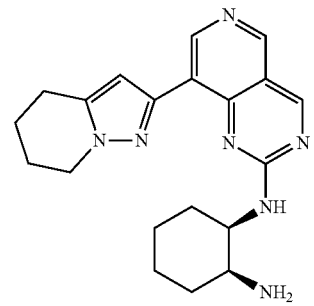 [SMILES: N[C@H]1CCCC[C@H]1Nc1ncc2cncc(-c3cc4n(n3)CCCC4)c2n1]

HPLC (method A): Rt 2.28 min (purity 91%); LCMS (ESI+) (method G): Rt 1.421 min., MH+ 364.30; HCl salt

| "A34" | 6-[2-((1R,2S)-2-Amino-cyclohexylamino)-pyrido[4,3-d]pyrimidin-8-yl]-2,2-dimethyl-4H-benzo[1,4]oxazin-3-one |

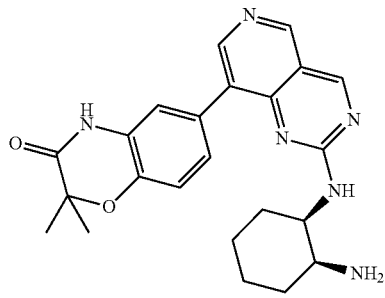 [SMILES: CC1(C)Oc2ccc(-c3cncc4cnc(N[C@@H]5CCCC[C@@H]5N)nc34)cc2NC1=O]

HPLC (method A): Rt 2.32 min (purity 100%); LCMS (ESI+) (method G): Rt 1.473 min., MH+ 419.20; HCl salt

| nr. | name and/or structure |
|---|---|
| "A35" | (1S,2R)-N-[8-(3-Methoxy-phenylethynyl)-pyrido[4,3-d]pyrimidin-2-yl]-cyclohexane-1,2-diamine 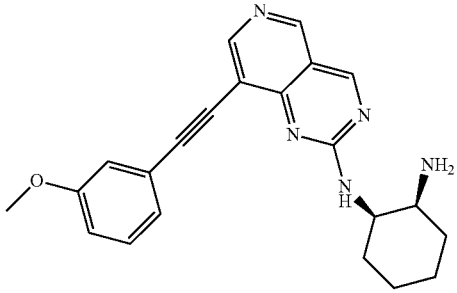 [SMILES: COc1cccc(C#Cc2cncc3cnc(N[C@@H]4CCCC[C@@H]4N)nc23)c1] HPLC (method A): Rt 2.40 min (purity 98%); LCMS (ESI+) (method G): Rt 1.695 min., MH+ 374.20; HCl salt |
| "A36" | (1S,2R)-N-[8-(1H-Benzoimidazol-5-yl)-pyrido[4,3-d]pyrimidin-2-yl]-cyclohexane-1,2-diamine 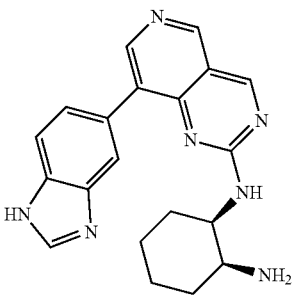 [SMILES: N[C@H]1CCCC[C@H]1Nc1ncc2cncc(-c3ccc4[nH]cnc4c3)c2n1] HPLC (method A): Rt 2.17 min (purity 88%); LCMS (ESI+) (method G): Rt 1.082 min., MH+ 360.20; HCl salt: $^1$H NMR (500 MHz, DMSO-$d_6$) δ [ppm] 9.52 (s, 1H), 9.42 (s, 1H), 9.27 (s, 1H), 8.84 (s, 1H), 8.38 (s, 1H), 8.31 (s, 1H), 8.13-7.73 (m, 5H), 4.14-4.08 (m, 1H), 3.72-3.62 (m, 1H), 1.93-1.80 (m, 2H), 1.82-1.49 (m, 4H), 1.44-1.31 (m, 2H) |
| "A37" | 5-[2-((1R,2S)-2-Amino-cyclohexylamino)-pyrido[4,3-d]pyrimidin-8-yl]-1,3-dihydro-benzimidazol-2-one 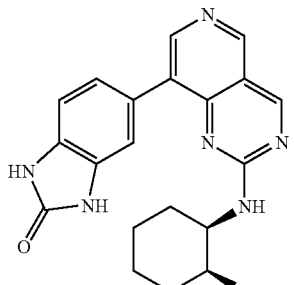 HPLC (method A): Rt 2.23 min (purity 99%); LCMS (ESI+) (method G): Rt 1.227 min., MH+ 376.10; HCl salt: $^1$H NMR (500 MHz, DMSO-$d_6$) δ [ppm] 10.90-10.84 (m, 1H), 10.81 (s, 1H), 9.56 (s, 1H), 9.34 (s, 1H), 8.77 (s, 1H), 8.73 (s, 1H), 8.02 (d, J = 6.2, 2H), 7.54-7.50 (m, 1H), 7.39 (dd, J = 8.1, 1.7, 1H), 7.07 (d, J = 8.1, 1H), 4.19-4.09 (m, 1H), 3.83 (s, 1H), 2.00-1.84 (m, 2H), 1.75-1.53 (m, 3H), 1.48-1.36 (m, 3H) |

| nr. | name and/or structure |
|---|---|
| "A38" | (1S,2R)-N-[8-(1,2,3,6-Tetrahydro-pyridin-4-yl)-pyrido[4,3-d]pyrimidin-2-yl]-cyclohexane-1,2-diamine 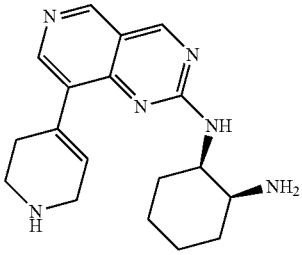 [SMILES: N[C@H]1CCCC[C@H]1Nc1ncc2cncc(C3=CCNCC3)c2n1] HPLC (method J): Rt 1.29 min (purity 68%); LCMS (ESI+) (method G): Rt 1.140 min., MH+ 325.20; HCl salt |
| "A39" | (1S,2R)-N-[8-(3,6-Dihydro-2H-pyran-4-yl)-pyrido[4,3-d]pyrimidin-2-yl]-cyclohexane-1,2-diamine 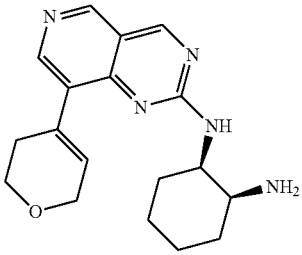 [SMILES: N[C@H]1CCCC[C@H]1Nc1ncc2cncc(C3=CCOCC3)c2n1] HPLC (method J): Rt 1.63 min (purity 94%); LCMS (ESI+) (method G): Rt 1.340 min., MH+ 326.20; HCl salt |
| "A40" | (1S,2R)-N-[8-(6-Methoxy-1H-indol-3-yl)-pyrido[4,3-d]pyrimidin-2-yl]-cyclohexane-1,2-diamine 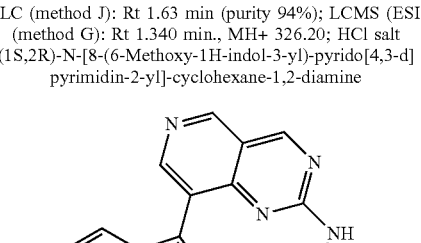 HPLC (method J): Rt 1.85 min (purity 64%); LCMS (ESI+) (method G): Rt 1.432 min., MH+ 389.20 |
| "A41" | (1S,2R)-N-[8-(6-Trifluoromethyl-1H-indol-3-yl)-pyrido[4,3-d]pyrimidin-2-yl]-cyclohexane-1,2-diamine 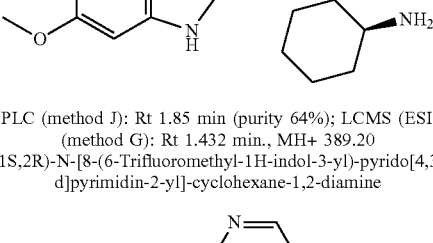 no HPLC data; LCMS (ESI+) (method G): Rt 1.642 min., MH+ 427.20; $^1$H NMR (500 MHz, DMSO-$d_6$) δ [ppm] 11.96-11.77 (m, 2H), 9.31 (s, 1H), 8.95 (s, 1H), 8.88 (s, 1H), 8.25 (s, 1H), 7.96 (d, J = 8.5, 1H), 7.82 (s, 1H), 7.71-7.44 (m, 2H), 7.39-7.33 (m, 1H), 3.91-3.82 (m, 1H), 3.15-3.09 (m, 1H), 1.63-1.50 (m, 4H), 1.39-1.09 (m, 4H) |

| nr. | name and/or structure |
|---|---|
| "A42" | (1S,2R)-N-[8-(6-Fluoro-1H-indol-2-yl)-pyrido[4,3-d]pyrimidin-2-yl]-cyclohexane-1,2-diamine |

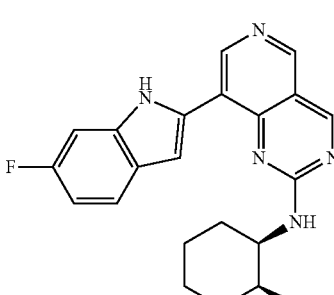

HPLC (method A): Rt 2.31 min (purity 92%); LCMS (ESI+) (method G): Rt 1.376 min., MH+ 377.10;
$^1$H NMR (500 MHz, DMSO-$d_6$) δ [ppm] 11.94-11.23 (m, 1H), 9.80-8.56 (m, 1H), 8.40-7.60 (m, 4H), 7.57-7.07 (m, 3H), 6.93-5.70 (m, 2H), 4.72-3.98 (m, 1H), 3.80-3.49 (m, 1H), 1.93-0.96 (m, 8H)

| | |
|---|---|
| "A43" | (1S,2R)-N-[8-(6,7-Dihydro-4H-pyrazolo[5,1-c][1,4]oxazin-2-yl)-pyrido[4,3-d]pyrimidin-2-yl]-cyclohexane-1,2-diamine |

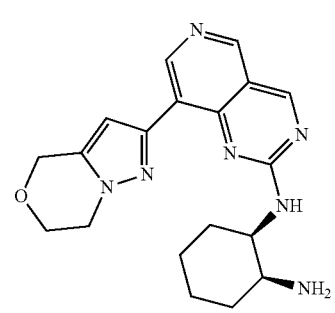 [SMILES: N[C@H]1CCCC[C@H]1Nc1ncc2cncc(-c3cc4n(n3)CCOC4)c2n1]

HPLC (method A): Rt 2.24 min (purity 100%); LCMS (ESI+) (method G): Rt 1.264 min., MH+ 366.10;
HCl salt: $^1$H NMR (500 MHz, DMSO-$d_6$) δ [ppm] 9.57 (s, 1H), 9.35 (s, 1H), 9.04 (s, 1H), 9.01-8.95 (m, 1H), 8.23-8.15 (m, 2H), 7.08 (s, 1H), 4.91 (d, J = 3.1, 2H), 4.61-4.35 (m, 1H), 4.31-4.20 (m, 2H), 4.18-4.12 (m, 2H), 3.79-3.53 (m, 1H), 2.01-1.91 (m, 2H), 1.82-1.66 (m, 4H), 1.53-1.41 (m, 2H)

| | |
|---|---|
| "A44" | 3-[2-((1R,2S)-2-Amino-cyclohexylamino)-pyrido[4,3-d]pyrimidin-8-yl]-1H-indole-5-carbonitrile |

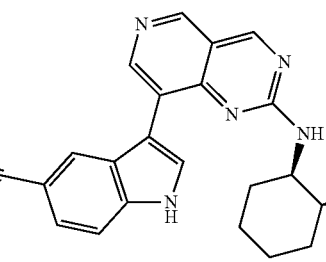

HPLC (method J): Rt 1.84 min (purity 100%); LCMS (ESI+) (method G): Rt 1.379 min., MH+ 384.20

| nr. | name and/or structure |
|---|---|
| "A45" | 3-[2-((1R,2S)-2-Amino-cyclohexylamino)-pyrido[4,3-d]pyrimidin-8-yl]-1H-indole-6-carbonitrile |

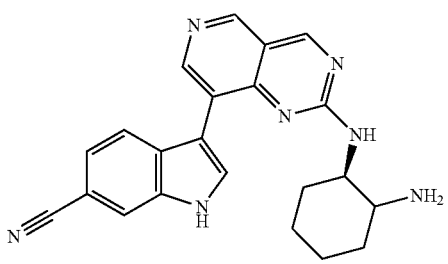 [SMILES: N#Cc1ccc2c(-c3cncc4cnc(N[C@@H]5CCCCC5N)nc34)c[nH]c2c1]

HPLC (method J): Rt 1.85 min (purity 100%); LCMS (ESI+) (method G): Rt 1.399 min., MH+ 384.30

| | |
|---|---|
| "A46" | (1S,2R)-N-[8-(5-Fluoro-1H-indol-3-yl)-pyrido[4,3-d]pyrimidin-2-yl]-cyclohexane-1,2-diamine |

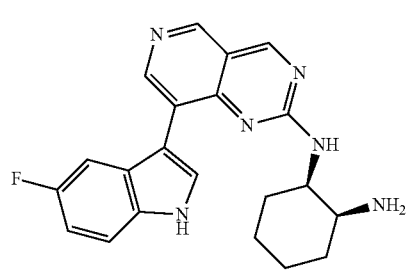 [SMILES: N[C@H]1CCCC[C@H]1Nc1ncc2cncc(-c3c[nH]c4ccc(F)cc34)c2n1]

LCMS (ESI+) (Method G): Rt 1.455 min., MH+ 377.20

| | |
|---|---|
| "A47" | (1S,2R)-N-[8-(6-Fluoro-1H-indol-3-yl)-pyrido[4,3-d]pyrimidin-2-yl]-cyclohexane-1,2-diamine |

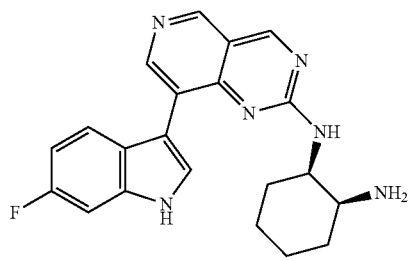 [SMILES: N[C@H]1CCCC[C@H]1Nc1ncc2cncc(-c3c[nH]c4cc(F)ccc34)c2n1]

LCMS (ESI+) (method G): Rt 1.469 min., MH+ 377.20;
$^1$H NMR (500 MHz, DMSO-$d_6$) δ [ppm] 11.61 (s, 1H), 9.30 (s, 1H), 8.94-8.86 (m, 3H), 8.16-8.12 (m, 1H), 7.85-7.80 (m, 1H), 7.57 (d, J = 7.6, 1H), 7.26 (dd, J = 9.9, 2.4, 2H), 6.94 (td, J = 9.3, 2.5, 1H), 3.93-3.87 (m, 1H), 3.12-3.07 (m, 1H) 1.76-1.65 (m, 2H), 1.49-1.40 (m, 2H), 1.36-1.18 (m, 4H)

| | |
|---|---|
| "A48" | (R)-N1-[8-(1H-Indol-3-yl)-pyrido[4,3-d]pyrimidin-2-yl]-3-methoxy-propane-1,2-diamine |

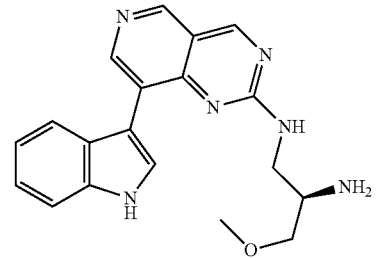 [SMILES: COC[C@H](N)CNc1ncc2cncc(-c3c[nH]c4ccccc34)c2n1]

HPLC (method J): Rt 1.68 min (purity 63%); LCMS (ESI+) (method G): Rt 1.288 min., MH+ 349.00

| nr. | name and/or structure |
|---|---|
| "A49" | cis-N3-[8-[6-(trifluoromethyl)-1H-indol-3-yl]pyrido[4,3-d]pyrimidin-2-yl]tetrahydropyran-3,4-diamine |
| | orange solid, LCMS (ESI+) (Method G), Rt 1.49 min., MH+ 429.2; $^1$H NMR (400 MHz, DMSO-d$_6$) δ [ppm] 11.90 (s, 1H), 9.36-9.32 (m, 1H), 8.97 (s, 1H), 8.90-8.86 (m, 1H), 8.23 (s, 1H), 7.97-7.92 (m, 1H), 7.86-7.78 (m, 2H), 7.69-7.62 (m, 1H), 7.42-7.32 (m, 2H), 4.06-3.92 (m, 1H), 3.78-3.72 (m, 1H), 3.64-3.55 (m, 1H), 3.27-3.24 (m, 1H), 3.21-3.11 (m, 1H), 2.93-2.88 (m, 1H), 1.90-1.75 (m, 1H), 1.64-1.58 (m, 1H) |
| "A50" | cis-N4-[8-[6-(trifluoromethyl)-1H-indol-3-yl]pyrido[4,3-d]pyrimidin-2-yl]tetrahydropyran-3,4-diamine |
| "A51" | cis-3,3-Difluoro-N1-[8-[6-(trifluoromethyl)-1H-indol-3-yl]pyrido[4,3-d]pyrimidin-2-yl]cyclohexane-1,2-diamine |
| "A52" | cis-3-Fluoro-N1-[8-[6-(trifluoromethyl)-1H-indol-3-yl]pyrido[4,3-d]-pyrimidin-2-yl]cyclohexane-1,2-diamine |
| "A53" | cis-4,4-Difluoro-N1-[8-[6-(trifluoromethyl)-1H-indol-3-yl]pyrido[4,3-d]pyrimidin-2-yl]cyclohexane-1,2-diamine |
| "A54" | cis-4-Fluoro-N1-[8-[6-(trifluoromethyl)-1H-indol-3-yl]pyrido[4,3-d]-pyrimidin-2-yl]cyclohexane-1,2-diamine |
| "A55" | cis-4,4-Difluoro-N2-[8-[6-(trifluoromethyl)-1H-indol-3-yl]pyrido[4,3-d]pyrimidin-2-yl]cyclohexane-1,2-diamine |
| "A56" | cis-4-Fluoro-N2-[8-[6-(trifluoromethyl)-1H-indol-3-yl]pyrido[4,3-d]-pyrimidin-2-yl]cyclohexane-1,2-diamine |
| "A57" | (1S,2S)-3,3-Difluoro-N2-[8-[6-(trifluoromethyl)-1H-indol-3-yl]pyrido[4,3-d]pyrimidin-2-yl]cyclohexane-1,2-diamine |

| nr. | name and/or structure |
|---|---|
| "A58" | cis-3-Fluoro-N2-[8-[6-(trifluoromethyl)-1H-indol-3-yl]pyrido[4,3-d]-pyrimidin-2-yl]cyclohexane-1,2-diamine |
| "A59" | cis-2-[[8-[6-(Trifluoromethyl)-1H-indol-3-yl]pyrido[4,3-d]pyrimidin-2-yl]amino]cyclohexanol |
| "A60" | 3,3,3-Trifluoro-N1-[8-[6-(trifluoromethyl)-1H-indol-3-yl]pyrido[4,3-d]pyrimidin-2-yl]propane-1,2-diamine |
| "A61" | (2R)-3-Methoxy-N1-[8-[6-(trifluoromethyl)-1H-indol-3-yl]pyrido[4,3-d]pyrimidin-2-yl]propane-1,2-diamine | yellow solid, HPLC: (Method J) 100%; Rt 2.003 min; LCMS (ESI+) (Method G) Rt 1.48 min, MH+ 417.1; $^1$H NMR (500 MHz, DMSO-$d_6$) δ [ppm] 11.90 (s, 1H), 9.30 (s, 1H), 8.95 (s, 1H), 8.89 (s, 1H), 8.35 (s, 1H), 8.00 (d, J = 8.4, 1H), 7.94 (t, J = 5.8, 1H), 7.83 (s, 1H), 7.40-7.34 (m, 1H), 3.47-3.37 (m, 1H), 3.17 (s, 3H), 315-3.01 (m, 3H), 1.61 (s, 2H)

| nr. | name and/or structure |
|---|---|
| "A62" | (2R)-4-Methyl-2-[[8-[6-(trifluoromethyl)-1H-indol-3-yl]pyrido[4,3-d]-pyrimidin-2-yl]amino]pentanamide | yellow solid, HPLC: (Method J) 100%; Rt 2.416 min.; LCMS (ESI+) (Method E) Rt 1.78 min, MH+ 443.2; $^1$H NMR (500 MHz, DMSO-$d_6$) δ [ppm] 11.92-11.89 (m, 1H), 9.35 (s, 1H), 8.99-8.95 (m, 2H), 8.44 (d, J = 2.6, 1H), 8.06-8.00 (m, 2H), 7.84-7.82 (m, 1H), 7.38 (dd, J = 8.5, 1.7, 1H), 7.10 (s, 1H), 6.96 (s, 1H), 4.38-4.31 (m, 1H), 1.78-1.66 (m, 2H), 1.64-1.54 (m, 1H), 0.88 (d, J = 6.2, 3H), 0.80 (d, J = 6.3, 3H)

| nr. | name and/or structure |
|---|---|
| "A63" | cis-N2-[8-(7-Fluoro-1H-indol-3-yl)pyrido[4,3-d]pyrimidin-2-yl]cyclohexane-1,2-diamine | orange solid; LCMS (ESI+) (Method G): Rt 1.44 min, MH+ 377.2; $^1$H NMR (500 MHz, DMSO-$d_6$) δ [ppm] 12.03 (s, 1H), 9.32 (s, 1H), 8.94 (s, 1H), 8.91 (s, 1H), 8.20-8.14 (m, 1H), 7.70-7.58 (m, 2H), 7.10-6.97 (m, 2H), 4.00-3.91 (m, 1H), 3.24-3.18 (m, 1H), 1.78-1.51 (m, 6H), 1.50-1.26 (m, 4H)

| nr. | name and/or structure |
|---|---|
| "A64" | N2-[8-[7-(Trifluoromethyl)-1H-indol-3-yl]pyrido[4,3-d]pyrimidin-2-yl]cyclohexane-1,2-diamine |

-continued

| nr. | name and/or structure |
|---|---|
| "A65" | (R)-2-[8-(6-Cyano-1H-indol-3-yl)-pyrido[4,3-d]pyrimidin-2-yl-amino]-4-methyl-pentanoic acid amide |

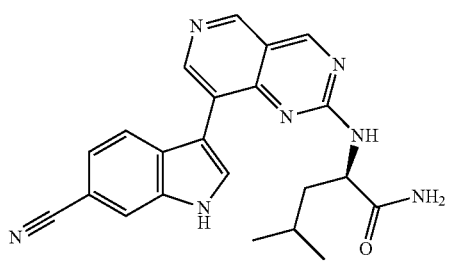 [SMILES: CC(C)C[C@@H](Nc1ncc2cncc(-c3c[nH]c4cc(C#N)ccc34)c2n1)C(N)=O]

yellow solid; HPLC: (Method J) 100%; Rt 2.116 min. LCMS (ESI+) (MethodG) Rt 1.58 min, MH+ 400.2); $^1$H NMR (500 MHz, DMSO-$d_6$) δ [ppm] 12.10-11.98 (m, 1H), 9.35 (s, 1H), 8.98 (s, 1H), 8.92 (s, 1H), 8.43 (d, J = 2.6, 1H), 8.05-7.95 (m, 3H), 7.43-7.38 (m, 1H), 7.11 (s, 1H), 6.95 (s, 1H), 4.36-4.27 (m, 1H), 1.76-1.65 (m, 2H), 1.63-1.53 (m, 1H), 0.87 (d, J = 6.2, 3H), 0.78 (d, J = 6.3, 3H)

| "A66" | (1S,2R)-N-[8-(4-Methyl-1H-indol-2-yl)-pyrido[4,3-d]pyrimidin-2-yl]-cyclohexane-1,2-diamine |
|---|---|

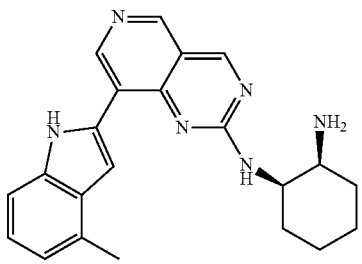 [SMILES: Cc1cccc2[nH]c(-c3cncc4cnc(N[C@@H]5CCCC[C@@H]5N)nc34)cc12]

beige solid; HPLC: (Method J) 100%; Rt 2.32 min, LCMS (ESI+) (Method G): Rt 1.35 min, MH+ 373.2

| "A67" | 3-[2-((R)-2-Amino-3-methoxy-propylamino)-pyrido[4,3-d]pyrimidin-8-yl]-1H-indole-6-carbonitrile |
|---|---|

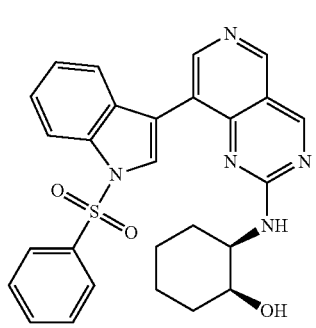

yellow solid, HPLC: (Method J) 100%; Rt 1.706 min. LCMS (ESI+) (Method G) Rt 1.24, MH+ 374.2; *H NMR (500 MHz, DMSO-$d_6$) δ [ppm] 12.03 (s, 1H), 9.30 (s, 1H), 8.95 (s, 1H), 8.86 (s, 1H), 8.35 (s, 1H), 8.01-7.97 (m, 1H), 7.97-7.90 (m, 3H), 7.89-7.66 (m, 1H), 7.40 (dd, J = 8.4, 1.5, 1H), 3.44-3.36 (m, 1H), 3.27-3.23 (m, 1H), 3.18 (s, 3H), 3.15-3.03 (m, 3H)

-continued

| nr. | name and/or structure |
|---|---|
| "A68" | (3R,4R)-N4-[8-(1H-Indol-3-yl)-pyrido[4,3-d]pyrimidin-2-yl]-tetrahydro-pyran-3,4-diamine |

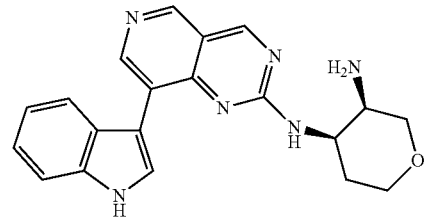 [SMILES: N[C@H]1COCC[C@H]1Nc1ncc2cncc(-c3c[nH]c4ccccc34)c2n1]

yellow powder LCMS(ESI+) (Method G): Rt 1.26 min, MH+ 361.0

| "A69" | 3[2-((3R,4R)-3-Amino-tetrahydro-pyran-4-ylamino)-pyrido[4,3-d]pyrimidin-8-yl]-1H-indole-6-carbonitrile |
|---|---|

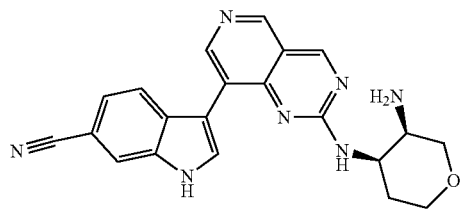 [SMILES: N#Cc1ccc2c(-c3cncc4cnc(N[C@@H]5CCOC[C@@H]5N)nc34)c[nH]c2c1]

yellow solid, LCMS (ESI+) (Method G) Rt 1.25 min, MH+ 386.1; $^1$H NMR (500 MHz, DMSO-$d_6$) δ [ppm] 12.14 (s, 1H), 9.47 (s, 1H), 9.41 (s, 1H), 9.05 (s, 1H), 8.93 (s, 1H), 8.47 (s, 1H), 8.34 (s, 1H), 8.07 (s, 1H), 7.97 (d, J = 8.3, 1H), 7.80 (d, J = 7.2, 1H), 7.46 (dd, J = 8.3, 1.5, 1H), 4.11-4.02 (m, 1H), 3.88-3.82 (m, 1H), 3.72-3.66 (m, 1H), 3.34-3.25 (m, 2H), 3.06 (s, 1H), 1.97-1.84 (m, 1H), 1.73-1.64 (m, 1H)

Examples 70 and 71

Enantiomer 1 of (cis)-2-[8-(1-benzenesulfonyl-1H-indol-3-yl)-pyrido[4,3-d]pyrimidin-2-ylamino]-cyclohexanol ("A70") and enantiomer 2 of (cis)-2-[8-(1-benzenesulfonyl-1H-indol-3-yl)-pyrido[4,3-d]pyrimidin-2-ylamino]-cyclohexanol ("A71")

Preparation of intermediate cis-2-(8-iodo-pyrido[4,3-d]pyrimidin-2-ylamino)-cyclohexanol

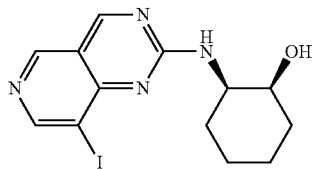

2-Chloro-8-iodo-pyrido[4,3-d]pyrimidine (500.00 mg; 1.098 mmol; 1.00 eq.), cis-2-amino-cyclohexanol hydrochloride (166.47 mg; 1.098 mmol; 1.00 eq.), ethanol (2.00 ml) and triethylamine (456.55 µl; 3.294 mmol; 3.00 eq.) were taken into a microwave vessel and sealed with a septum. By microwave the reaction mixture was now heated for 10 min. to 120° C. The solvent was removed under vacuo. The product was purified by flash chromatography and gives 107 mg (26%) of the title compound as a yellow amorphous powder; HPLC (Method A) Rt 2.36 min.; HPLC MS (Method G): (M+H) 371; Rt 1.519 min.

"A70" and "A71":

cis-2-(8-Iodo-pyrido[4,3-d]pyrimidin-2-ylamino)-cyclohexanol (117.30 mg; 316.86 µmol; 1.0 eq.), 1-(phenylsulfonyl)indole-3-boronic acid pinacol ester, 97% (188.00 mg; 0.476 mmol; 1.50 eq.), palladium(II) acetate (47% Pd) (3.60 mg; 16.035 µmol; 0.05 eq.), 2-dicyclohexylphosphino-2',6'-dimethoxybiphenyl (13.00 mg; 31.666 µmol; 0.10 eq.), potassium carbonate (129.00 mg; 0.933 mmol; 2.95 eq.), ethylene glycol dimethyl ether (3.30 ml; 31.857 mmol; 100.54 eq.) and water (1.10 ml; 61.043 mmol; 192.65 eq.) were taken into a microwave vessel, sealed with a septum and purged with nitrogen by, and heated for 45 min. to 150° C. The product was purified by flash chromatography and the enantiomers separated via SFC (Chiralpak AS-H with solvent $CO_2$+25% MOH+0.5% DEA).

"A70" elutes first from column. After evaporation of solvent, the product gives 43 mg (27%) of the title compound as a beige amorphous solid; HPLC (Method A): Rt 2.65 min.; HPLC MS (Method J): (M+H) 500.2; Rt 2.012 min.

"A71" elutes second from column to give 64 mg (40%) of the title compound as a beige amorphous solid; HPLC (Method A) Rt 2.67 min.; HPLC MS (Method J): (M+H) 500.2; Rt 2.009 min.

Example 72

3-[2-((1R,2S)-2-amino-cyclohexylamino)-pyrido[4,3-d]pyrimidin-8-yl]-1H-indole-7-carbonitrile ("A72")

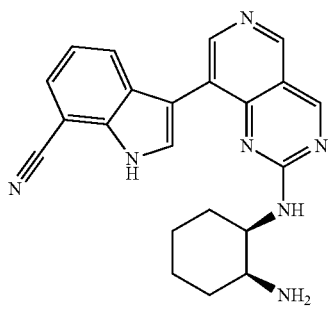 [SMILES: N#Cc1cccc2c(-c3cncc4cnc(N[C@@H]5CCCC[C@@H]5N)nc34)c[nH]c12]

72.1

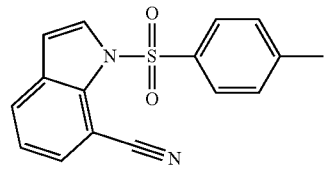 [SMILES: Cc1ccc(S(=O)(=O)n2ccc3cccc(C#N)c32)cc1]

1H-Indole-7-carbonitrile, 97% (1.00 g; 6.823 mmol; 1.000 eq.) was dissolved in toluene (20.00 ml; 188.843 mmol; 27.676 eq.). Tetra-n-butylammonium hydrogen sulfate (347.52 mg; 1.024 mmol; 0.150 eq.) was added. Sodium hydroxide solution 32% (20.00 ml; 216.016 mmol; 31.658 eq.) and 4-toluenesulfonyl chloride (1.34 ml; 10.235 mmol; 1.500 eq.) were added at 0° C. to the suspension and stirred vigorously for 14 h at rt. The reaction mixture was treated with toluene and water, the layers were separated and the organic extract was washed with saturated ammoniumchloride solution. The organic layer was dried over $MgSO_4$, filtered and concentrated under reduced pressure. The residue was treated with DCM and concentrated under reduced pressure to give 2 g (69%) of the title compound as a off-white solid; HPLC MS (Method J): (M+H) 297.1; (percent area) 90.4%; Rt 2.193 min.

72.2 3-bromo-1-(toluene-4-sulfonyl)-1H-indole-7-carbonitrile

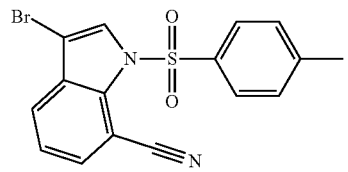 [SMILES: Cc1ccc(S(=O)(=O)n2cc(Br)c3cccc(C#N)c32)cc1]

1-(Toluene-4-sulfonyl)-1H-indole-7-carbonitrile (1.55 g; 4.728 mmol; 1.000 eq.) was dissolved in acetonitrile (35.00 ml; 670.109 mmol; 141.724 eq.). Copper(II) bromide anhydrous (3.17 g; 14.185 mmol; 3.000 eq.) was added and the suspension was stirred at rt for 2 days and heated to reflux for 2 days. The reaction mixture was treated with 80 ml 7M aqueous ammonia solution (approx. 12.5%) and extracted with EtOAc 3×. The combined organic layers were dried over $MgSO_4$, filtered and evaporated under reduced pressure to give 1 g (65%) of the title compound as a beige solid; HPLC MS (Method J): (M+H) 375; (percent area) 88.6%; Rt 2.431 min.

72.3 3-(4,4,5,5-tetramethyl-[1,3,2]dioxaborolan-2-yl)-1-(toluene-4-sulfonyl)-1H-indole-7-carbonitrile

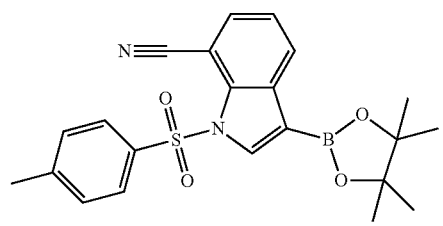

4,4,5,5,4',4',5',5'-Octamethyl-[2,2']bi[[1,3,2]dioxaborolanyl] (1.01 g; 3.975 mmol; 1.300 eq.), potassium acetate (0.90 g; 9.173 mmol; 3.000 eq.) and bis(triphenylphosphine)palladium(II) chloride (15.2% Pd) (85.85 mg; 0.122 mmol; 0.040 eq.) were added in a microwave vial. 3-Bromo-1-(toluene-4-sulfonyl)-1H-indole-7-carbonitrile (1.30 g; 3.058 mmol; 1.000 eq.) in tetrahydrofuran SeccoSolv® (10.00 ml; 123.429 mmol; 40.367 eq.) was added while purging nitrogen through the suspension and the reaction mixture was heated in a microwave for 2 h at 100° C. The reaction mixture was concentrated under reduced pressure. The residue was treated with DCM/MeOH, the precipitate was filtered off and the mother liquor was concentrated under reduced pressure. This residue was purified by flash chromatography to give 497 mg (38%) of the title compound as a colorless solid; HPLC MS (Method J): (M+H) 341.1; (M+Na) 363.1; (percent area) 100%; Rt 1.95 min.

72.4 ((1S,2R)-2-{8-[7-cyano-1-(toluene-4-sulfonyl)-1H-indol-3-yl]-pyrido-[4,3-d]pyrimidin-2-ylamino}-cyclohexyl)-carbamic acid tert-butyl ester

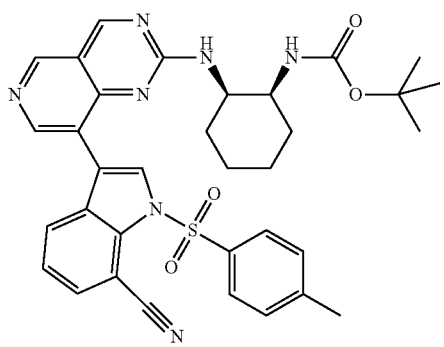 [SMILES: Cc1ccc(S(=O)(=O)n2cc(-c3cncc4cnc(N[C@@H]5CCCC[C@@H]5NC(=O)OC(C)(C)C)nc34)c3cccc(C#N)c32)cc1]

In a microwave vial [(1S,2R)-2-(8-iodo-pyrido[4,3-d]pyrimidin-2-ylamino)-cyclohexyl]-carbamic acid tert-butyl ester (200.00 mg; 0.426 mmol; 1.000 eq.), 3-(4,4,5,5-tetramethyl-[1,3,2]dioxaborolan-2-yl)-1-(toluene-4-sulfonyl)-1H-indole-7-carbonitrile (215.96 mg; 0.511 mmol; 1.200 eq.), palladium(II)-acetat (47% Pd) (4.78 mg; 0.021 mmol; 0.050 eq.), 2-dicyclohexylphosphino-2',6'-dimethoxybiphenyl (17.49 mg; 0.043 mmol; 0.100 eq.) and potassium carbonate (173.62 mg; 1.256 mmol; 2.948 eq.) were added and suspended in ethylenglycoldimethylether (4.41 ml; 42.615 mmol; 100.000 eq.) and water (1.54 ml; 85.230 mmol; 200.000 eq.) while purging nitrogen through the suspension. The suspension was heated in a microwave for 45 min at 150° C. The reaction mixture was concentrated under reduced pressure and purified by Flash Chromatography to give a mixture of the title compound and de-tosylated product. 138 mg (24%) of the title compound were obtained as a solid; HPLC MS (Method J): (M+H) 638.3 and 484.3 (de-tosylated); Rt 2.172/1.887 min.

72.5 3-[2-((1R,2S)-2-amino-cyclohexylamino)-pyrido[4,3-d]pyrimidin-8-yl]-1H-indole-7-carbonitrile The solid from example 72.4 was dissolved in dichloromethane SeccoSolv® (1.50 ml; 23.489 mmol). Trifluoroacetic acid (158.04 µl; 2.051 mmol) was added and the solution was stirred at rt for 14 h. The solvent was evaporated under reduced pressure. Ethanol (8.00 ml; 137.189 mmol), tetrahydrofuran SeccoSolv® (2.00 ml; 24.686 mmol) and sodium hydroxide pellets (81.65 mg; 2.042 mmol; 20.000 eq.) were added. The solution was stirred at 50° C. for 14 h. The solvent was evaporated under reduced pressure. The residue was treated with water and filtered and dried under vacuum. This gives 86 mg of the title compound as a yellow solid; $^1$H NMR (500 MHz, DMSO-$d_6$) δ [ppm] 12.41 (s, 1H), 9.30 (s, 1H), 8.94 (s, 1H), 8.89 (s, 1H), 8.23-8.14 (m, 2H), 7.68 (d, J=7.4, 1H), 7.60 (d, J=7.8, 1H), 7.24 (t, J=7.7, 1H), 3.88-3.81 (m, 1H), 3.10-3.04 (m, 1H), 1.72-1.63 (m, 2H), 1.64-1.50 (m, 4H), 1.37-1.17 (m, 2H); HPLC MS (Method J): (M+H) 384.2; (percent area) 100%; Rt 1.396 min.

Example 73

Enantiomer 1 of 3-[2-((cis)-2-hydroxy-cyclohexylamino)-pyrido[4,3-d]pyrimidin-8-yl]-1H-indole-6-carbonitrile ("A73")

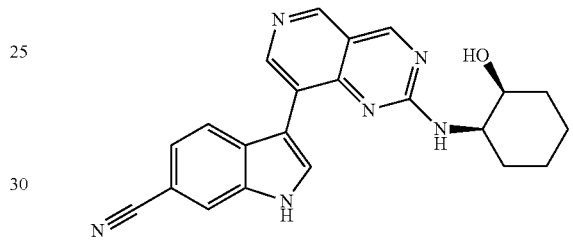

73.1 Enantiomer 1 and Enantiomer 2: cis-2-(8-iodo-pyrido[4,3-d]pyrimidin-2-ylamino)-cyclohexanol

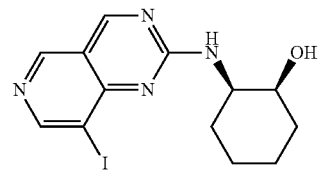 [SMILES: O[C@H]1CCCC[C@H]1Nc1ncc2cncc(I)c2n1]

2-Chloro-8-iodo-pyrido[4,3-d]pyrimidine (1.00 g; 2.556 mmol; 1.00 eq.), cis-2-amino-cyclohexanol hydrochloride (387.57 mg; 2.556 mmol; 1.00 eq.), ethanol (10.00 ml; 0.171 mol; 67.09 eq.) and triethylamine (1.06 ml; 7.668 mmol; 3.00 eq.) were taken into a microwave vessel and sealed with a septum. The reaction mixture was heated for 10 min in a microwave to 120° C. The reaction mixture was evaporated to dryness and the product purified by flash chromatography. The enantiomers were separated by chiral SFC.

Enantiomer 1: The stereoisomer eluates first from column Chiralpak AS-H with solvent $CO_2$+20% MOH+0.5% DEA; absolute configuration arbitrary; 61 mg (6%) of the title compound as a yellow amorphous powder; HPLC (Method A): (percent area) 100%; Rt 2.41 min.; HPLC MS (Method J): (M+H) 371; Rt 1.513 min.

Enantiomer 2: The stereoisomer eluates second from column Chiralpak AS-H with solvent $CO_2$+20% MOH+0.5% DEA; absolute configuration arbitrary; 62.50 mg; 0.169 mmol.

73.2 3-[2-((1R,2S)-2-hydroxy-cyclohexylamino)-pyrido[4,3-d]pyrimidin-8-yl]-1H-indole-6-carbonitrile 2-(8-Iodo-pyrido[4,3-d]pyrimidin-2-ylamino)-cyclohexanol (enantiomer 1) from example 73.1 (61.40 mg; 0.166 mmol; 1.00 eq.), 1-BOC-6-cyanoindole-3-boronic acid, pinacol ester (95.00 mg; 0.248 mmol; 1.49 eq.), palladium (II)-acetat (47% Pd) (1.90 mg; 0.008 mmol; 0.05 eq.), 2-dicyclohexylphosphino-2',6'-dimethoxybiphenyl (6.80 mg; 0.017 mmol; 0.10 eq.), potassium carbonate (68.00 mg; 0.492 mmol; 2.97 eq.), ethylenglycoldimethylether (2.10 ml; 20.273 mmol; 122.23 eq.) and water (0.70 ml; 38.846 mmol; 234.21 eq.) were taken into a microwave vessel, sealed with a septum and purged with nitrogen. The reaction was heated in a microwave for 45 min. to 150° C. The reaction mixture was evaporated to dryness and the product purified by flash chromatography. This gives 46 mg (70%) of the title compound as a yellow amorphous solid; $^1$H NMR (500 MHz, DMSO-$d_6$) δ [ppm] 12.09 (s, 1H), 9.30 (s, 1H), 8.95 (s, 1H), 8.86 (s, 1H), 8.30 (d, J=2.6, 1H), 7.99 (s, 1H), 7.92 (d, J=8.3, 1H), 7.55-7.29 (m, 2H), 4.60 (d, J=4.0, 1H), 3.91 (s, 1H), 3.82-3.72 (m, 1H), 1.75-1.50 (m, 5H), 1.38-1.25 (m, 2H), 1.20-1.08 (m, 1H); HPLC (Method A): (percent area) 98.1%; Rt 2.43 min.; HPLC MS (Method J): (M+H) 385.1; Rt 1.599 min.

Example 74

Enantiomer 2 of 3-[2-((cis)-2-hydroxy-cyclohexylamino)-pyrido[4,3-d]pyrimidin-8-yl]-1H-indole-6-carbonitrile ("A74")

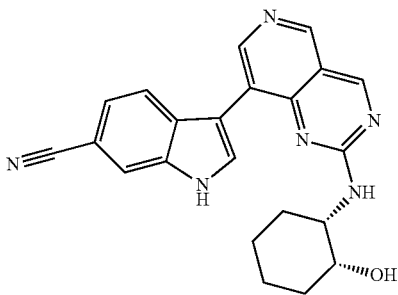 [SMILES: N#Cc1ccc2c(-c3cncc4cnc(N[C@H]5CCCC[C@H]5O)nc34)c[nH]c2c1]

2-(8-Iodo-pyrido[4,3-d]pyrimidin-2-ylamino)-cyclohexanol (Enantiomer 2 from example 73.1 (62.50 mg; 0.169 mmol; 1.00 eq.), 1-BOC-6-cyanoindole-3-boronic acid, pinacol ester (97.00 mg; 0.253 mmol; 1.50 eq.), palladium (II)-acetat (47% Pd) (1.90 mg; 0.008 mmol; 0.05 eq.), 2-dicyclohexylphosphino-2',6'-dimethoxybiphenyl (6.80 mg; 0.017 mmol; 0.10 eq.), potassium carbonate (68.00 mg; 0.492 mmol; 2.91 eq.), ethylenglycoldimethylether (2.10 ml; 20.273 mmol; 120.08 eq.) and water (0.70 ml; 38.846 mmol; 230.08 eq.) were taken into a microwave vessel, sealed with a septum and purged with nitrogen. The reaction was heated in a microwave for 45 min. to 150° C. The reaction mixture was evaporated to dryness. The residue was purified by flash chromatography. This gives 22 mg (34%) of the title compound as a yellow amorphous powder; $^1$H NMR (500 MHz, DMSO-$d_6$) δ [ppm] 12.18 (s, 1H), 9.37 (s, 1H), 9.06 (s, 1H), 8.86 (s, 1H), 8.35 (d, J=2.6, 1H), 8.01 (s, 1H), 7.95 (d, J=8.3, 1H), 7.87 (s, 1H), 7.47-7.38 (m, 1H), 4.62 (s, 1H), 3.96-3.87 (m, 1H), 3.84-3.75 (m, 1H), 1.81-1.46 (m, 4H), 1.40-1.05 (m, 4H);

HPLC (Method A): (percent area) 100%; Rt 2.43 min.; HPLC MS (Method J): (M+H) 385.1; Rt 1.593 min.

Example 75

3-[2-((S)-5,5-difluoro-piperidin-3-ylamino)-pyrido[4,3-d]pyrimidin-8-yl]-1H-indole-6-carbonitrile ("A75")

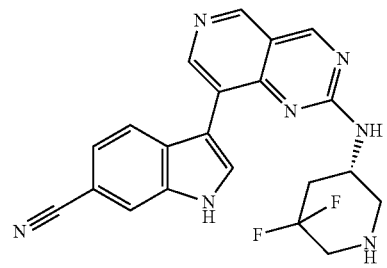

75.1 (S)-3,3-difluoro-5-(8-iodo-pyrido[4,3-d]pyrimidin-2-ylamino)-piperidine-1-carboxylic acid benzyl ester

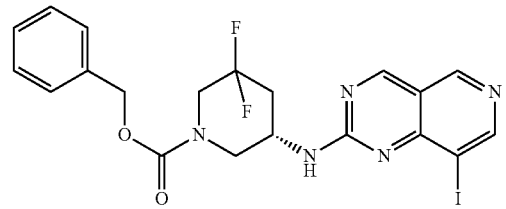

2-Chloro-8-iodo-pyrido[4,3-d]pyrimidine (200.000 mg; 0.686 mmol; 100.00 mol %) and (S)-5-amino-3,3-difluoro-piperidine-1-carboxylic acid benzyl ester (211.463 mg; 0.686 mmol; 100.00 mol %) was added together with triethylamine (0.143 ml; 1.029 mmol; 150.00 mol %) and ethanol (600.000 µl) in a microwave vessel, closed with a septum and heated 5 min in a microwave at 120° C. Water was added and the precipitation was filtered off. The precipitation was dried in vacuo to give 310 mg (62%) of the title compound as a brown film; HPLC MS (Method H): Rt 2.54 min, MH+526.0.

75.2 (S)-5-[8-(6-cyano-1H-indol-3-yl)-pyrido[4,3-d]pyrimidin-2-ylamino]-3,3-difluoro-piperidine-1-carboxylic acid benzyl ester

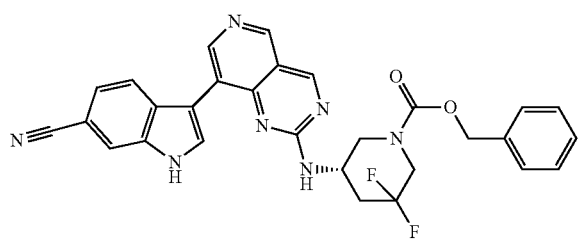

In a microwave vessel 1-BOC-6-cyanoindole-3-boronic acid, pinacol ester (57.592 mg; 0.150 mmol; 110.00 mol %), 2-dicyclohexylphosphino-2',6'-dimethoxybiphenyl (S-Phos) (5.777 mg; 0.014 mmol; 10.00 mol %) and potassium carbonate (56.593 mg; 0.409 mmol; 300.00 mol %) was suspended in ethylenglycoldimethylether (5.000 ml) and water (1.000 ml). Under nitrogen palladium(II)-acetat (3.064 mg; 0.014 mmol; 10.00 mol %) was added, closed with a septum and heated by microwave (160° C., 60 min). The product was purified by flash chromatography to give 45 mg (39%) of the title compound as a yellow solid; HPLC (Method H): Rt 2.494 min.; HPLC MS (Method G): (M+H) 540.2; Rt 1.866 min.

75.3 3-[2-((S)-5,5-difluoro-piperidin-3-ylamino)-pyrido[4,3-d]pyrimidin-8-yl]-1H-indole-6-carbonitrile In a microwave-vial (S)-5-[8-(6-cyano-1H-indol-3-yl)-pyrido[4,3-d]pyrimidin-2-ylamino]-3,3-difluoro-piperidine-1-carboxylic acid benzyl ester (35.000 mg; 0.041 mmol; 42.50 mol %) and (S)-5-[8-(6-cyano-1H-indol-3-yl)-pyrido[4,3-d]pyrimidin-2-ylamino]-3,3-difluoro-piperidine-1-carboxylic acid benzyl ester (45.000 mg; 0.055 mmol; 57.50 mol %) were dissolved in dichlormethane (1.000 ml). Then trifluoroacetic acid (0.447 ml; 5.779 mmol; 6000.00 mol %) was added. The vial was capped with a septum and heated by microwave (120° C., 2 h), The solution was evaporated to dryness. The residue was purified by preparative HPLC to give 8 mg (20%) of the title compound as a yellow solid; $^1$H NMR (500 MHz, DMSO-$d_6$) δ [ppm] 12.17 (s, 1H), 10.68-9.80 (m, 2H), 9.55 (s, 1H), 9.29 (s, 1H), 9.04-8.79 (m, 2H), 8.39 (d, J=2.7, 1H), 8.02 (s, 1H), 7.93 (d, J=8.3, 1H), 7.49-7.43 (m, 1H), 4.45-4.36 (m, 1H), 3.68-3.63 (m, 1H), 3.38-3.32 (m, 2H), 3.11 (t, J=11.5, 1H), 2.74-2.58 (m, 1H), 2.26-2.10 (m, 1H); HPLC MS (Method G): (M+H) 406.2; Rt 1.311 min.

Example 76

(1S,2R)—N-[8-(1H-pyrrolo[2,3-c]pyridin-3-yl)-pyrido[4,3-d]pyrimidin-2-yl]-cyclohexane-1,2-diamine ("A76")

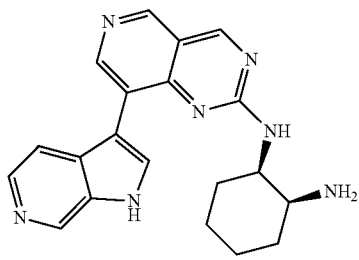 [SMILES: N[C@H]1CCCC[C@H]1Nc1ncc2cncc(-c3c[nH]c4cnccc34)c2n1]

76.1 1-(toluene-4-sulfonyl)-1H-pyrrolo[2,3-c]pyridine

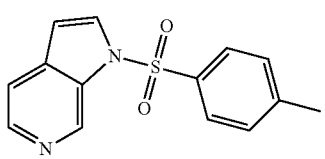 [SMILES: Cc1ccc(S(=O)(=O)n2ccc3ccncc32)cc1]

6-Azaindole (1.00 g; 8.296 mmol; 1.000 eq.) was suspended in toluene (22.00 ml; 207.727 mmol; 25.041 eq.) and to this suspension tetra-n-butylammonium hydrogen sulfate (422.50 mg; 1.244 mmol; 0.150 eq.) was added. At 0° C. sodium hydroxide 32% (22.00 ml; 237.618 mmol; 28.644 eq.) and 4-toluenesulfonyl chloride (1.62 ml; 12.443 mmol; 1.500 eq.) were added and the reaction stirred at RT for 14 h. The reaction mixture was diluted with toluene and water was added. Phases were separated; the organic layer was washed successively with water, saturated aqueous ammoniumchloride solution and water once again, dried over MgSO$_4$, filtered and evaporated under reduced pressure to give 2 g (68%) of the title compound as a beige solid; HPLC MS (Method G): (M+H) 273.1; (percent area) 100%; Rt 1.489 min.

76.2 3-bromo-1-(toluene-4-sulfonyl)-1H-pyrrolo[2,3-c]pyridine

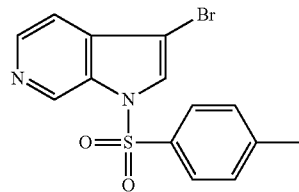 [SMILES: Cc1ccc(S(=O)(=O)n2cc(Br)c3ccncc32)cc1]

3-Bromo-1-(toluene-4-sulfonyl)-1H-pyrrolo[2,3-c]pyridine (687.00 mg; 1.956 mmol; 1.000 eq.) was dissolved in acetonitrile (15.00 ml; 287.190 mmol; 113.840 eq.). Copper (II) bromide anhydrous (1.31 g; 5.865 mmol; 2.325 eq.) was added and the suspension was heated to reflux and stirred 3 days. The reaction mixture was treated with 30 ml 7M aqueous ammonia solution (approx. 12.5%) and extracted with EtOAc 3×. The organic layer was dried over MgSO$_4$, filtered and evaporated under reduced pressure: The product was purified by Flash Chromatography to give 184 mg (21%) of the title compound as a colorless solid; HPLC MS (Method G): (M+H) 351; (percent area) 100%; Rt 1.694 min.

76.3 3-(4,4,5,5-tetramethyl-[1,3,2]dioxaborolan-2-yl)-1-(toluene-4-sulfonyl)-1H-pyrrolo[2,3-c]pyridine

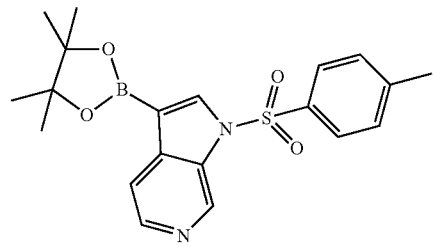

3-Bromo-1-(toluene-4-sulfonyl)-1H-pyrrolo[2,3-c]pyridine (184.00 mg; 0.524 mmol; 1.000 eq.), 4,4,5,5,4',4',5',5'-octamethyl-[2,2']bi[[1,3,2]dioxaborolanyl] (161.26 mg; 0.629 mmol; 1.200 eq.) and potassium acetate (103.87 mg; 1.048 mmol; 2.000 eq.) were suspended in ethylene glycol dimethyl ether (2.50 ml; 23.893 mmol; 45.607 eq.). The reaction mixture was purged with nitrogen while adding (1,1'-bis(diphenylphosphino)ferrocene) dichloropalladium (II), complex with dichloromethane (21.39 mg; 0.026 mmol; 0.050 eq.). The resulting mixture was heated for 2 h at 100° C. in the microwave. The reaction mixture was concentrated under reduced pressure. The residue was dissolved in EtOAc and water. The phases were separated and the organic layer was washed with water 2 more times. The organic layer was dried over MgSO₄, filtered and evaporated under reduced pressure. This gives 216 mg (97%) of the title compound as a brown solid; HPLC MS (Method G): (M+H) 317.1; (desired product as free boronic acid); (percent area) 93.6%; Rt 1.424 min.

76.4 {(1S,2R)-2-[8-(1H-pyrrolo[2,3-c]pyridin-3-yl)-pyrido[4,3-d]pyrimidin-2-ylamino]-cyclohexyl}-carbamic acid tert-butyl ester

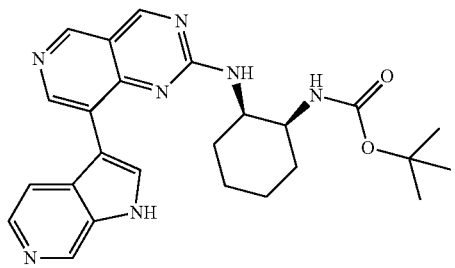 [SMILES: CC(C)(C)OC(=O)N[C@H]1CCCC[C@H]1Nc1ncc2cncc(-c3c[nH]c4cnccc34)c2n1]

[(1S,2R)-2-(8-Iodo-pyrido[4,3-d]pyrimidin-2-ylamino)-cyclohexyl]-carbamic acid tert-butyl ester (192.00 mg; 0.409 mmol; 1.000 eq.), 3-(4,4,5,5-tetramethyl-[1,3,2]dioxaborolan-2-yl)-1-(toluene-4-sulfonyl)-1H-pyrrolo[2,3-c]pyridine (195.53 mg; 0.460 mmol; 1.123 eq.), palladium (II)-acetat (47% Pd) (4.59 mg; 0.020 mmol; 0.050 eq.), 2-dicyclohexylphosphino-2',6'-dimethoxybiphenyl (16.79 mg; 0.041 mmol; 0.100 eq.) and potassium carbonate (166.68 mg; 1.206 mmol; 2.948 eq.) were suspended in ethylenglycoldimethylether (4.24 ml; 40.910 mmol; 100.000 eq.) and water (1.47 ml; 81.821 mmol; 200.000 eq.) while purging nitrogen through the suspension. The suspension was heated for 45 min at 150° C. in the microwave. The reaction mixture was concentrated under reduced pressure. The product was purified by flash chromatography to give 98 mg (49%) of the title compound as a brown solid; HPLC MS (Method G): (M+H) 460.3; (percent area) 94.2%; Rt 1.398 min.

76.5 (1S,2R)—N-[8-(1H-pyrrolo[2,3-c]pyridin-3-yl)-pyrido[4,3-d]pyrimidin-2-yl]-cyclohexane-1,2-diamine {(1S,2R)-2-[8-(1H-Pyrrolo[2,3-c]pyridin-3-yl)-pyrido[4,3-d]pyrimidin-2-ylamino]-cyclohexyl}-carbamic acid tert-butyl ester (92.00 mg; 0.189 mmol; 1.000 eq.) was dissolved in dichloromethane (1.50 ml; 23.489 mmol; 124.553 eq.). Trifluoroacetic acid (145.29 µl; 1.886 mmol; 10.000 eq.) was added and the reaction mixture was stirred at rt for 3 days. The reaction mixture was evaporated under reduced pressure and the product was purified by preparative HPLC to give 38 mg (43%) of the title compound as a yellow solid; HPLC MS (Method G): (M+H) 360.2; (percent area) 100%; Rt 1.02 min.

Example 77

3-[2-((1R,2S)-2-amino-cyclohexylamino)-pyrido[4,3-d]pyrimidin-8-yl]-1H-indole-6-carboxylic acid amide ("A77")

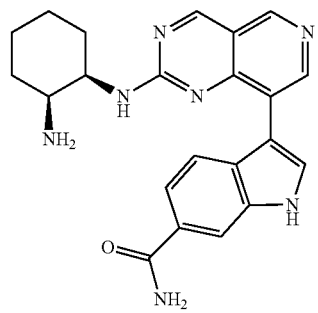 [SMILES: NC(=O)c1ccc2c(-c3cncc4cnc(N[C@@H]5CCCC[C@@H]5N)nc34)c[nH]c2c1]

77.1 1H-indole-6-carboxamide

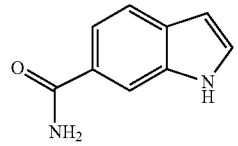

A solution of 6-cyanoindole (1.000 g; 7.034 mmol; 1.00 eq.) in methanol (10.000 ml; 246.567 mmol; 35.05 eq.) was treated with hydrogen peroxide 30% (0.790 ml; 7.738 mmol; 1.10 eq.) and sodium hydroxide solution (1 N) (5.000 ml; 130.010 mmol; 18.48 eq.), then heated at 40° C. for 1 h. Hydrogen peroxide 30% (0,790 ml; 7,738 mmol; 1.10 eq.) was added and heated at 40° C. for 19 h. The reaction mixture was cooled, poured into 100 ml of ice-water and stirred for 15 min. The resulting precipitate was collected by filtration, washed with water and dried in vacuo at 40° C. to give 894 mg (79%) of the title compound as a beige crystals; HPLC MS (Method G): (M+H) 161.1; (percent area) 100%; Rt 1.185 min.

77.2 tert-butyl 6-carbamoylindole-1-carboxylate

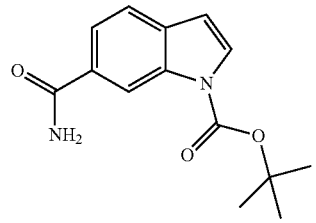 [SMILES: CC(C)(C)OC(=O)n1ccc2ccc(C(N)=O)cc21]

1H-Indole-6-carboxamide (876,000 mg; 5,469 mmol; 1.00 eq.) was dissolved in dichloromethane (10.000 ml; 156.594 mmol; 28.63 eq.). Di-tert-butyl dicarbonate (1.287 ml; 6.016 mmol; 1.10 eq.) and 4-(dimethylamino)pyridine (66.816 mg; 0.547 mmol; 0.10 eq.) were added and the solution was stirred at RT for 1 h. The reaction mixture was diluted with DCM and washed 3× with water. The organic layer was dried over MgSO$_4$, filtered and concentrated under reduced pressure to give 1 g (98%) of the title compound; HPLC MS (Method G): Rt 1.19 min, MH+161.1.

77.3 tert-butyl 3-bromo-6-carbamoyl-indole-1-carboxylate

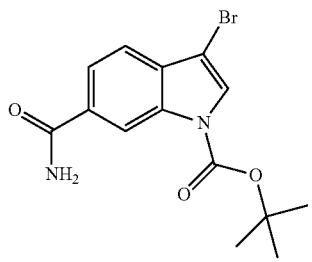 [SMILES: CC(C)(C)OC(=O)n1cc(Br)c2ccc(C(N)=O)cc21]

tert-Butyl 6-carbamoylindole-1-carboxylate (1.418 g; 5.305 mmol; 1.00 eq.) was dissolved in dichloromethane (10.000 ml; 156.594 mmol; 29.52 eq.). N-Bromo-succinimide (1.133 g; 6.365 mmol; 1.20 eq.) was added and the solution was stirred at rt for 2 h. The reaction mixture was diluted with DCM and washed 3× with water. The organic layer was dried over MgSO$_4$, filtered and concentrated under reduced pressure. The product was purified by Flash Chromatography to give 347 mg (19%) of the title compound as a beige solid;

HPLC MS (Method G): (M+H) 339; (percent area) 100%; Rt 2.186 min.

77.4 tert-butyl 6-carbamoyl-3-(4,4,5,5-tetramethyl-1,3,2-dioxaborolan-2-yl)indole-1-carboxylate

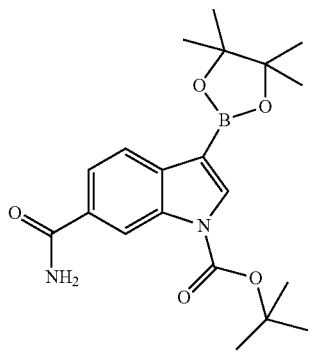 [SMILES: CC(C)(C)OC(=O)n1cc(B2OC(C)(C)C(C)(C)O2)c2ccc(C(N)=O)cc21]

tert-Butyl 3-bromo-6-carbamoyl-indole-1-carboxylate (498.000 mg; 2 mmol; 1 eq.), 4,4,5,5,4',4',5',5'-octamethyl-[2,2']bi[[1,3,2]dioxaborolanyl] (1029.764 mg; 4.055 mmol; 2.00 eq.), potassium acetat (0.380 ml; 6.082 mmol; 3.00 eq.) and bis(triphenylphosphin)-palladium(II)-chlorid (15.2% Pd) (56.927 mg; 0.081 mmol; 0.04 eq.) were added. Under nitrogen tetrahydrofuran (15.000 ml; 185.144 mmol; 91.31 eq.) was added and the reaction mixture was heated to 100° C. for 2 h in the microwave. The reaction mixture was concentrated under reduced pressure. The residue was purified by Flash Chromatography to give 176 mg (22%) of the title compound; HPLC MS (Method G): (M+H) 387.2; (22% boronic acid); (percent area) 78.13%; (22% boronic acid); Rt 2.337 min; (22% boronic acid).

77.5 {(1S,2R)-2-[8-(6-Carbamoyl-1H-indol-3-yl)-pyrido[4,3-d]pyrimidin-2-ylamino]-cyclohexyl}-carbamic acid tert-butyl ester

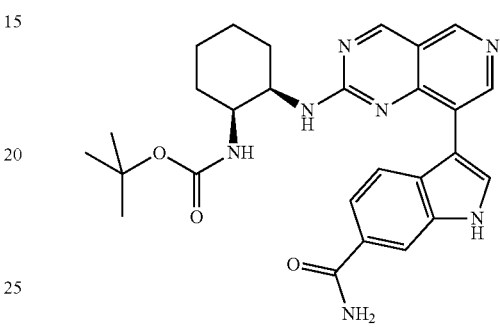

[(1S,2R)-2-(8-Iodo-pyrido[4,3-d]pyrimidin-2-ylamino)-cyclohexyl]-carbamic acid tert-butyl ester (50.00 mg; 0.08 mmol; 1.00 eq.), 6-carbamoyl-3-(4,4,5,5-tetramethyl-[1,3,2]dioxaborolan-2-yl)-indole-1-carboxylic acid tert-butyl ester (61.94 mg; 0.13 mmol; 1.50 eq.), palladium(II) acetate (47% Pd) for synthesis (0.94 mg; 0.00 mmol; 0.05 eq.), 2-dicyclohexylphosphino-2'-6'-dimethoxybiphenyl (3.43 mg; 0.01 mmol; 0.10 eq.) and potassium carbonate (0.01 ml; 0.25 mmol; 3.00 eq.) was dissolved in ethylene glycol dimethyl ether (2.10 ml; 20.27 mmol; 242.71 eq.) and water (0.70 ml; 38.85 mmol; 465.08 eq.). The mixture was heated to 150° C. in the microwave for 45 min, then concentrated. The precipitate was purified by Flash Chromatography to give 18 mg (44%) of the title compound as a yellow solid; HPLC MS (Method G): Rt 1.62 min;

(M+H) 502.3.

77.6 3-[2-((1R,2S)-2-amino-cyclohexylamino)-pyrido[4,3-d]pyrimidin-8-yl]-1H-indole-6-carboxylic acid amide {(1S,2R)-2-[8-(6-Carbamoyl-1H-indol-3-yl)-pyrido[4,3-d]pyrimidin-2-ylamino]-cyclohexyl}-carbamic acid tert-butyl ester (17.70 mg; 0.035 mmol; 1.00 eq.) was dissolved in ethylacetat (4.00 ml; 40.858 mmol; 1176.66 eq.) and hydrochloric acid (1 N) (0.40 ml; 11.190 mmol; 322.27 eq.) and was stirred at rt for 16 h. The solvent was removed in vacuo to give 15 mg (91%) of the title compound as a yellow brown solid; HPLC MS (Method G): Rt 1.214 min; (M+H) 402.1;

$^1$H NMR (500 MHz, DMSO-d$_6$+TFA-d$_1$) δ [ppm] 9.68-9.55 (s, 1H), 9.48-9.28 (s, 1H), 9.06-8.93 (s, 1H), 8.56-8.33 (s, 1H), 8.24-8.09 (d, J=1.3 Hz, 1H), 7.99-7.90 (d, J=8.5 Hz, 1H), 7.84-7.72 (m, 1H), 4.38-4.27 (m, 1H), 3.74-3.61 (m, 1H), 2.01-1.93 (m, 1H), 1.91-1.71 (m, 3H), 1.66-1.38 (m, 4H).

Example 78

Enantiomer 1 of (3-fluoro-piperidin-3-ylmethyl)-[8-(6-trifluoromethyl-1H-indol-3-yl)-pyrido[4,3-d]pyrimidin-2-yl]-amine ("A78")

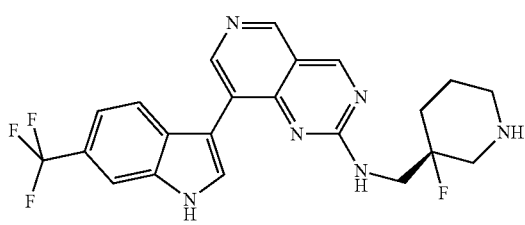 [SMILES: FC(F)(F)c1ccc2c(-c3cncc4cnc(NC[C@@]5(F)CCCNC5)nc34)c[nH]c2c1]

(given absolute configuration is arbitrary).

78.1 1-(p-tolylsulfonyl)-6-(trifluoromethyl)indole

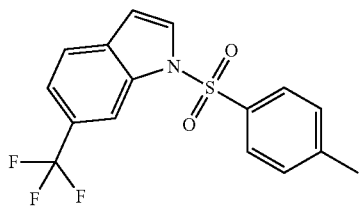 [SMILES: Cc1ccc(S(=O)(=O)n2ccc3ccc(C(F)(F)F)cc32)cc1]

6-Trifluoromethylindole (2.082 g; 10.908 mmol; 1.00 eq.) was dissolved in toluene (30.000 ml; 283.265 mmol; 25.97 eq.). Tetra-n-butylammonium hydrogensulfat (555.541 mg; 1.636 mmol; 0.15 eq.), NaOH solution 32% (30.000 ml; 324.024 mmol; 29.71 eq.) and toluene-4-sulfonylchloride (3.183 g; 16.362 mmol; 1.50 eq.) were added at 0° C. The solution was stirred for 14 h in a thawing ice bath. The reaction mixture was diluted with toluene and water, the organic layer was washed twice with a saturated solution of ammonia and 1× with water. The organic layer was dried over MgSO$_4$, filtered and concentrated under reduced pressure. This gives 4 g (95%) of the title compound as a brown solid; HPLC MS (Method G): (M+H) 340; Rt 2.601 min.

78.2 3-bromo-1-(toluene-4-sulfonyl)-6-trifluoromethyl-1H-indole

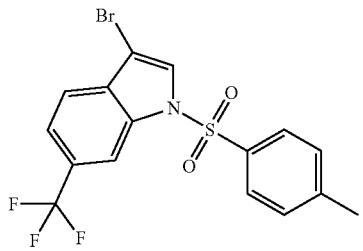 [SMILES: Cc1ccc(S(=O)(=O)n2cc(Br)c3ccc(C(F)(F)F)cc32)cc1]

1-(Toluene-4-sulfonyl)-6-trifluoromethyl-1H-indole (3.646 g; 10.745 mmol; 1.00 eq.) was dissolved in acetonitril (50.000 ml; 957.299 mmol; 89.10 eq.) and Cu(II) Br (7.200 g; 32.234 mmol; 3.00 eq.) was added. The solution was stirred at rt for 5 days. The mixture was diluted with 60 ml 7M ammonia (approx. 12.5%) and extracted with ethyl acetate and the organic layer was washed with water, dried over MgSO$_4$, filtered and concentrated under reduced pressure. The precipitate was suspended in DCM/MeOH and filtered and dried for 14 h to give 3 g (68%) of the title compound as an off-white solid; HPLC (Method G): Rt 2.81 min.

78.3 Enantiomer 1 and Enantiomer 2 of 3-fluoro-3-[(8-iodo-pyrido[4,3-d]pyrimidin-2-ylamino)-methyl]-piperidine-1-carboxylic acid tert-butyl ester

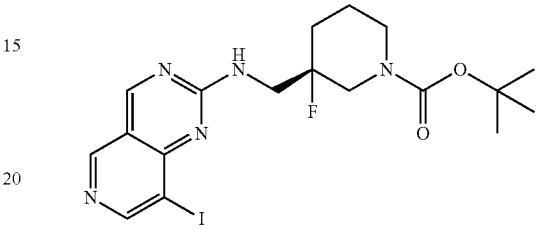

2-Chloro-8-iodo-pyrido[4,3-d]pyrimidine (962.95 mg; 2.045 mmol; 1.000 eq.) was dissolved in triethylamine (0.43 ml; 3.068 mmol; 1.500 eq.) and ethanol (2.00 ml; 34.297 mmol; 16.771 eq.), Then 3-aminomethyl-3-fluoro-piperidine-1-carboxylic acid tert-butyl ester (535.56 mg; 2.045 mmol; 1.000 eq.) was added and the reaction mixture was heated to 120° C. for 5 minutes in the microwave. The reaction mixture was poured into water and filtered. The precipitate was purified by flash chromatography to give 169 mg racemate as yellow solid; HPLC MS (Method G): Rt 1.83 min, MH+488.1. The enantiomers were separated by chiral SFC (column: ChiralCel OJ-H, eluent: CO$_2$, methanol (20%), wave length: 220 nm, flow: 5 ml/min.

78.3.1 Enantiomer 1: (S)-3-fluoro-3-[(8-iodo-pyrido[4,3-d]pyrimidin-2-ylamino)-methyl]-piperidine-1-carboxylic acid tert-butyl ester (81.80 mg; 0.168 mmol), this stereoisomere eluates first from column Chiralcel OJ-H with solvent system CO$_2$+20% methanol; absolute configuration arbitrary. 78.3.2 Enantiomer 2: (R)-3-fluoro-3-[(8-iodo-pyrido[4,3-d]pyrimidin-2-ylamino)-methyl]-piperidine-1-carboxylic acid tert-butyl ester (64.50 mg; 0.132 mmol) brown solid, the stereoisomer eluates second from column Chiralcel OJ-H with solvent system CO$_2$+20% methanol; absolute configuration arbitrary.

78.4 3-(4,4,5,5-tetramethyl-[1,3,2]dioxaborolan-2-yl)-1-(toluene-4-sulfonyl)-6-trifluoromethyl-1H-indole

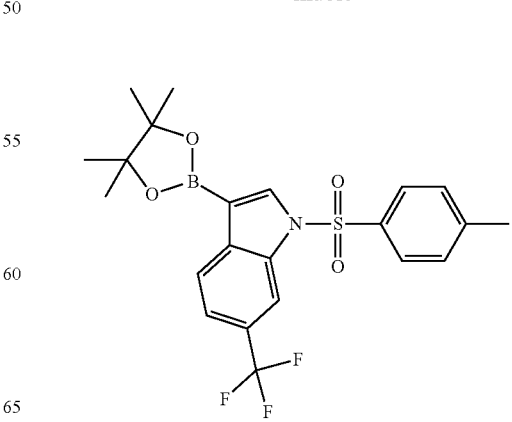

85

4,4,5,5,4',4',5',5'-Octamethyl-[2,2']bi[[1,3,2]dioxaborolanyl] (2.42 g; 9.549 mmol; 1.300 eq.), potassium acetate (2.16 g; 22.035 mmol; 3.000 eq.) and bis(triphenylphosphine)palladium(II) chloride (15.2% Pd) (206.23 mg; 0.294 mmol; 0.040 eq.) were added and dissolved in tetrahydrofuran (15.00 ml; 185.144 mmol; 25.206 eq.) while purging the suspension with nitrogen. 3-Bromo-1-(toluene-4-sulfonyl)-6-trifluoromethyl-1H-indole (3.07 g; 7.345 mmol; 1.000 eq.) was added and the reaction mixture was heated to 100° C. for 2 h in the microwave. The reaction mixture was concentrated under reduced pressure. The residue was purified by Flash Chromatography to give 1 g (31%) of the title compound as a white solid; HPLC MS(Method G): (M+H) 466.1/384.1; (pinacole ester/free boronic acid); (percent area) 63.8/36.2%; Rt 2.946/2.312 min.

78.5 Enantiomer 1 of 3-fluoro-3-({8-[1-(toluene-4-sulfonyl)-6-trifluoromethyl-1H-indol-3-yl]-pyrido[4,3-d]pyrimidin-2-ylamino}-methyl)-piperidine-1-carboxylic acid tert-butyl ester

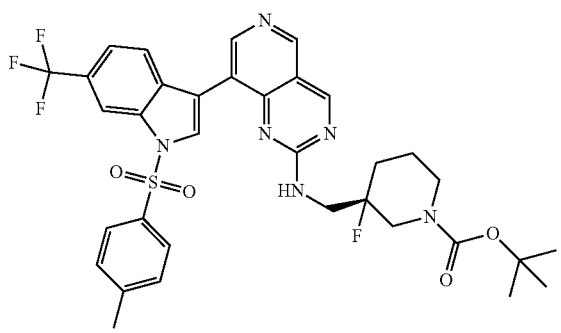 [SMILES: Cc1ccc(S(=O)(=O)n2cc(-c3cncc4cnc(NC[C@@]5(F)CCCN(C(=O)OC(C)(C)C)C5)nc34)c3ccc(C(F)(F)F)cc32)cc1]

(Given absolute configuration is arbitrary).

(S)-3-Fluoro-3-[(8-iodo-pyrido[4,3-d]pyrimidin-2-ylamino)-methyl]-piperidine-1-carboxylic acid tert-butyl ester from example 78.3.1 (81.80 mg; 0.168 mmol; 1.000 eq.), 3-(4,4,5,5-tetramethyl-[1,3,2]dioxaborolan-2-yl)-1-(toluene-4-sulfonyl)-6-trifluoromethyl-1H-indole (93.73 mg; 0.201 mmol; 1.200 eq.), palladium(II) acetate (47% Pd) (1.88 mg; 0.008 mmol; 0.050 eq.), 2-dicyclohexylphosphino-2',6'-dimethoxybiphenyl (6.89 mg; 0.017 mmol; 0.100 eq.) and potassium carbonate (68.39 mg; 0.495 mmol; 2.948 eq.) were added and suspended in ethylene glycol dimethyl ether (2.13 ml; 20.534 mmol; 122.328 eq.) and water (0.71 ml; 39.346 mmol; 234.400 eq.) while purging nitrogen through the mixture. The reaction mixture was heated for 45 min at 150° C. in the microwave. The mixture was concentrated under reduced pressure and purified by Flash Chromatography to give 68 mg (29%) of the title compound as mixture with the detosylated compound as a green solid; LC/MS(Method G): Rt 2.427 min; (M+H) 699.3 and for the detosylated compound Rt 2.08 min, MH+545.3).

86

78.6 Enantiomer 1 of (3-fluoro-piperidin-3-ylmethyl)-{8-[1-(toluene-4-sulfonyl)-6-trifluoromethyl-1H-indol-3-yl]-pyrido[4,3-d]pyrimidin-2-yl}-amine

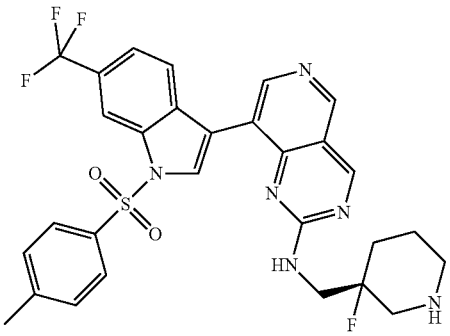 [SMILES: Cc1ccc(S(=O)(=O)n2cc(-c3cncc4cnc(NC[C@@]5(F)CCCNC5)nc34)c3ccc(C(F)(F)F)cc32)cc1]

Example 78.5 (68 mg) was dissolved in dichloromethane (500.00 μl; 7.830 mmol; 160.586 eq.) and trifluoroacetic acid (37.56 μl; 0.488 mmol; 10.000 eq.) was added and the solution was stirred at rt for 14 h. Trifluoroacetic acid (20.00 μl; 0.260 mmol; 5.324 eq.) was added and stirred for 14 h. The solvent was evaporated under reduced pressure to give 56 mg (90%) of the title compound as a yellow solid; LC/MS (Method G): Rt 1.857 min; (M+H) 599.2.

78.7 Enantiomer 1 of (3-fluoro-piperidin-3-ylmethyl)-[8-(6-trifluoromethyl-1H-indol-3-yl)-pyrido[4,3-d]pyrimidin-2-yl]-amine

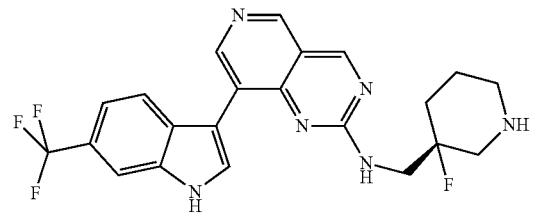 [SMILES: FC(F)(F)c1ccc2c(-c3cncc4cnc(NC[C@@]5(F)CCCNC5)nc34)c[nH]c2c1]

Example 78.6 (56 mg) was dissolved in ethanol (4.00 ml; 68.594 mmol), then tetrahydrofuran (1.00 ml; 12.343 mmol) and sodium hydroxide pellets (35.02 mg; 0.876 mmol; 20.000 eq.) were added. The solution was heated to 50° C. for 14 h. The solvent was evaporated under reduced pressure. The residue was treated with water, filtered, and washed with water. The precipitate was suspended in diethyl ether and extracted with 1N HCl 2 times. The solvent of the combined aqueous layers was removed under vacuo to give the title compound as a orange solid; $^1$H NMR (500 MHz, DMSO-$d_6$) δ [ppm] 12.35 (s, 1H), 9.57 (s, 1H), 9.56-9.49 (m, 1H), 9.33 (s, 1H), 9.28-9.19 (m, 1H), 8.92 (s, 1H), 8.63 (q, J=11.3, 1H), 8.46 (d, J=2.8, 1H), 8.02 (d, J=8.5, 1H), 7.91 (s, 1H), 7.46-7.42 (m, 1H), 3.81-3.65 (m, 2H), 3.37-3.28 (m, 1H), 3.20-3.11 (m, 1H), 3.09-2.94 (m, 1H), 2.71 (q, J=11.9, 1H), 1.99-1.53 (m, 4H); LC/MS (Method G): (percent area) 100%; Rt 1.496 min; (M+H) 445.2.

Example 79

Enantiomer 2 of (3-fluoro-piperidin-3-ylmethyl)-[8-(6-trifluoromethyl-1H-indol-3-yl)-pyrido[4,3-d]pyrimidin-2-yl]-amine ("A79")

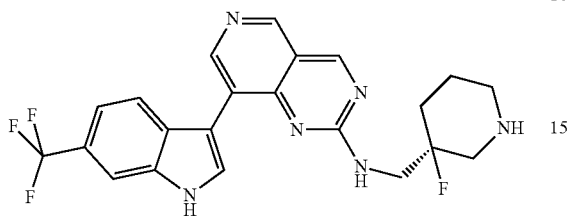

(given absolute configuration is arbitrary).

79.1 Enantiomer 2 of 3-fluoro-3-({8-[1-(toluene-4-sulfonyl)-6-trifluoromethyl-1H-indol-3-yl]-pyrido[4,3-d]pyrimidin-2-ylamino}-methyl)-piperidine-1-carboxylic acid tea-butyl ester

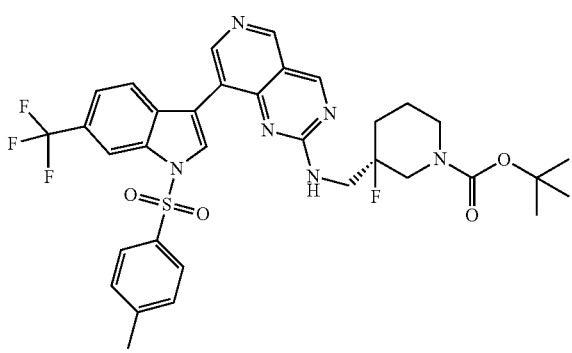 [SMILES: Cc1ccc(S(=O)(=O)n2cc(-c3cncc4cnc(NC[C@]5(F)CCCN(C(=O)OC(C)(C)C)C5)nc34)c3ccc(C(F)(F)F)cc32)cc1]

Example 78.3.2 (enantiomer 2; 64.50 mg), 3-(4,4,5,5-tetramethyl-[1,3,2]dioxaborolan-2-yl)-1-(toluene-4-sulfonyl)-6-trifluoromethyl-1H-indole (73.90 mg; 0.159 mmol; 1.200 eq.), palladium(II) acetate (47% Pd) (1.49 mg; 0.007 mmol; 0.050 eq.), 2-dicyclohexylphosphino-2',6'-dimethoxybiphenyl (5.43 mg; 0.013 mmol; 0.100 eq.) and potassium carbonate (0.02 ml; 0.390 mmol; 2.948 eq.) were added and suspended in ethylene glycol dimethyl ether (1.68 ml; 16.191 mmol; 122.328 eq.) and water (0.56 ml; 31.025 mmol; 234.400 eq.) while purging nitrogen through the suspension. The reaction mixture was heated for 45 min at 150° C. in the microwave. The reaction mixture was concentrated under reduced pressure. The residue was purified by Flash Chromatography to give 62 mg (34%) of the title compound as a mixture with the detosylated product as a green solid; LC/MS(Method G): Rt 2.425 min; (M+H) 699.3.

79.2 Enantiomer 2 of (3-fluoro-piperidin-3-ylmethyl)-{8-[1-(toluene-4-sulfonyl)-6-trifluoromethyl-1H-indol-3-yl]-pyrido[4,3-d]pyrimidin-2-yl}-amine

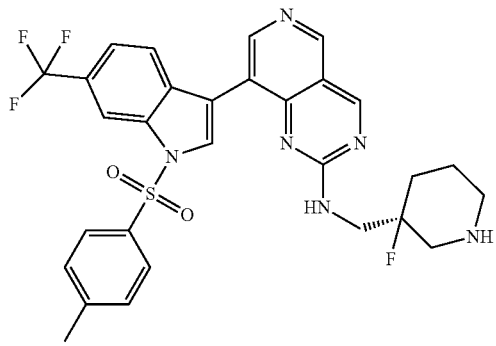 [SMILES: Cc1ccc(S(=O)(=O)n2cc(-c3cncc4cnc(NC[C@]5(F)CCCNC5)nc34)c3ccc(C(F)(F)F)cc32)cc1]

Example 79.1 (62 mg) was dissolved in dichloromethane (500.00 µl; 7.830 mmol; 171.672 eq.). Trifluoroacetic acid (35.14 µl; 0.456 mmol; 10.000 eq.) was added and the solution was stirred at rt for 2 days. The solvent was evaporated under reduced pressure to give 48 mg (86%) of the title compound as mixture with the detosylated product as a yellow green solid; LC/MS (Method G): Rt 1.867 min; (M+H) 599.2.

79.2 Enantiomer 2 of (3-fluoro-piperidin-3-ylmethyl)-[8-(6-trifluoromethyl-1H-indol-3-yl)-pyrido[4,3-d]pyrimidin-2-yl]-amine 48 mg example 79.2 was dissolved in ethanol (4.00 ml; 68.594 mmol) and tetrahydrofuran (1.00 ml; 12.343 mmol) and sodium hydroxide pellets (31.24 mg; 0.781 mmol; 20.000 eq.) were added. The solution was heated to 50° C. for 14 h. The solvent was evaporated under reduced pressure. The residue suspended in water, filtered and washed with water. The precipitate was dissolved in diethyl ether and extracted with 1N HCl 2 times. The solvent of the combined aqueous layers were removed under vacuo to give 44 mg (234%) of the title compound as an orange solid; $^1$H NMR (500 MHz, DMSO-$d_6$) δ [ppm] 12.27-12.21 (m, 1H), 9.54 (s, 1H), 9.38-9.25 (m, 2H), 9.14-8.96 (m, 1H), 8.92 (s, 1H), 8.57 (q, J=11.2, 1H), 8.42 (d, J=2.7, 1H), 8.01 (d, J=8.5, 1H), 7.90 (s, 1H), 7.47-7.41 (m, 1H), 3.83-3.65 (m, 2H), 3.35-3.26 (m, 1H), 3.15 (d, J=12.4, 1H), 3.08-2.90 (m, 1H), 2.68 (q, J=12.0, 1H), 1.90-1.52 (m, 4H); LC/MS (Method G): (percent area) 100%; Rt 1.499 min; (M+H) 445.2.

Example 80

3-(2-cyclohexylamino-pyrido[4,3-d]pyrimidin-8-yl)-1H-indole-6-carbonitrile ("A80")

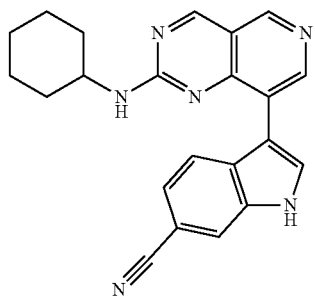 [SMILES: N#Cc1ccc2c(-c3cncc4cnc(NC5CCCCC5)nc34)c[nH]c2c1]

80.1 cyclohexyl-(8-iodo-pyrido[4,3-d]pyrimidin-2-yl)-amine

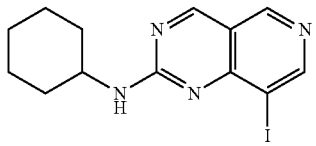 [SMILES: Ic1cncc2cnc(NC3CCCCC3)nc12]

8-Iodo-2-methylsulfanyl-pyrido[4,3-d]pyrimidine (378.00 mg; 1.25 mmol; 1.00 eq.) and cyclohexylamine (1.42 ml; 12.47 mmol; 10.00 eq.) were heated at 120° C. for 2 h. The solvent was removed in vacuo and the precipitate purified by flash chromatography to give 97 mg (19%) of the title compound as a white yellow solid; HPLC MS (Method G): Rt 1.79 min; (M+H) 355.1.

80.2 3-(2-cyclohexylamino-pyrido[4,3-d]pyrimidin-8-yl)-1H-indole-6-carbonitrile Cyclohexyl-(8-iodo-pyrido[4,3-d]pyrimidin-2-yl)-amine (116 mg; 1 eq.), 1-BOC-6-cyanoindole-3-boronic acid, pinacol ester (180.43 mg; 0.49 mmol; 1.50 eq.), palladium(II) acetate (47% Pd) (3.67 mg; 0.02 mmol; 0.05 eq.), potassium carbonate (0.06 ml; 0.98 mmol; 3.00 eq.) and dicyclohexyl-(2',6'-dimethoxybiphenyl-2-yl)-phosphane (13.41 mg; 0.03 mmol; 0.10 eq.) were dissolved in ethylene glycol dimethyl ether (7.50 ml; 48.27 mmol; 147.76 eq.) and water (2.50 ml; 88.79 mmol; 271.81 eq.). The mixture was heated in the microwave to 150° C. for 45 minutes. The solvent was removed under vacuo and the precipitate purified by flash chromatography to give 98 mg (81%) of the title compound as a yellow beige solid; HPLC MS (Method G): Rt 1.79 min; (M+H) 369.2, $^1$H NMR (500 MHz, DMSO-d$_6$) δ [ppm] 12.13-12.09 (m, 1H), 9.32-9.25 (s, 1H), 8.97-8.92 (s, 1H), 8.87-8.83 (s, 1H), 8.35-8.30 (d, J=2.7 Hz, 1H), 8.07-7.86 (m, 3H), 7.43-7.36 (m, 1H), 3.73-3.62 (m, 1H), 1.93-1.87 (m, 2H), 1.77-1.64 (m, 2H), 1.64-1.52 (m, 1H), 1.41-1.06 (m, 6H).

Example 81

(1S,2R)—N-[8-(7-fluoro-1H-indol-2-yl)-pyrido[4,3-d]pyrimidin-2-yl]-cyclohexane-1,2-diamine ("A81")

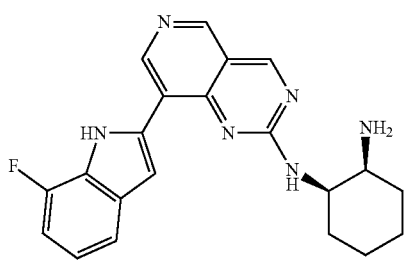 [SMILES: N[C@H]1CCCC[C@H]1Nc1ncc2cncc(-c3cc4cccc(F)c4[nH]3)c2n1]

81.1 tert-butyl N-[(1S,2R)-2-[[8-(7-fluoro-1H-indol-2-yl)pyrido[4,3-d]pyrimidin-2-yl]amino]cyclohexyl] carbamate

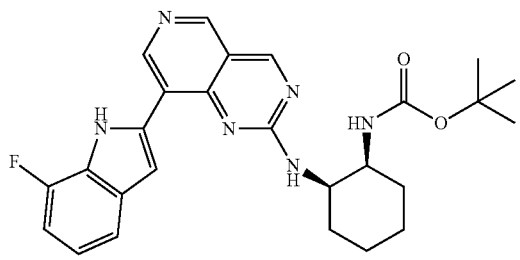 [SMILES: CC(C)(C)OC(=O)N[C@H]1CCCC[C@H]1Nc1ncc2cncc(-c3cc4cccc(F)c4[nH]3)c2n1]

[(1S,2R)-2-(8-Iodo-pyrido[4,3-d]pyrimidin-2-ylamino)-cyclohexyl]-carbamic acid tert-butyl ester (100.000 mg; 0.213 mmol; 1.00 eq.), N—(BOC)-7-fluoroindole-2-boronic acid (89.195 mg; 0.320 mmol; 1.50 eq.), palladium(II)-acetat (47% Pd) (2.392 mg; 0.011 mmol; 0.05 eq.), 2-dicyclohexylphosphino-2',6'-dimethoxybiphenyl (8.747 mg; 0.021 mmol; 0.10 eq.) and potassium carbonate (88.343 mg; 0.639 mmol; 3.00 eq.) were added into a 5 ml microwave vessel. Ethylenglycoldimethylether (2.500 ml; 24.134 mmol; 113.27 eq.) and water (0.800 ml; 44.395 mmol; 208.36 eq.) were added and the suspension was purged with nitrogen. The reaction mixture was heated in the microwave at 130° C. for 45 min. N—(BOC)-7-fluoroindole-2-boronic acid (89.195 mg; 0.320 mmol; 1.50 eq.), palladium(II)-acetat (47% Pd) (2.392 mg; 0.011 mmol; 0.05 eq.) and 2-dicyclohexylphosphino-2',6'-dimethoxybiphenyl (8.747 mg; 0.021 mmol; 0.10 eq.) were added and heated in the microwave for further 30 min. at 150° C. The reaction mixture was diluted with DMF, filtered with an Anatop 25 inorganic membrane filter and the solution was purified by preparative HPLC to give 10 mg (10%) of the title compound; HPLC MS (Method G): (M+H) 477.3; (percent area) 100%; Rt 2.148 min.

81.2 (1S,2R)—N-[8-(7-fluoro-1H-indol-2-yl)-pyrido[4,3-d]pyrimidin-2-yl]-cyclohexane-1,2-diamine tert-Butyl N-[(1S,2R)-2-[[8-(7-fluoro-1H-indol-2-yl)pyrido[4,3-d]pyrimidin-2-yl]amino]cyclohexyl]carbamate (10.000 mg; 20.984 μmol; 1.00 eq.) was suspended in ethylacetat (300.000 μl; 3.064 mmol; 146.03 eq.). Hydrochloric acid (1 N) (209.843 μl; 209.843 μmol; 10.00 eq.) was added. The mixture was stirred at RT for 21 h and stirred at 50° C. for 3 h. The solvent was removed under vacuo to give 9 mg (98%) of the title compound as a yellow solid; HPLC (Method J): (percent area) 93.35%; Rt 2.31 min.; HPLC MS (Method G): (M+H) 377.3; Rt 1.303 min.

Example 82

(1S,2R)—N-[5-difluoromethyl-8-(6-trifluoromethyl-1H-indol-3-yl)-pyrido[4,3-d]pyrimidin-2-yl]-cyclohexane-1,2-diamine ("A82")

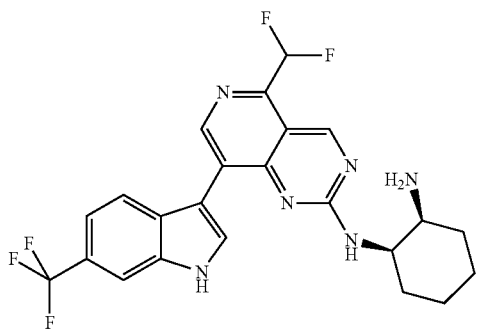 [SMILES: N[C@H]1CCCC[C@H]1Nc1ncc2c(C(F)F)ncc(-c3c[nH]c4cc(C(F)(F)F)ccc34)c2n1]

82.1 5-difluoromethyl-2-methylsulfanyl-pyrido[4,3-d]pyrimidine

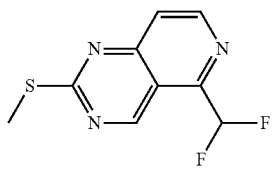

2-Methylsulfanyl-pyrido[4,3-d]pyrimidine (184.32 mg; 1.040 mmol; 1.000 eq.) was dissolved in dichloromethane (4.00 ml; 62.637 mmol; 60.228 eq.). Water (1.60 ml) and bis(((difluoromethyl)sulfinyl)oxy)zinc (530.00 mg; 1.793 mmol; 1.724 eq.) were added at rt. The reaction mixture was cooled down in an ice bath and trifluoroacetic acid (80.12 µl; 1.040 mmol; 1.000 eq.) was added followed by slow addition of tert-Butyl hydroperoxide, 70% aqueous solution (743.86 µl; 5.200 mmol; 5.000 eq.). The reaction mixture was allowed to warm to rt and stirred for 14 h. tert-Butyl hydroperoxide, 70% aqueous solution (743.86 µl; 5.200 mmol; 5.000 eq.) was added and it was stirred for 14 h again. The reaction was partitioned between DCM and saturated sodium bicarbonate solution. The organic layer was separated and the aqueous layer was extracted with DCM one more time. The combined organic layers were dried over MgSO$_4$ and concentrated under reduced pressure. The precipitate was purified by flash chromatography to give 23 mg (10%) of the title compound as a white solid; LC/MS (Method G): (percent area) 100%; Rt 1.765 min; (M+H) 228.

82.2 5-difluoromethyl-8-iodo-2-methylsulfanyl-pyrido[4,3-d]pyrimidine

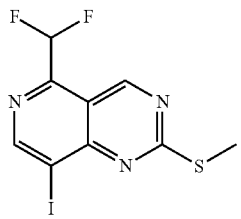 [SMILES: CSc1ncc2c(C(F)F)ncc(I)c2n1]

5-Difluoromethyl-2-methylsulfanyl-pyrido[4,3-d]pyrimidine (23.00 mg; 0.101 mmol; 1.000 eq.) was dissolved in dry N,N-dimethylformamide (500.00 µl; 0.006 mol; 63.528 eq.). Trifluoroacetic acid (9.36 µl; 0.121 mmol; 1.200 eq.) and N-iodosuccinimide (27.33 mg; 0.121 mmol; 1.200 eq.) were added and the reaction mixture was stirred at 50° C. for 3 days. The reaction was treated with water and 0.1 N sodiumthiosulfate solution and stirred for about 20 minutes while cooling down to room temperature. The precipitate was filtered off and washed with water. This wet cake was treated with DCM and evaporated under reduced pressure to give 25 mg (70%) of the title compound as a yellow solid; LC/MS (Method G): (percent area) 100%; Rt 2.238 min; (M+H) 353.9.

82.3 [(1S,2R)-2-(5-difluoromethyl-8-iodo-pyrido[4,3-d]pyrimidin-2-ylamino)-cyclohexyl]-carbamic acid tert-butyl ester

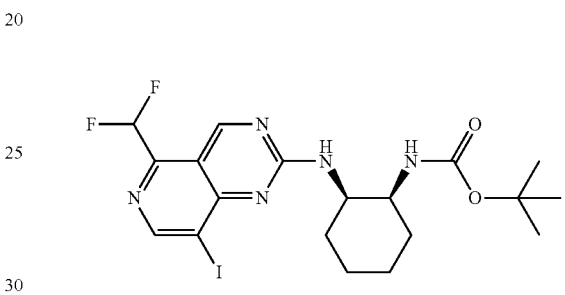

To the solution of 2-chloro-5-difluoromethyl-8-iodo-pyrido[4,3-d]pyrimidine (24.00 mg; 0.070 mmol; 1.000 eq.) in acetonitrile, triethylamin (107.17 µl; 0.773 mmol; 11.000 eq.) and ethanol (46.79 µl; 0.802 mmol; 11.417 eq.) were added and treated with ((1S,2R)-2-amino-cyclohexyl)-carbamic acid tert-butyl ester (15.81 mg; 0.074 mmol; 1.050 eq.). The reaction mixture was heated in the microwave at 120° C. for 5 min. The reaction mixture was evaporated under reduced pressure. The residue was treated with water and filtered to give 21 mg (58%) of the title compound as a yellow solid; LC/MS (Method G): (percent area) 100%; Rt 2.459 min; (M+H) 520.1.

82.4 ((1S,2R)-2-{5-difluoromethyl-8-[1-(toluene-4-sulfonyl)-6-trifluoromethyl-1H-indol-3-yl]-pyrido[4,3-d]pyrimidin-2-ylamino}-cyclohexyl)-carbamic acid tert-butyl ester

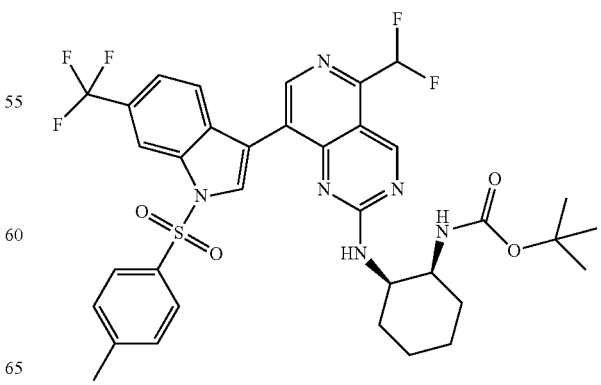

[(1S,2R)-2-(5-difluoromethyl-8-iodo-pyrido[4,3-d]pyrimidin-2-ylamino)-cyclohexyl]-carbamic acid tert-butyl ester (21.00 mg; 0.040 mmol; 1.000 eq.), 3-(4,4,5,5-tetramethyl-[1,3,2]dioxaborolan-2-yl)-1-(toluene-4-sulfonyl)-6-trifluoromethyl-1H-indole (22.58 mg; 0.049 mmol; 1.200 eq.), palladium(II)-acetat (47% Pd) (0.45 mg; 0.002 mmol; 0.050 eq.), 2-dicyclohexylphosphino-2',6'-dimethoxybiphenyl (1.66 mg; 0.004 mmol; 0.100 eq.) and potassium carbonate (16.48 mg; 0.119 mmol; 2.948 eq.) were added and suspended in ethylenglycoldimethylether (0.42 ml; 4.044 mmol; 100.000 eq.) and water (0.15 ml; 8.087 mmol; 200.000 eq.) while purging nitrogen through the suspension. The suspension was heated in the microwave for 45 min at 150° C. The reaction mixture was concentrated under reduced pressure and the precipitate purified by flash chromatography to give 10 mg (33%) of the title compound as a yellow solid; LC/MS (Method G): (percent area) 100%; Rt 2.882 min; (M+H) 753.3 and 5 mg of the detosylated compound as a yellow solid; LC/MS (Method G): (percent area) 100%; Rt 2.509 min; (M+H) 577.2.

82.5 (1S,2R)—N-{5-fifluoromethyl-8-[1-(toluene-4-sulfonyl)-6-trifluoromethyl-1H-indol-3-yl]-pyrido[4,3-d]pyrimidin-2-yl}-cyclohexane-1,2-diamine trifluoroacetate

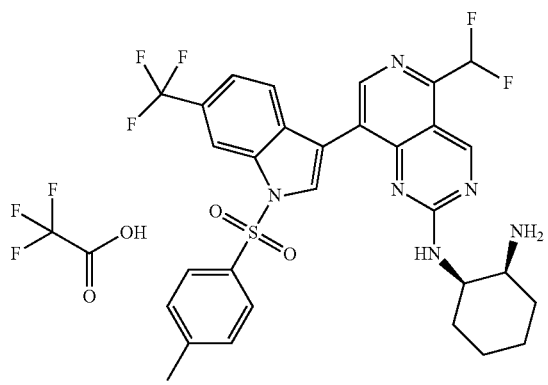 [SMILES: O=C(O)C(F)(F)F ; Cc1ccc(S(=O)(=O)n2cc(-c3cnc(C(F)F)c4cnc(N[C@@H]5CCCC[C@@H]5N)nc34)c3ccc(C(F)(F)F)cc32)cc1]

From Example 82.4 ((1S,2R)-2-{5-difluoromethyl-8-[1-(toluene-4-sulfonyl)-6-trifluoromethyl-1H-indol-3-yl]-pyrido[4,3-d]pyrimidin-2-ylamino}-cyclohexyl)-carbamic acid tert-butyl ester (9.80 mg; 0.013 mmol; 1.000 eq.) and {(1S,2R)-2-[5-difluoromethyl-8-(6-trifluoromethyl-1H-indol-3-yl)-pyrido[4,3-d]pyrimidin-2-ylamino]-cyclohexyl}-carbamic acid tert-butyl ester (4.70 mg; 0.008 mmol; 0.608 eq.) were dissolved in dichloromethane (300.00 µl; 2.302 mmol). Trifluoroacetic acid (10.33 µl; 0.134 mmol; 10.000 eq.) was added and the resulting solution was stirred at rt for 14 h. The solvent was evaporated under reduced pressure to give 17 mg of the title compound as a mixture with the detosylated form as an orange solid; LC/MS (Method G): Rt 2.361 min; (M+H) 631.2.

82.6 (1S,2R)—N-[5-difluoromethyl-8-(6-trifluoromethyl-1H-indol-3-yl)-pyrido[4,3-d]pyrimidin-2-yl]-cyclohexane-1,2-diamine From example 82.5 17 mg were dissolved in ethanol (2.40 ml; 41.157 mmol; 3168.352 eq.) and tetrahydrofuran (0.70 ml; 8.640 mmol; 665.137 eq.). Sodium hydroxide pellets (18.26 mg; 0.457 mmol; 35.145 eq.) were added and the solution was stirred at 50° C. for 2.5 h. The reaction mixture was concentrated under reduced pressure. The residue was treated with water and filtered to give 6 mg (97%) of the title compound as a yellow solid; LC/MS (Method G): (percent area) 100%; Rt 2.006 min; (M+H) 477.2;

$^1$H NMR (700 MHz, DMSO-$d_6$) δ [ppm] 12.41-11.86 (s, 1H), 9.78-9.27 (s, 1H), 8.97-8.80 (s, 1H), 8.48-8.25 (s, 1H), 8.07-7.72 (m, 3H), 7.50-7.26 (m, 2H), 3.86-3.79 (d, J=8.5 Hz, 1H), 3.12-2.96 (m, 1H), 1.74-1.06 (m, 8H).

Example 83

3-[2-(2-amino-3,3,3-trifluoro-propylamino)-pyrido[4,3-d]pyrimidin-8-yl]-1H-indole-6-carbonitrile ("A83")

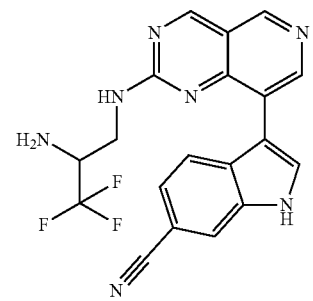 [SMILES: N#Cc1ccc2c(-c3cncc4cnc(NCC(N)C(F)(F)F)nc34)c[nH]c2c1]

83.1 3,3,3-trifluoro-N1-(8-iodo-pyrido[4,3-d]pyrimidin-2-yl)-propane-1,2-diamine

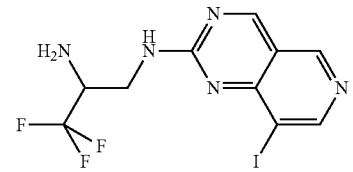 [SMILES: NC(CNc1ncc2cncc(I)c2n1)C(F)(F)F]

2-Chloro-8-iodo-pyrido[4,3-d]pyrimidine (941.76 mg; 2.00 mmol; 1.00 eq.), 3,3,3-trifluoro-propane-1,2-diamine hydrochloride (2) (422.14 mg; 2.10 mmol; 1.05 eq.), 1,4-dioxane (9.00 ml; 105.22 mmol; 52.61 eq.) and triethylamine (1.16 ml; 8.40 mmol; 4.20 eq.) were combined and heated in the microwave on 120° C. for 10 min. The solvent was removed in vacuo and the precipitate purified by flash chromatography to give 77 mg (6%) of the title compound as a yellow brown solid; HPLC MS (Method G): Rt 1.19 min; (M+H) 384.

83.2 3-[2-(2-amino-3,3,3-trifluoro-propylamino)-pyrido[4,3-d]pyrimidin-8-yl]-1H-indole-6-carbonitrile 3,3,3-Trifluoro-N1-(8-iodo-pyrido[4,3-d]pyrimidin-2-yl)-propane-1,2-diamine (77.00 mg; 0.11 mmol; 1.00 eq.), 1-BOC-6-cyanoindole-3-boronic acid, pinacol ester (63.39 mg; 0.17 mmol; 1.50 eq.), palladium(II) acetate (47% Pd) (1.80 mg; 0.01 mmol; 0.07 eq.), 2-dicyclohexylphosphino-2',6'-dimethoxybiphenyl (6.60 mg; 0.02 mmol; 0.14 eq.), potassium carbonate (0.02 ml; 0.36 mmol; 3.11 eq.), ethylene glycol dimethyl ether (1.78 ml; 17.21 mmol; 150.00 eq.)

and water (0.62 ml; 34.43 mmol; 300.00 eq.) were heated in the microwave for 45 min on 150° C. 1-BOC-6-cyanoindole-3-boronic acid, pinacol ester (63.39 mg (63.4 mg), 1.8 mg palladium(II)acetate and 6.6 mg 2-dicyclohexylphosphino-2',6'-dimethoxy biphenyl were added to the mixture. The mixture was heated in the microwave for 45 min to 150° C. The solvent was removed in vacuo and the precipitate purified by reversed phase to give 13 mg of the title compound as a yellow solid; HPLC MS (Method G): (percent area) 100%; Rt 1.32 min; (M+H) 398.2;

$^1$H NMR (500 MHz, DMSO-d$_6$+TFA-d$_1$) δ [ppm] 9.69 (s, 1H), 9.54-9.47 (m, 1H), 9.02-8.93 (m, 1H), 8.43 (s, 1H), 8.11-8.05 (m, 1H), 7.94 (d, J=8.37 Hz, 1H), 7.51 (s, 1H), 4.48-4.34 (m, 1H), 4.04 (d, J=18.84 Hz, 1H), 3.73 (d, J=23.64 Hz, 1H).

Example 85

3-[2-((cis)-2-amino-cyclohexylamino)-5-methyl-pyrido[4,3-d]pyrimidin-8-yl]-1H-indole-6-carbonitrile ("A85")

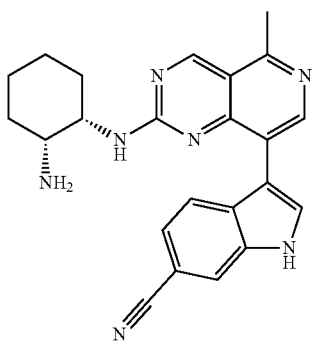 [SMILES: Cc1ncc(-c2c[nH]c3cc(C#N)ccc23)c2nc(N[C@H]3CCCC[C@H]3N)ncc12]

85.1 3-(2-methylsulfanyl-5-oxo-5,6-dihydro-pyrido[4,3-d]pyrimidin-8-yl)-1H-indole-6-carbonitrile

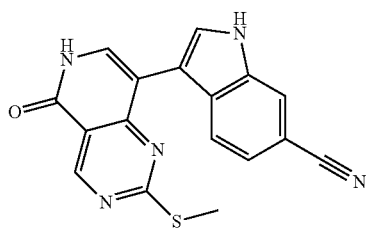 [SMILES: CSc1ncc2c(=O)[nH]cc(-c3c[nH]c4cc(C#N)ccc34)c2n1]

In a microwave vessel 8-iodo-2-methylsulfanyl-6H-pyrido[4,3-d]pyrimidin-5-one (1000.000 mg; 3.134 mmol; 100.00 mol %), 1-BOC-6-cyanoindole-3-boronic acid, pinacol ester (1201.976 mg; 3.134 mmol; 100.00 mol %) and tripotassium phosphate trihydrate (1995.463 mg; 9.401 mmol; 300.00 mol %) were suspended in tetrahydrofuran (35.000 ml) and water (5.000 ml). Under nitrogen [2-(2-aminophenyl)phenyl]-[dicyclohexyl-[2-(2,4,6-triisopropyl-phenyl)-phenyl]phosphaniumyl]palladium chloride (246.552 mg; 0.313 mmol; 10.00 mol %) were added and heated in the microwave (150° C., 45 min). Under nitrogen 1-BOC-6-cyanoindole-3-boronic acid, pinacol ester (1000.000 mg; 2.607 mmol; 83.20 mol %) were added and heated in the microwave (150° C., 45 min). The solvent was removed in vacuo and the residue dissolved in DCM and water and extracted to give 220 mg (14%) of the title compound as a yellow solid; HPLC (Method J): (percent area) 64.2%; Rt 2.357 min.; LC/MS (Method G): Rt 1.766 min; (M+H) 334.1.

85.2 3-(5-chloro-2-methylsulfanyl-pyrido[4,3-d]pyrimidin-8-yl)-1H-indole-6-carbonitrile

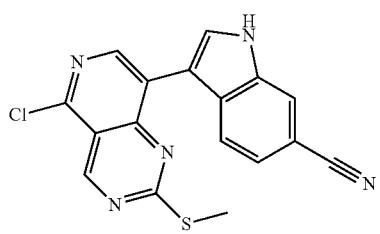 [SMILES: CSc1ncc2c(Cl)ncc(-c3c[nH]c4cc(C#N)ccc34)c2n1]

Phosphorylchlorid (5.000 ml; 55.435 mmol; 13084.36 mol %) was added to 3-(2-methylsulfanyl-5-oxo-5,6-dihydro-pyrido[4,3-d]pyrimidin-8-yl)-1H-indole-6-carbonitrile (220.000 mg; 0.424 mmol; 100.00 mol %). The suspension was stirred at 110° C. for 3 h. The solvent was removed in vacuo, toluene added and removed in vacuo. The residue was suspended in a saturated NaHCO$_3$-solution/ice mixture and filtered to give 220 mg (110%) of the title compound as a brown powder; HPLC (Method J): (percent area) 74.3%; Rt 3.014 min.; LC/MS (Method G): Rt 2.258 min; (M+H) 352.

85.3 3-(5-methyl-2-methylsulfanyl-pyrido[4,3-d]pyrimidin-8-yl)-1H-indole-6-carbonitrile

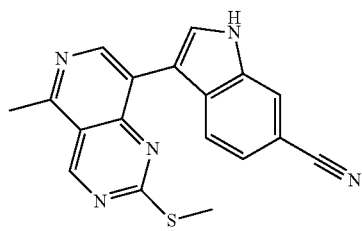 [SMILES: CSc1ncc2c(C)ncc(-c3c[nH]c4cc(C#N)ccc34)c2n1]

3-(5-Chloro-2-methylsulfanyl-pyrido[4,3-d]pyrimidin-8-yl)-1H-indole-6-carbonitrile (220.000 mg; 0.465 mmol; 100.00 mol %), trimethylboroxine, 50 wt % solution in THF (116.652 mg; 0.465 mmol; 100.00 mol %), 2-dicyclohexylphosphino-2',6'-dimethoxybiphenyl (19.664 mg; 0.046 mmol; 10.00 mol %) and cesiumfluoride (141.155 mg; 0.929 mmol; 200.00 mol %) were added in a microwave vessel (2.5 ml). 1,4-Dioxane (5,000 ml) was added. Under nitrogen palladium(II)-acetat (10.431 mg; 0.046 mmol; 10.00 mol %) was added. The vessel was closed with a septum and heated in the microwave (150° C., 45 min), The product was purified by flash chromatography to give 20 mg of the title compound as a yellow solid; LC/MS (Method G): Rt 1.622 min; (M+H) 332.1.

85.4 3-[2-((cis)-2-amino-cyclohexylamino)-5-methyl-pyrido[4,3-d]pyrimidin-8-yl]-1H-indole-6-carbonitrile 3-(5-Methyl-2-methylsulfanyl-pyrido[4,3-d]pyrimidin-8-yl)-1H-indole-6-carbonitrile (20.000 mg; 0.050 mmol;

100.00 mol %) in cis-1,2-cyclohexanediamine (0.061 ml; 0.503 mmol; 1000.00 mol %) was stirred at 100° C. over night. The mixture was dissolved in DMSO and was purified by preparative HPLC. The desired fractions were combined, NaHCO$_3$ was added until pH8 was reached and ACN was removed by vacuo. The aqueous layer was extracted with DCM. The organic layer was dried over Na$_2$SO$_4$, filtered and evaporated to dryness to give 6 mg of the title compound as a yellow solid; HPLC (Method J): (percent area) 100%; Rt 1.857 min.; LC/MS (Method G): Rt 1.438 min; (M+H) 398.3;

1H NMR (400 MHz, CD$_2$Cl$_2$) δ [ppm] 9.28 (s, 1H), 9.03 (s, 1H), 8.72 (s, 1H), 8.04 (s, 1H), 7.89 (d, J=8.73 Hz, 1H), 7.81 (s, 1H), 7.37 (d, J=8.48 Hz, 1H), 6.15 (s, 1H), 3.89 (s, 1H), 3.09 (s, 1H), 2.86 (s, 3H), 1.93-0.97 (m, 8H).

Example 86

2-((cis)-2-amino-cyclohexylamino)-8-(6-trifluoromethyl-1H-indol-3-yl)-6H-pyrido[4,3-d]pyrimidin-5-one ("A86")

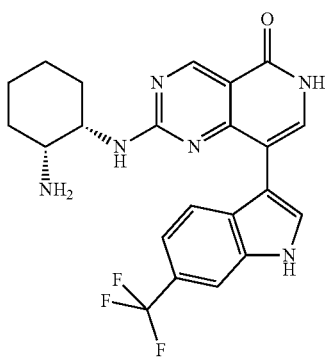 [SMILES: N[C@@H]1CCCC[C@@H]1Nc1ncc2c(=O)[nH]cc(-c3c[nH]c4cc(C(F)(F)F)ccc34)c2n1]

86.1 2-methylsulfanyl-8-[1-(toluene-4-sulfonyl)-6-trifluoromethyl-1H-indol-3-yl]-6H-pyrido[4,3-d]pyrimidin-5-one

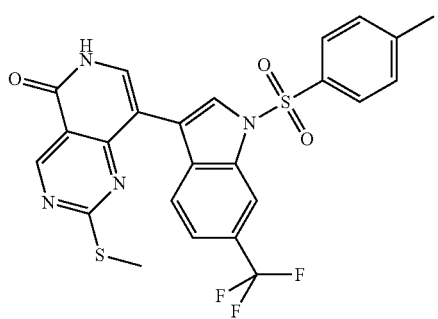 [SMILES: CSc1ncc2c(=O)[nH]cc(-c3cn(S(=O)(=O)c4ccc(C)cc4)c4cc(C(F)(F)F)ccc34)c2n1]

8-Iodo-2-methylsulfanyl-6H-pyrido[4,3-d]pyrimidin-5-one (1.303 g; 4.083 mmol; 95.00 mol %), 3-(4,4,5,5-tetramethyl-[1,3,2]dioxaborolan-2-yl)-1-(toluene-4-sulfonyl)-6-trifluoromethyl-1H-indole (2.000 g; 4.298 mmol; 100.00 mol %) and tripotassium phosphate hydrate (3.126 g; 12.895 mmol; 300.00 mol %) were suspended in 1,4-dioxane (80.000 ml) and water (20.000 ml). Under nitrogen [2-(2-aminophenyl)phenyl]-[dicyclohexyl-[2-(2,4,6-triisopropylphenyl)phenyl]phosphaniumyl]palladium chloride (0.169 g; 0.215 mmol; 5.00 mol %) was added and stirred at 100° C. for 2 h and was allowed to cool to rt for 14 h. The dioxane was removed in vacuo. The aqueous layer was diluted with water and extracted with DCM. The organic layer was dried over Na$_2$SO$_4$, filtered and evaporated to dryness to give 2 g (49%) of the title compound as a yellow solid; LC/MS (Method G): Rt 2.528 min; (M+H) 531.2.

86.2 2-((cis)-2-amino-cyclohexylamino)-8-[1-(toluene-4-sulfonyl)-6-trifluoromethyl-1H-indol-3-yl]-6H-pyrido[4,3-d]pyrimidin-5-one

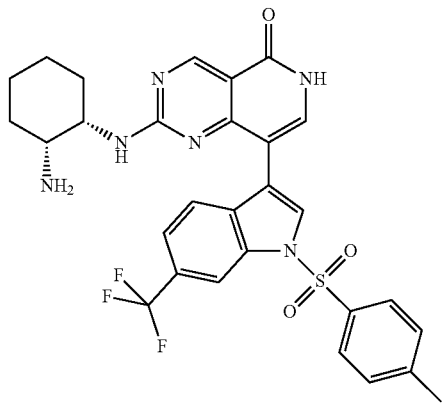 [SMILES: Cc1ccc(S(=O)(=O)n2cc(-c3c[nH]c(=O)c4cnc(N[C@H]5CCCC[C@H]5N)nc34)c3ccc(C(F)(F)F)cc32)cc1]

2-Methylsulfanyl-8-[1-(toluene-4-sulfonyl)-6-trifluoromethyl-1H-indol-3-yl]-6H-pyrido[4,3-d]pyrimidin-5-one (200.000 mg; 0.193 mmol; 100.00 mol %) and cis-1,2-cyclohexanediamine (0.234 ml; 1.930 mmol; 1000.00 mol %) was stirred at 100° C. for 14 h. The mixture was diluted with water and extracted with DCM. The organic layer was dried over Na$_2$SO$_4$, filtered and evaporated to residue. The residue was purified by flash chromatography and was purified a second time by flash chromatography (basic alumina) to give 28 mg (24%) of the title compound as a yellow solid; HPLC (Method J): (percent area) 100%; Rt 2.734 min.; LC/MS (Method G): Rt 2.165 min; (M+H) 597.2.

86.3 2-((cis)-2-amino-cyclohexylamino)-8-(6-trifluoromethyl-1H-indol-3-yl)-6H-pyrido[4,3-d]pyrimidin-5-one 2-((cis)-2-Amino-cyclohexylamino)-8-[1-(toluene-4-sulfonyl)-6-trifluoromethyl-1H-indol-3-yl]-6H-pyrido[4,3-d]pyrimidin-5-one (28.000 mg; 0.047 mmol; 100.00 mol %) was dissolved in tetrahydrofuran (3.000 ml) and ethanol (1.000 ml). Sodium hydroxide pellets (37.542 mg; 0.939 mmol; 2000.00 mol %) were added to the suspension. The solution was stirred at rt for 14 h and the solvent was evaporated. The residue was dissolved in DCM and water. The organic phase was extracted with water, the aqueous phase with DCM. The combined organic layers were dried over Na$_2$SO$_4$, filtered and evaporated to dryness. The residue was purified by preparative HPLC. The fractions containing the product were combined. NaHCO$_3$ was added until pH8 was reached. ACN was evaporated and the aqueous layer was extracted twice with DCM. The combined organic layers were dried over Na$_2$SO$_4$, filtered and evaporated to 7 mg (35%) of the title compound as a yellow solid;

HPLC (Method J): (percent area) 100%; Rt 2.303 min.; LC/MS (Method G): Rt 2.573 min; (M+H) 443.1.

Example 87

3-[2-((1R,2S)-2-amino-cyclohexylamino)-5-difluoromethyl-pyrido[4,3-d]-pyrimidin-8-yl]-1H-indole-6-carbonitrile ("A87")

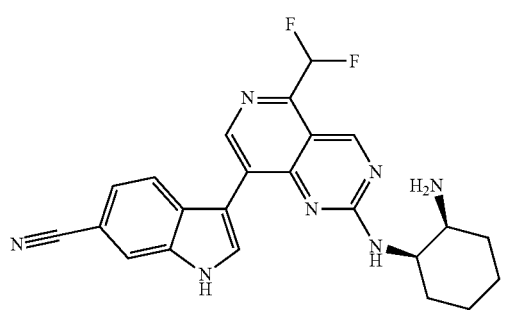 [SMILES: N#Cc1ccc2c(-c3cnc(C(F)F)c4cnc(N[C@@H]5CCCC[C@@H]5N)nc34)c[nH]c2c1]

87.1
5-methyl-2-methylsulfanyl-pyrido[4,3-d]pyrimidine

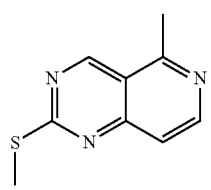

5-Chloro-2-methylsulfanyl-pyrido[4,3-d]pyrimidine (500.000 mg; 2.135 mmol; 100.00 mol %), trimethylboroxine, 50 wt % solution in THF (536.130 mg; 2.135 mmol; 100.00 mol %), 2-dicyclohexylphosphino-2',6'-dimethoxybiphenyl (90.375 mg; 0.214 mmol; 10.00 mol %) and cesiumfluoride (648.745 mg; 4.271 mmol; 200.00 mol %) were added together in a microwave vessel. 1,4-Dioxane (20,000 ml) was added. Under nitrogen palladium(II)-acetat (47.941 mg; 0.214 mmol; 10.00 mol %) was added. The vessel was closed with a septum and heated by microwave (150° C., 30 min). The reaction mixture was purified by flash chromatography to give 240 mg (56%) of the title compound as a yellow solid; HPLC (Method J): (percent area) 95.7%; Rt 1.395 min.; HPLC MS (Method G): (M+H) 192.1; Rt 0.94 min.

87.2 2-methylsulfanyl-pyrido[4,3-d]pyrimidine-5-carbaldehyde

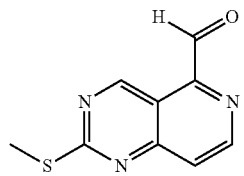

5-Methyl-2-methylsulfanyl-pyrido[4,3-d]pyrimidine (240.00 mg; 1.201 mmol; 1.000 eq.) was dissolved in 1,4-dioxane (4.00 ml; 46.762 mmol). Selenium dioxide (150.57 mg; 1.357 mmol; 1.130 eq.) was added and the reaction mixture was refluxed for 3.5 h. After cooling down to room temperature the reaction mixture was filtered and the mother liquor was evaporated under reduced pressure (brown solid). The residue was purified by flash chromatography to give 142 mg (58%) of the title compound as a beige solid; LC/MS (Method G): (percent area) 100%; Rt 1.121 min; (M+H) 206.1.

87.3 5-difluoromethyl-2-methylsulfanyl-pyrido[4,3-d]pyrimidine

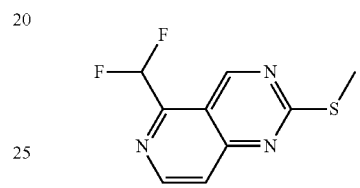

2-Methylsulfanyl-pyrido[4,3-d]pyrimidine-5-carbaldehyde (142.00 mg; 0.692 mmol; 1.000 eq.) was dissolved in dichlormethan (5.68 ml) and diethylamino sulfur trifluoride (304.71 µl; 2.076 mmol; 3.000 eq.) was added through a septum under nitrogen atmosphere. The solution was stirred at rt for 14 h. The reaction mixture was diluted with saturated $NaHCO_3$ solution (80 ml) and extracted with DCM three times. The combined organic layers were dried over $Na_2SO_4$, filtered and concentrated under reduced pressure. The residue was purified by flash chromatography to give 112 mg (71%) of the title compound as a beige solid; LC/MS (Method G): (percent area) 100%; Rt 1.8 min.; (M+H) 228.1.

87.4 5-difluoromethyl-8-iodo-2-methylsulfanyl-pyrido[4,3-d]pyrimidine

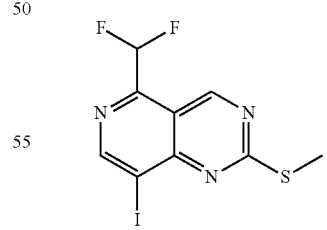

5-Difluoromethyl-2-methylsulfanyl-pyrido[4,3-d]pyrimidine (27.00 mg; 0.119 mmol; 0.194 eq.) was dissolved in N,N-dimethylformamide (3.00 ml; 0.039 mol). Trifluoroacetic acid (56.55 µl; 0.734 mmol; 1.200 eq.) and N-iodosuccinimide (192.67 mg; 0.856 mmol; 1.400 eq.) were added and the reaction mixture was stirred at 50° C. for 3 days. Trifluoroacetic acid (28.28 µl; 0,367 mmol; 0,600 eq.) and N-Iodosuccinimide for synthesis (96.33 mg; 0.428 mmol; 0.700 eq.) were added again and it was stirred for another 4 days. The reaction was treated with water and 0.1 N sodiumthiosulfate solution and stirred for about 20 minutes while cooling down to room temperature. The precipitate was filtered off and washed with water and DCM. This gives 197 mg (85%) of the title compound as a yellow solid; LC/MS (Method G): (percent area) 93.5%; Rt 2.291 min.; (M+H) 354.

87.5 2-chloro-5-difluoromethyl-8-iodo-pyrido[4,3-d]pyrimidine

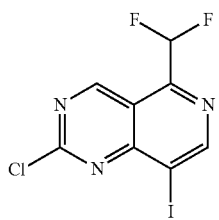 [SMILES: FC(F)c1ncc(I)c2nc(Cl)ncc12]

5-Difluoromethyl-8-iodo-2-methylsulfanyl-pyrido[4,3-d]pyrimidine (197.00 mg; 0.522 mmol; 1.000 eq.) was dissolved in acetonitrile (10.94 ml). After cooling to 0° C. dichloromethane (14.26 ml) and sulfuryl chloride (421.56 µl; 5.216 mmol; 10.000 eq.) were added and it was stirred for 3 h at this temperature. DCM was evaporated and the resulting solution was used in next reaction step without any purification. Yield: 178 mg (100%) of the title compound as a yellow solution; LC/MS (Method G): (percent area) 100%; Rt 2.037 min.; (M+H) 341.9.

87.6 [(1S,2R)-2-(5-difluoromethyl-8-iodo-pyrido[4,3-d]pyrimidin-2-ylamino)-cyclohexyl]-carbamic acid tert-butyl ester

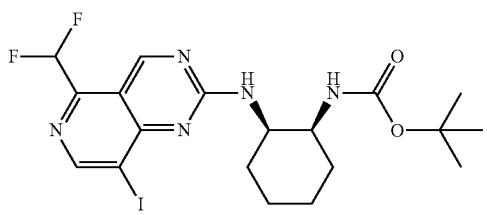 [SMILES: CC(C)(C)OC(=O)N[C@H]1CCCC[C@H]1Nc1ncc2c(C(F)F)ncc(I)c2n1]

To the solution of 2-chloro-5-difluoromethyl-8-iodo-pyrido[4,3-d]pyrimidine (178.12 mg; 0.522 mmol; 1.000 eq.) in acetonitrile (10 ml), N-ethyldiisopropyl-amine (975.74 µl; 5.738 mmol; 11.000 eq.) and ethanol (347.27 µl; 5.955 mmol) were added and ((1S,2R)-2-amino-cyclohexyl)-carbamic acid tert-butyl ester (117.37 mg; 0.548 mmol; 1.050 eq.) was added. The reaction mixture was heated by microwave at 120° C. for 5 min. The reaction mixture was evaporated under reduced pressure. The residue was washed with water and dried in vacuo to give 233 mg (77%) of the title compound as a brown solid; LC/MS (Method G): (percent area) 89.4%; Rt 2.503 min.; (M+H) 520.2.

87.7 {(1S,2R)-2-[8-(6-cyano-1H-indol-3-yl)-5-difluoromethyl-pyrido[4,3-d]pyrimidin-2-ylamino]-cyclohexyl}-carbamic acid tert-butyl ester

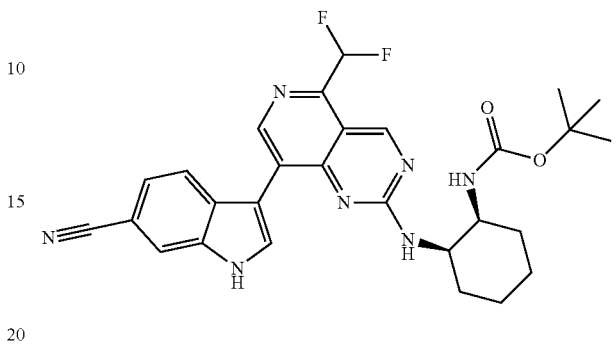

[(1S,2R)-2-(5-Difluoromethyl-8-iodo-pyrido[4,3-d]pyrimidin-2-ylamino)-cyclohexyl]-carbamic acid tert-butyl ester (96.00 mg; 0.185 mmol; 1.000 eq.), 1-BOC-6-cyanoindole-3-boronic acid pinacol ester (81.68 mg; 0.222 mmol; 1.200 eq.), palladium(II)-acetat (47% Pd) (2.08 mg; 0.009 mmol; 0.050 eq.), 2-dicyclohexylphosphino-2',6'-dimethoxybiphenyl (7.59 mg; 0.018 mmol; 0.100 eq.) and potassium carbonate (75.31 mg; 0.545 mmol; 2.948 eq.) were suspended in ethylenglycoldimethylether (1.91 ml; 18.485 mmol; 100.000 eq.) and water (0.67 ml; 36.971 mmol; 200.000 eq.) while purging nitrogen through the suspension. The suspension was heated by microwave for 45 min at 150° C. The reaction mixture was concentrated under reduced pressure. The residue was purified by flash chromatography to give 65 mg (66%) of the title compound as a yellow solid; LC/MS (Method G): (percent area) 100%; Rt 2.395 min; (M+H) 534.3.

87.8 3-[2-((1R,2S)-2-amino-cyclohexylamino)-5-difluoromethyl-pyrido-[4,3-d]pyrimidin-8-yl]-1H-indole-6-carbonitrile {(1S,2R)-2-[8-(6-Cyano-1H-indol-3-yl)-5-difluoromethyl-pyrido[4,3-d]pyrimidin-2-ylamino]-cyclohexyl}-carbamic acid tert-butyl ester (65.00 mg; 0.122 mmol; 1.000 eq.) was suspended in dichloromethane (0.95 ml; 14.876 mmol). Trifluoroacetic acid (93.85 µl; 1.218 mmol; 10.000 eq.) was added. The reaction mixture was stirred at rt for 14 h. The reaction mixture was treated with saturated NaHCO$_3$ solution and DCM and phases were separated. The aqueous layer was extracted with DCM 1 more time. The combined organic extracts were dried over Na$_2$SO$_4$ and evaporated under reduced pressure to give 46 mg (87%) of the title compound as a yellow solid; LC/MS (Method G): (percent area) 100%; Rt 1.971 min.; (M+H) 434.2;

$^1$H NMR (500 MHz, DMSO-d$_6$) δ [ppm] 12.19 (s, 1H), 9.52 (s, 1H), 8.90 (s, 1H), 8.39 (s, 1H), 8.04-7.93 (m, 2H), 7.87 (d, J=7.60 Hz, 1H), 7.55-7.29 (m, 2H), 3.88-3.78 (m, 1H), 3.15-2.99 (m, 1H), 1.93-1.10 (m, 8H).

Example 88

(1S,2R)—N-[5-methyl-8-(6-trifluoromethyl-1H-indol-3-yl)-pyrido[4,3-d]pyrimidin-2-yl]-cyclohexane-1,2-diamine ("A88")

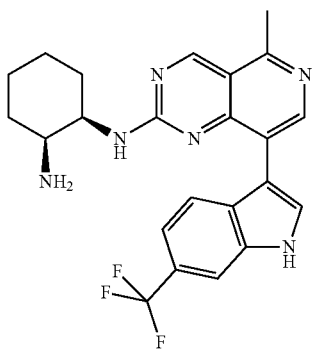 [SMILES: Cc1ncc(-c2c[nH]c3cc(C(F)(F)F)ccc23)c2nc(N[C@@H]3CCCC[C@@H]3N)ncc12]

88.1 5-chloro-2-methylsulfanyl-8-[1-(toluene-4-sulfonyl)-6-trifluoromethyl-1H-indol-3-yl]-pyrido[4,3-d]pyrimidine

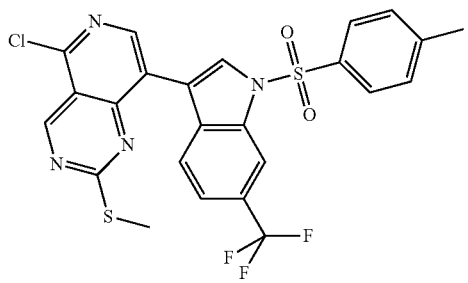 [SMILES: CSc1ncc2c(Cl)ncc(-c3cn(S(=O)(=O)c4ccc(C)cc4)c4cc(C(F)(F)F)ccc34)c2n1]

2-Methylsulfanyl-8-[1-(toluene-4-sulfonyl)-6-trifluoromethyl-1H-indol-3-yl]-6H-pyrido[4,3-d]pyrimidin-5-one (1.970 g; 1.901 mmol; 100.00 mol %) and phosphorylchloride (5.000 ml; 55.435 mmol; 2915.89 mol %) was added. The suspension was stirred at 110° C. for 4 h and then the solution was stirred at rt for 14 h. The solution was evaporated to dryness. Toluene was added and removed again by vacuo. The residue was suspended in a saturated NaHCO$_3$-solution/ice mixture. The aqueous phase was extracted twice with DCM. The organic layers were combined, dried over Na$_2$SO$_4$, filtered and evaporated to dryness. The residue was purified by flash chromatography to give 710 mg (43%) of the title compound as a yellow solid; HPLC (Method J): (percent area) 63.6%; Rt 3.871 min.; LC/MS (Method G): Rt 2.887 min.; (M+H) 549.1.

88.2 5-methyl-2-methylsulfanyl-8-[1-(toluene-4-sulfonyl)-6-trifluoromethyl-1H-indol-3-yl]-pyrido[4,3-d]pyrimidine

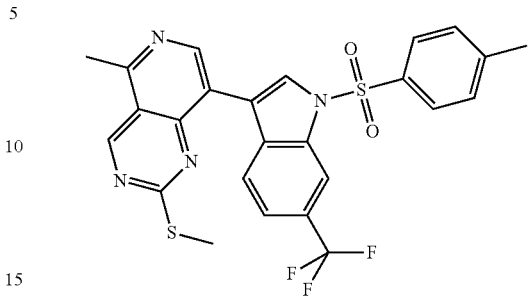

5-Chloro-2-methylsulfanyl-8-[1-(toluene-4-sulfonyl)-6-trifluoromethyl-1H-indol-3-yl]-pyrido[4,3-d]pyrimidine (710.000 mg; 0.823 mmol; 100.00 mol %), trimethylboroxine, 50 wt % solution in THF (206.512 mg; 0.823 mmol; 100.00 mol %), 2-dicyclohexylphosphino-2',6'-dimethoxybiphenyl (34.812 mg; 0.082 mmol; 10.00 mol %) and cesiumfluoride (249.891 mg; 1.645 mmol; 200.00 mol %) were given together. 1,4-Dioxane (20.000 ml) was added. Under nitrogen palladium(II)-acetat (18.466 mg; 0.082 mmol; 10.00 mol %) was added. The vessel was closed with a septum and heated by microwave (150° C., 45 min). The solvent was removed in vacuo and the precipitate purified by flash chromatography to give 384 mg (63%) of the title compound as a yellow solid; HPLC (Method J): (percent area) 70.9%; Rt 3.234 min.; LC/MS (Method G): Rt 2.506 min; (M+H) 529.

88.3 (cis)-N-{5-methyl-8-[1-(toluene-4-sulfonyl)-6-trifluoromethyl-1H-indol-3-yl]-pyrido[4,3-d]pyrimidin-2-yl}-cyclohexane-1,2-diamine

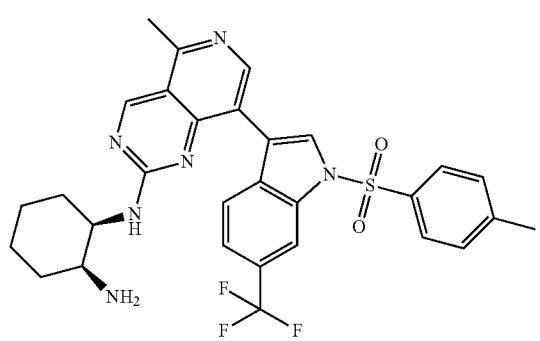 [SMILES: Cc1ccc(S(=O)(=O)n2cc(-c3cnc(C)c4cnc(N[C@@H]5CCCC[C@@H]5N)nc34)c3ccc(C(F)(F)F)cc32)cc1]

In a 10 ml-flask charged with 5-methyl-2-methylsulfanyl-8-[1-(toluene-4-sulfonyl)-6-trifluoromethyl-1H-indol-3-yl]-pyrido[4,3-d]pyrimidine (364.00 mg; 0.49 mmol; 1.00 eq.) cis-1,2-cyclohexanediamine (0.59 ml; 4.88 mmol; 10.00 eq.) was added and stirred at 100° C. for 3 h. The reaction was diluted with DCM. The organic layer was extracted with water and the aqueous layer was extracted with DCM. The combined organic layers were dried over Na$_2$SO$_4$ and filtered and the solvent removed in vacuo. The precipitate purified by flash chromatography to give 145 mg (50%) of the title compound as a yellow liquid; HPLC: (purity) 100%; Rt 2.551 min.; LC/MS: Rt 1.792 min; (M+H) 595.2.

88.4 ((cis)-2-{5-methyl-8-[1-(toluene-4-sulfonyl)-6-trifluoromethyl-1H-indol-3-yl]-pyrido[4,3-d]pyrimidin-2-ylamino}-cyclohexyl)-carbamic acid tert-butyl ester

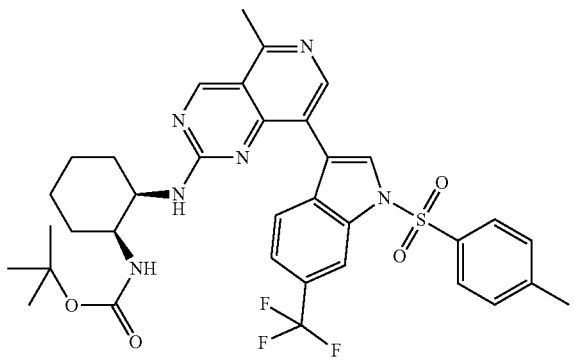 [SMILES: Cc1ccc(S(=O)(=O)n2cc(-c3cnc(C)c4cnc(N[C@@H]5CCCC[C@@H]5NC(=O)OC(C)(C)C)nc34)c3ccc(C(F)(F)F)cc32)cc1]

(1R,2S)—N-{5-Methyl-8-[1-(toluene-4-sulfonyl)-6-trifluoromethyl-1H-indol-3-yl]-pyrido[4,3-d]pyrimidin-2-yl}-cyclohexane-1,2-diamine (145.00 mg; 0.24 mmol; 1.00 eq.), DMAP (0.06 g; 0.49 mmol; 2.00 eq.) and di-tert-butyldicarbonat (0.11 g; 0.51 mmol; 2.10 eq.) was dissolved in tetrahydrofuran (25.00 ml). The reaction mixture was stirred by rt over 3 days. The crude product was evaporated under vacuo an extracted with water/DCM. Then the crude product was dried over Na$_2$SO$_4$ and filtered and the solvent removed in vacuo. The residue was purified twice by flash chromatography to give 44 mg (26%) of the title compound as a yellow solid; LC/MS (Chromolith Speed Rod RP18e, 50-4.6 mm; ACN+0.1% TFA, water+0.1% TFA): (percent area) 100%; Rt 2.597 min.; (M+H) 695.3.

88.5 Enantiomer 1: (1S,2R)—N-{5-methyl-8-[1-(toluene-4-sulfonyl)-6-trifluoromethyl-1H-indol-3-yl]-pyrido[4,3-d]pyrimidin-2-yl}-cyclohexane-1,2-diamine and enantiomer 2: (1R,2S)—N-{5-methyl-8-[1-(toluene-4-sulfonyl)-6-trifluoromethyl-1H-indol-3-yl]-pyrido[4,3-d]pyrimidin-2-yl}-cyclohexane-1,2-diamine

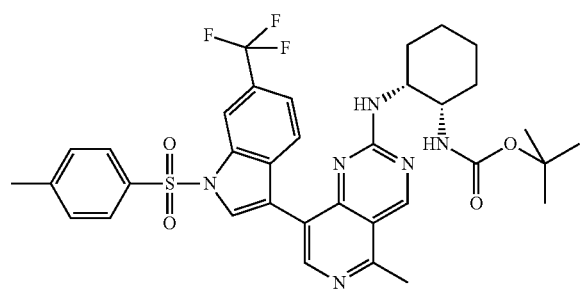 [SMILES: Cc1ccc(S(=O)(=O)n2cc(-c3cnc(C)c4cnc(N[C@@H]5CCCC[C@@H]5NC(=O)OC(C)(C)C)nc34)c3ccc(C(F)(F)F)cc32)cc1]

((cis)-2-{5-Methyl-8-[1-(toluene-4-sulfonyl)-6-trifluoromethyl-1H-indol-3-yl]-pyrido[4,3-d]pyrimidin-2-ylamino}-cyclohexyl)-carbamic acid tert-butyl ester (44.000 mg; 0.063 mmol; 100.00 mol %) was separated in both enantiomers with a chiral column.

88.5.1 Enantiomer 1 elutes first from chiral column and gives 15 mg; HPLC (Chiralpk AD-H; 25% IP0.5% DEA): (percent area) 100%; Rt 3.23 min. Absolute configuration arbitrary: ((1S,2R)-2-{5-methyl-8-[1-(toluene-4-sulfonyl)-6-trifluoromethyl-1H-indol-3-yl]-pyrido[4,3-d]pyrimidin-2-ylamino}-cyclohexyl)-carbamic acid tert-butyl ester.

88.5.2 Enantiomer 2: Gives 18 mg (41%) of the title compound; HPLC (Chiralpk AD-H; 25% IP0.5% DEA): (percent area) 100%; Rt 8.57 min. Absolute configuration arbitrary: ((1R,2S)-2-{5-methyl-8-[1-(toluene-4-sulfonyl)-6-trifluoromethyl-1H-indol-3-yl]-pyrido[4,3-d]pyrimidin-2-ylamino}-cyclohexyl)-carbamic acid tert-butyl ester.

88.6 (1S,2R)—N-{5-methyl-8-[1-(toluene-4-sulfonyl)-6-trifluoromethyl-1H-indol-3-yl]-pyrido[4,3-d]pyrimidin-2-yl}-cyclohexane-1,2-diamine trifluoroacetate

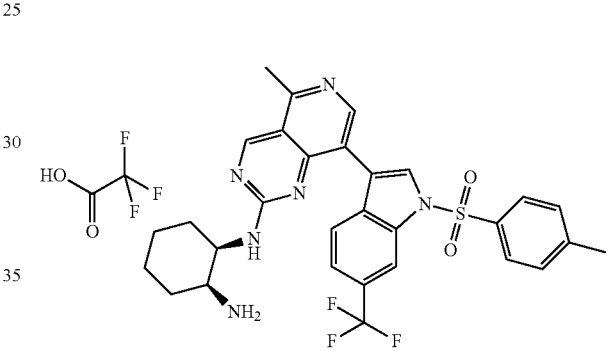

Enantiomer 1 from example 88.5.1 (15.000 mg; 0.022 mmol; 100.00 mol %) was dissolved in dichloromethane (1.000 ml) and trifluoroacetic acid (0.016 ml; 0.216 mmol; 1000.00 mol %). The solution was stirred at rt for 5.5 h and the solvent removed in vacuo to give 33 mg (216%) of the title compound as a yellow oil; HPLC (Method J): (percent area) 100%; Rt 2.536 min.; LC/MS (Method G): Rt 2.256 min; (M+H) 595.3.

88.7 (1S,2R)—N-[5-methyl-8-(6-trifluoromethyl-1H-indol-3-yl)-pyrido[4,3-d]pyrimidin-2-yl]-cyclohexane-1,2-diamine (1S,2R)—N-{5-Methyl-8-[1-(toluene-4-sulfonyl)-6-trifluoromethyl-1H-indol-3-yl]-pyrido[4,3-d]pyrimidin-2-yl}-cyclohexane-1,2-diamine trifluoroacetate from example 88.6 (33.000 mg; 0.047 mmol; 100.00 mol %) was dissolved in tetrahydrofuran (3.000 ml) and ethanol (1.000 ml). Then sodium hydroxide pellets (0.017 ml; 0.931 mmol; 2000.00 mol %) were added. The solution was stirred for 4 h and the solvent removed in vacuo. The residue was dissolved in DCM and water. The organic layer was washed with water, the aqueous layer was washed with DCM. The combined organic layers were dried over Na$_2$SO$_4$, filtered and evaporated to dryness to give 5 mg of the title compound as a yellow solid; LC/MS (Method H): Rt 1.473 min; (M+H) 441.2.

Example 89

(1R,2S)—N-[5-methyl-8-(6-trifluoromethyl-1H-indol-3-yl)-pyrido[4,3-d]pyrimidin-2-yl]-cyclohexane-1,2-diamine ("A89")

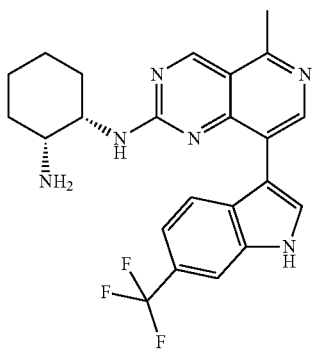 [SMILES: Cc1ncc(-c2c[nH]c3cc(C(F)(F)F)ccc23)c2nc(N[C@H]3CCCC[C@H]3N)ncc12]

89.1 (1R,2S)—N-{5-methyl-8-[1-(toluene-4-sulfonyl)-6-trifluoromethyl-1H-indol-3-yl]-pyrido[4,3-d]pyrimidin-2-yl}-cyclohexane-1,2-diamine trifluoroacetate

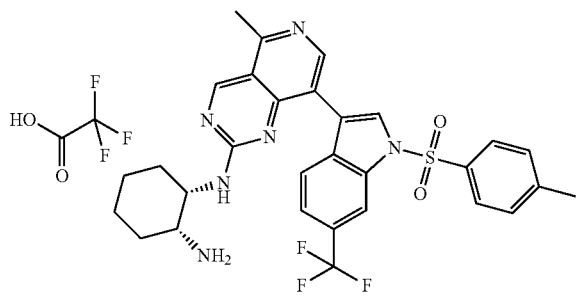

Enantiomer 2 from example 88.5.2 (18.000 mg; 0.026 mmol; 100.00 mol %) was dissolved in dichloromethane (1.000 ml) and trifluoroacetic acid (0.020 ml; 0.259 mmol; 1000.00 mol %). The solution was stirred at rt for 5.5 h and the solvent removed in vacuo to give 25 mg (131%) of the title compound; HPLC (Method J): (percent area) 96.4%; Rt 2.529 min.; LC/MS (Method G): Rt 2.246 min; (M+H) 595.3.

89.2 (1R,2S)—N-[5-methyl-8-(6-trifluoromethyl-1H-indol-3-yl)-pyrido[4,3-d]pyrimidin-2-yl]-cyclohexane-1,2-diamine (1R,2S)—N-{5-methyl-8-[1-(toluene-4-sulfonyl)-6-trifluoromethyl-1H-indol-3-yl]-pyrido[4,3-d]pyrimidin-2-yl}-cyclohexane-1,2-diamine trifluoroacetate (25.000 mg; 0.034 mmol; 100.00 mol %) was dissolved in tetrahydrofuran (3.000 ml) and ethanol (1.000 ml). Then sodium hydroxide pellets (0.013 ml; 0.680 mmol; 2000.00 mol %) were added. The solution was stirred at rt for 4 h and the solvent removed in vacuo. The residue was dissolved in DCM and water. The organic layer was washed with water, the aqueous layer was washed with DCM. The combined organic layers were dried over $Na_2SO_4$, filtered and evaporated to dryness to give 4 mg (27%) of the title compound; HPLC (Method J): (percent area) 17.5/82.5%; Rt 2.095/2.129 min; (double peak/double peak); LC/MS (Method G): Rt 1.39 min; (M+H) 441.2.

Example 90

2-((1S,2R)-2-amino-cyclohexylamino)-8-(1-methyl-1H-pyrazol-4-yl)-6H-pyrido[4,3-d]pyrimidin-5-one ("A90")

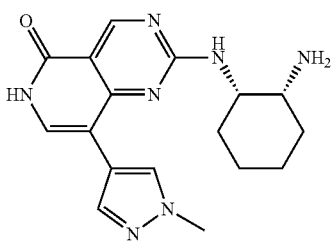 [SMILES: Cn1cc(-c2c[nH]c(=O)c3cnc(N[C@H]4CCCC[C@H]4N)nc23)cn1]

90.1 8-(1-methyl-1H-pyrazol-4-yl)-2-methylsulfanyl-6H-pyrido[4,3-d]pyrimidin-5-one

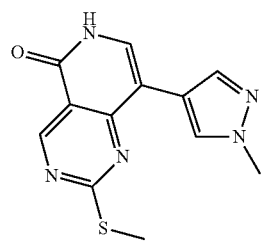 [SMILES: CSc1ncc2c(=O)[nH]cc(-c3cnn(C)c3)c2n1]

8-Iodo-2-methylsulfanyl-6H-pyrido[4,3-d]pyrimidin-5-one (2.00 g; 6.27 mmol; 1.00 eq.), 1-methylpyrazole-4-boronic acid pinacolester (1.56 g; 7.52 mmol; 1.20 eq.), tripotassium phosphate trihydrate (3.99 g; 18.80 mmol; 3.00 eq.), Xphos Pd—Cl precat (246.55 mg; 0.31 mmol; 0.05 eq.), 1,4-dioxane (80.00 ml; 935.25 mmol; 149.23 eq.) and water (20.00 ml; 1109.88 mmol; 177.09 eq.) were combined and heated to 120° C. for 4 h. 1-Methylpyrazole-4-boronic acid pinacolester (1.56 g; 7.52 mmol; 1.20 eq.) was added and heated for 14 h. 1-Methylpyrazole-4-boronic acid pinacolester (1.56 g; 7.52 mmol; 1.20 eq.) and Xphos Pd—Cl precat (246.55 mg; 0.31 mmol; 0.05 eq.) were added and heated 1.5 h. 1-Methylpyrazole-4-boronic acid pinacolester (1.56 g; 7.52 mmol; 1.20 eq.) and Xphos Pd—Cl precat (246.55 mg; 0.31 mmol; 0.05 eq.) were added and heated 1.5 h. Ethyl acetate and water were added and filtered. The solvent was removed in vacuo to give crude 1947 mg (114%) of the title compound as a brown solid; HPLC MS (Method G): Rt 1.61 min; (M+H) 274.1.

90.2 2-((1R,2S)-2-amino-cyclohexylamino)-8-(1-methyl-1H-pyrazol-4-yl)-6H-pyrido[4,3-d]pyrimidin-5-one

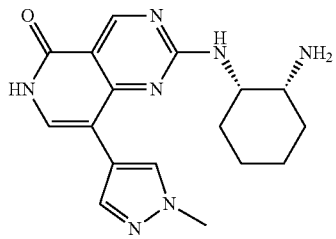

8-(1-Methyl-1H-pyrazol-4-yl)-2-methylsulfanyl-6H-pyrido[4,3-d]pyrimidin-5-one (crude example 90.1; 100.00 mg; 0.37 mmol; 1.00 eq.) and cis-1,2-diamino-cyclohexane (222.02 μl; 1.83 mmol; 5.00 eq.) were heated to 150° C. for 24 h. After cooling down, water was added to the mixture and filtered. The residue gives 60 mg (45%) of the title compound as a brown solid; HPLC MS (Method G): (percent area) 94.11%; Rt 1.62 min; (M+H) 340.2.

90.3 {(1R,2S)-2-[8-(1-methyl-1H-pyrazol-4-yl)-5-oxo-5,6-dihydro-pyrido-[4,3-d]pyrimidin-2-ylamino]-cyclohexyl}-carbamic acid tert-butyl ester

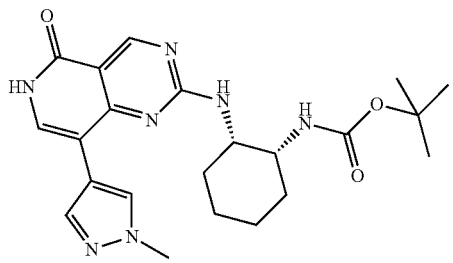 [SMILES: Cn1cc(-c2c[nH]c(=O)c3cnc(N[C@H]4CCCC[C@H]4NC(=O)OC(C)(C)C)nc23)cn1]

2-((1R,2S)-2-Amino-cyclohexylamino)-8-(1-methyl-1H-pyrazol-4-yl)-6H-pyrido[4,3-d]pyrimidin-5-one (example 90.2; 59.70 mg; 0.17 mmol; 1.00 eq.) was dissolved in tetrahydrofuran (900.00 μl; 11.11 mmol; 67.10 eq.), triethylamine (34.42 μl; 0.25 mmol; 1.50 eq.) and di-tert-butyl dicarbonate (38.96 μl; 0.18 mmol; 1.10 eq.) in tetrahydrofuran (150.00 μl; 1.85 mmol; 11.18 eq.) was added. The mixture was stirred for 14 h. Di-tert-butyl dicarbonate (0.04 ml; 0.18 mmol; 1.10 eq.) and triethylamine (0.03 ml; 0.25 mmol; 1.50 eq.) were added and the reaction stirred for 14 h. Di-tert-butyl dicarbonate (0.04 ml; 0.18 mmol; 1.10 eq.) and triethylamine (0.03 ml; 0.25 mmol; 1.50 eq.) were added. Di-tert-butyl dicarbonate (0.04 ml; 0.18 mmol; 1.10 eq.) and 4-(dimethylamino)pyridine (DMAP) (5.00 mg; 0.04 mmol; 0.25 eq.) were added. The mixture was washed two times with water and one time with brine and then dried over magnesium sulfate. The solvent was removed in vacuo to give 83 mg (114%) of the title compound as a brown solid.

90.4 2-((1S,2R)-2-amino-cyclohexylamino)-8-(1-methyl-1H-pyrazol-4-yl)-6H-pyrido[4,3-d]pyrimidin-5-one {(1R,2S)-2-[8-(1-Methyl-1H-pyrazol-4-yl)-5-oxo-5,6-dihydro-pyrido-[4,3-d]pyrimidin-2-ylamino)-cyclohexyl}-carbamic acid tert-butyl ester (example 90.3; 83.10 mg; 0.19 mmol; 1.00 eq.), ethylacetat (10.00 ml; 102.15 mmol; 540.24 eq.) and hydrochloric acid (1 N) (1.89 ml; 1.89 mmol; 10.00 eq.) were given into an vial and heated for 2 h at 50° C. Hydrochloric acid (1 N) (1928.55 mg; 1.89 mmol; 10.00 eq.) and 2 mL ethyl acetate was added and stirred for 14 h. Ethyl acetate and water were added and the organic layer was washed three times with water, then the combined water layer were brought to alkaline pH and extracted with ethyl acetate. The combined organic layers were evaporated to dryness and the residue purified by reverse phase HPLC to give 5 mg of the title compound as a colorless solid; HPLC (Method J): (percent area) 100%; Rt 2.31 min.; LC/MS (Method H): Rt 49 min.; (M+H) 340.1.

Example 91

(1R,2S)—N-[5-difluoromethyl-8-(1-methyl-1H-pyrazol-4-yl)-pyrido-[4,3-d]pyrimidin-2-yl]-cyclohexane-1,2-diamine ("A91")

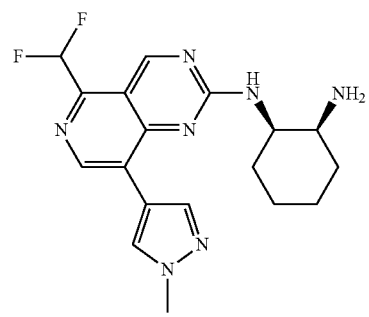 [SMILES: Cn1cc(-c2cnc(C(F)F)c3cnc(N[C@@H]4CCCC[C@@H]4N)nc23)cn1]

91.1 {(1S,2R)-2-[5-difluoromethyl-8-(1-methyl-1H-pyrazol-4-yl)-pyrido-[4,3-d]pyrimidin-2-ylamino]-cyclohexyl}-carbamic acid tert-butyl ester

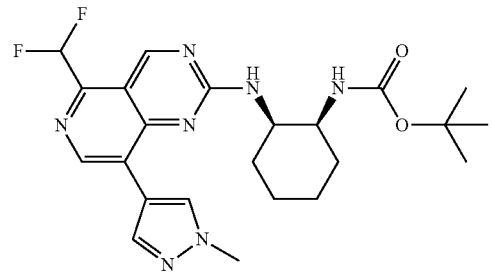 [SMILES: Cn1cc(-c2cnc(C(F)F)c3cnc(N[C@@H]4CCCC[C@@H]4NC(=O)OC(C)(C)C)nc23)cn1]

[(1S,2R)-2-(5-Difluoromethyl-8-iodo-pyrido[4,3-d]pyrimidin-2-ylamino)-cyclohexyl]-carbamic acid tert-butyl ester (66.00 mg; 0.086 mmol; 1.000 eq.), 1-methylpyrazole-4-boronic acid pinacolester (21.42 mg; 0.103 mmol; 1.200 eq.), palladium(II)-acetat (47% Pd) (0.96 mg; 0.004 mmol; 0.050 eq.), 2-dicyclohexylphosphino-2',6'-dimethoxybiphenyl (3.52 mg; 0.009 mmol; 0.100 eq.) and potassium carbonate (34.95 mg; 0.253 mmol; 2.948 eq.) were added and suspended in ethylenglycoldimethylether (0.89 ml; 8.578 mmol; 100.000 eq.) and water (0.31 ml; 17.157 mmol; 200.000 eq.) while purging nitrogen through the suspension. The suspension was heated in the microwave for 45 min at 150° C. The solvent was removed in vacuo and the residue was purified by flash chromatography to give 33 mg (81%) of the title compound; LC/MS (Method G): 100%; Rt 2.299 min.; (M+H) 474.3.

91.2 (1R,2S)—N-[5-difluoromethyl-8-(1-methyl-1H-pyrazol-4-yl)-pyrido[4,3-d]pyrimidin-2-yl]-cyclohexane-1,2-diamine {(1S,2R)-2-[5-Difluoromethyl-8-(1-methyl-1H-pyrazol-4-yl)-pyrido[4,3-d]pyrimidin-2-ylamino]-cyclohexyl}-carbamic acid tert-butyl ester (33.00 mg; 0.070 mmol; 1.000 eq.) was dissolved in ethylacetat (1.57 ml). Hydrochloric acid (1 N) (348.45 µl; 0.348 mmol; 5.000 eq.) was added and stirred at rt for 14 h and 3 days at 50° C. The solvent was removed in vacuo to give 28 mg (99%) of the title compound as an orange solid; LC/MS (Method G): (percent area) 100%; Rt 1.573 min.; (M+H) 374.2;

$^1$H NMR (500 MHz, DMSO+CF$_3$SO$_3$D) δ [ppm] 3.81-3.72 (m, 1H), 2.02-1.92 (m, 2H), 1.92-1.86 (s, 3H), 1.83-1.59 (m, 4H), 1.57-1.34 (m, 2H), 4.46-4.38 (m, 1H), 9.76-9.44 (s, 1H), 9.06-8.80 (s, 1H), 8.59-8.48 (s, 1H), 8.39-8.21 (s, 1H), 7.56-6.98 (t, J=53.5 Hz, 1H).

Pharmacological Data

TABLE 1

Syk inhibition of some representative compounds of the formula I

| Compound No. | IC$_{50}$ SYK (enzyme assay) |
|---|---|
| "A1" | A |
| "A2" | B |
| "A3" | B |
| "A4" | C |
| "A5" | C |
| "A6" | C |
| "A7" | C |
| "A8" | B |
| "A9" | C |
| "A10" | A |
| "A11" | C |
| "A12" | |
| "A13" | |
| "A14" | B |
| "A15" | |
| "A16" | |
| "A17" | B |
| "A18" | A |
| "A19" | A |
| "A20" | B |
| "A21" | C |
| "A22" | A |
| "A23" | B |
| "A24" | A |
| "A25" | C |
| "A26" | C |
| "A27" | A |
| "A28" | |
| "A29" | C |
| "A30" | C |
| A31" | B |
| A32" | C |
| A33" | C |
| "A34" | |
| "A35" | B |
| "A36" | C |
| "A37" | C |
| "A38" | |
| "A39" | |
| "A40" | A |
| "A41" | A |
| "A42" | C |
| "A43" | C |
| "A44" | B |
| "A45" | A |
| "A46" | A |
| "A47" | |
| "A48" | |
| "A49" | A |
| "A50" | |
| "A61" | C |
| "A62" | A |
| "A63" | A |
| "A65" | A |
| "A66" | C |
| "A67" | C |
| "A68" | A |
| "A69" | B |
| "A72" | A |
| "A76" | A |
| "A77" | A |
| "A79" | C |
| "A80" | C |
| "A81" | B |
| "A82" | A |
| "A85" | B |
| "A87" | A |
| "A88" | C |
| "A89" | A |
| "A91" | B |

IC$_{50}$: <0.1 µM = A;
0.1-1 µM = B;
1-50 µM = C

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. Compounds of the formula I

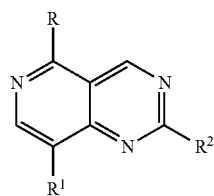

I in which
R denotes H, A or $NR^4R^{4'}$,
$R^1$ denotes $Ar^1$, $Het^1$, CN, A or —C≡C—$Ar^1$,
$R^2$ denotes $Het^2$, $NR^3Cyc$, $NR^3CHR^3CON(R^3)_2$, $NR^3[C(R^3)_2]_pCR^3(NH_2)CH_2OA$ or $NR^3[C(R^3)_2]_pN(R^3)_2$,
$Ar^1$ denotes phenyl, which is mono-, di- or trisubstituted by A, $(CH_2)_nHet^3$, $[C(R^3)_2]_nOR^3$, $[C(R^3)_2]_nN(R^3)_2$, $NO_2$, CN, Hal, $COOR^3$, $CON(R^3)_2$, $NR^3COA$, $NR^3SO_2A$, $SO_2N(R^3)_2$ and/or $S(O)_mA$,
$Het^1$ denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]oxazinyl, 4H-benzo[1,4]oxazinyl, benzimidazolyl, pyridyl, pyrimidinyl, imidazolyl, pyrazolyl, furyl,thiazolyl, triazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, $SO_2NH_2$, $(CH_2)_nNH_2$, $(CH_2)_nNHA$, $(CH_2)_nNA_2$ and/or =O,
$Het^2$ denotes piperidinyl, piperazinyl, pyrrolidinyl, morpholinyl, tetrahydropyranyl, pyrazolyl, indazolyl, azetidinyl or octahydro-benzimidazolyl, each of which is mono-, di- or trisubstituted by Hal, A, $(CH_2)_nNH_2$, $(CH_2)_nNHA$, $(CH_2)_nNA_2$, $(CH_2)_nOH$ and/or $(CH_2)_nOA$,
$Het^3$ denotes piperidinyl, piperazinyl, pyrrolidinyl, morpholinyl, imidazolidinyl, pyridyl, pyrimidinyl, imidazolyl, pyrazolyl, furyl, thiazolyl or triazolyl, each of which is unsubstituted or mono- or disubstituted by A and/or =O,
$R^3$ denotes H or alkyl having 1, 2, 3 or 4 C-atoms,
$R^4$ and $R^{4'}$ each, independently of one another, denote H or A,
A denotes unbranched or branched alkyl having 1-10 C atoms, in which 1-7 H atoms may be replaced by F and/or in which one or two non-adjacent $CH_2$ groups may be replaced by O and/or NH,
or
cyclic alkyl having 3-7 C atoms,
Cyc denotes cyclic alkyl having 3-7 C atoms, which may be unsubstituted or monosubstituted by $NH_2$, CN, $CONH_2$ or OH,
m denotes 0, 1 or 2,
n denotes 0, 1, 2, 3 or 4,
p denotes 1, 2, 3 or 4,
and pharmaceutically acceptable solvates, salts, enantiomers, tautomers and stereoisomers thereof.
2. Compounds according to claim 1 in which
$Ar^1$ denotes phenyl, which is mono-, di- or trisubstituted by A, $(CH_2)_nHet^3$ and/or $SO_2NH_2$,
and pharmaceutically acceptable solvates, salts, enantiomers, tautomers and stereoisomers thereof.
3. Compounds according to claim 1 in which
$Het^1$ denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]oxazinyl, 4H-benzo[1,4]oxazinyl, benzimidazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, and/or =O,
and pharmaceutically acceptable solvates, salts, enantiomers, tautomers and stereoisomers thereof.
4. Compounds according to claim 1 in which
$Het^2$ denotes piperidinyl or octahydro-benzimidazolyl, each of which is monosubstituted by A, $(CH_2)_nOH$ or $(CH_2)_nOA$,
and pharmaceutically acceptable solvates, salts, enantiomers, tautomers and stereoisomers thereof.
5. Compounds according to claim 1 in which
R denotes H, A or $NR^4R^{4'}$,
$R^1$ denotes $Ar^1$, $Het^1$, CN, A or —C≡C—$Ar^1$,
$R^2$ denotes $Het^2$, $NR^3Cyc$, $NR^3CHR^3CON(R^3)_2$, $NR^3[C(R^3)_2]_pCR^3(NH_2)CH_2OA$ or $NR^3[C(R^3)_2]_pN(R^3)_2$,
$Ar^1$ denotes phenyl, which is mono-, di- or trisubstituted by A, $(CH_2)_nHet^3$ and/or $SO_2NH_2$, Het¹ denotes 3,6-dihydro-2H-pyranyl, tetrahydropyridinyl, 1,3-dihydro-benzimidazolyl, pyrazolyl, chromanyl, 1,2,3,4-tetrahydro-pyrazolo[1,5-a]pyridinyl, 6,7-dihydro-4H-pyrazolo[5,1-c][1,4]-oxazinyl, 1,4-dihydro-benzo[d][1,3]oxazinyl, 4H-benzo[1,4] oxazinyl, benzimidazolyl, benzotriazolyl, indolyl, indazolyl, 1,3- or 2,3-dihydro-indolyl, each of which is unsubstituted or mono-, di-, tri- or tetrasubstituted by A, CN, OH, OA, Hal, and/or =O, Het² denotes piperidinyl or octahydro-benzimidazolyl, each of which is monosubstituted by A, (CH₂)ₙOH or (CH₂)ₙOA, Het³ denotes triazolyl, R³ denotes H or alkyl having 1, 2, 3 or 4 C-atoms, R⁴, R⁴' each, independently of one another, denote H or A, A denotes unbranched or branched alkyl having 1-10 C atoms, in which 1-7 H atoms may be replaced by F and/or in which one or two non-adjacent CH₂ groups may be replaced by O and/or NH, or cyclic alkyl having 3-7 C atoms, Cyc denotes cyclic alkyl having 3-7 C atoms, which may be unsubstituted or monosubstituted by NH₂, CN, CONH₂ or OH, m denotes 0, 1 or 2, n denotes 0, 1, 2, 3 or 4, p denotes 1, 2, 3 or 4, and pharmaceutically acceptable solvates, salts, enantiomers, tautomers and stereoisomers thereof.

6. Compounds according to claim 1, selected from the following compounds:

| Nr. | name |
|---|---|
| "A1" | N2-((cis)-2-Amino-cyclohexyl)-8-(1-methyl-1H-pyrazol-4-yl)-pyrido[4,3-d]pyrimidine-2,5-diamine |
| "A2" | (1R,2S)-N-[8-(1-Methyl-1H-pyrazol-4-yl)-pyrido[4,3-d]pyrimidin-2-yl]-cyclohexane-1,2-diamine hydrochloride |
| "A3" | N2-(cis-2-Amino-cyclohexyl)-8-(3-[1,2,3]triazol-2-yl-phenyl)-pyrido[4,3-d]pyrimidine-2,5-diamine |
| "A4" | N2-((cis)-2-Amino-cyclohexyl)-8-(1-methyl-1H-pyrazol-4-yl)-pyrido[4,3-d]pyrimidine-2,5-diamine |
| "A5" | {1-[5-Amino-8-(1-methyl-1H-pyrazol-4-yl)-pyrido[4,3-d]pyrimidin-2-yl]-piperidin-4-yl}-methanol |
| "A6" | N2-(2-Amino-ethyl)-8-(1-methyl-1H-pyrazol-4-yl)-pyrido[4,3-d]-pyrimidine-2,5-diamine |
| "A7" | N2-(cis-2-Amino-cyclohexyl)-8-(4-tert-butyl-phenyl)-pyrido[4,3-d]pyrimidine-2,5-diamine |
| "A8" | N2-(cis-2-Amino-cyclohexyl)-8-(1-isobutyl-1H-pyrazol-4-yl)-pyrido[4,3-d]pyrimidine-2,5-diamine |
| "A9" | 5-Amino-2-(cis-2-amino-cyclohexylamino)-pyrido[4,3-d]-pyrimidine-8-carbonitrile |
| "A10" | N2-(cis-2-Amino-cyclohexyl)-8-(1H-indol-2-yl)-pyrido-[4,3-d]pyrimidine-2,5-diamine |
| "A11" | 2-((cis)-3-Methyl-octahydro-benzoimidazol-1-yl)-8-(1-methyl-1H-pyrazol-4-yl)-pyrido[4,3-d]pyrimidin-5-ylamine |
| "A12" | N2-(cis-2-Amino-cyclohexyl)-8-methyl-pyrido-[4,3-d]pyrimidine-2,5-diamine |
| "A13" | N2-((cis)-2-Amino-cyclohexyl)-8-(4-trifluoromethoxy-phenyl)-pyrido[4,3-d]pyrimidine-2,5-diamine |
| "A14" | N2-((cis)-2-Amino-cyclohexyl)-8-(4-trifluoromethoxy-phenyl)-pyrido[4,3-d]pyrimidine-2,5-diamine |
| "A15" | {1-[5-Cyclopropylamino-8-(1-methyl-1H-pyrazol-4-yl)-pyrido[4,3-d]pyrimidin-2-yl]-piperidin-4-yl}-methanol |
| "A16" | {1-[5-Diethylamino-8-(1-methyl-1H-pyrazol-4-yl)-pyrido[4,3-d]-pyrimidin-2-yl]-piperidin-4-yl}-methanol |
| "A17" | N2-((1R,2S)-2-Amino-cyclohexyl)-8-phenyl-pyrido[4,3-d]-pyrimidine-2,5-diamine |
| "A18" | N2-(cis-2-Amino-cyclohexyl)-8-(7-methoxy-1H-indol-2-yl)-pyrido[4,3-d]pyrimidine-2,5-diamine |
| "A19" | N2-(cis-2-Amino-cyclohexyl)-8-(5-methoxy-1H-indol-2-yl)-pyrido[4,3-d]pyrimidine-2,5-diamine |
| "A20" | N2-((R)-2-Amino-3-methoxy-propyl)-8-(1-methyl-1H-pyrazol-4-yl)-pyrido[4,3-d]pyrimidine-2,5-diamine |
| "A21" | N2-((cis)-2-Amino-cyclohexyl)-8-m-tolyl-pyrido[4,3-d]pyrimidine-2,5-diamine |
| "A22" | N2-((cis)-2-Amino-cyclohexyl)-8-m-tolyl-pyrido[4,3-d]pyrimidine-2,5-diamine |
| "A23" | 2-[5-Amino-2-((cis)-2-amino-cyclohexylamino)-pyrido[4,3-d]-pyrimidin-8-yl]-1H-indole-5-carbonitrile |
| "A24" | N2-(cis-2-Amino-cyclohexyl)-8-(1H-indol-3-yl)-pyrido[4,3-d]-pyrimidine-2,5-diamine |
| "A25" | cis-N-[8-(1,3-Dimethyl-1H-pyrazol-4-yl)-pyrido[4,3-d]pyrimidin-2-yl]-cyclohexane-1,2-diamine |
| "A26" | (1S,2R)-N-[8-(1-Isopropyl-1H-pyrazol-4-yl)-pyrido[4,3-d]pyrimidin-2-yl]-cyclohexane-1,2-diamine |
| "A27" | (1S,2R)-N-[8-(1H-Indol-3-yl)-pyrido[4,3-d]pyrimidin-2-yl]-cyclohexane-1,2-diamine |
| "A28" | 3-[2-((1R,2S)-2-Amino-cyclohexylamino)-pyrido[4,3-d]pyrimidin-8-yl]-benzene sulfonamide |
| "A29" | (1S,2R)-N-[8-(4,4-Dimethyl-chroman-7-yl)-pyrido[4,3-d]pyrimidin-2-yl]-cyclohexane-1,2-diamine |
| "A30" | (R)-3-Methoxy-N1-(8-m-tolyl-pyrido[4,3-d]pyrimidin-2-yl)-propane-1,2-diamine |
| "A31" | (1S,2R)-N-(8-m-Tolyl-pyrido[4,3-d]pyrimidin-2-yl)-cyclohexane-1,2-diamine |
| "A32" | (R)-4-Methyl-2-(8-m-tolyl-pyrido[4,3-d]pyrimidin-2-ylamino)-pentanoic acid amide |
| "A33" | (1S,2R)-N-[8-(4,5,6,7-Tetrahydro-pyrazolo[1,5-a]pyridin-2-yl)-pyrido[4,3-d]pyrimidin-2-yl]-cyclohexane-1,2-diamine |
| "A34" | 6-[2-((1R,2S)-2-Amino-cyclohexylamino)-pyrido[4,3-d]pyrimidin-8-yl]-2,2-dimethyl-4H-benzo[1,4]oxazin-3-one |
| "A35" | (1S,2R)-N-[8-(3-Methoxy-phenylethynyl)-pyrido[4,3-d]pyrimidin-2-yl]-cyclohexane-1,2-diamine |
| "A36" | (1S,2R)-N-[8-(1H-Benzoimidazol-5-yl)-pyrido[4,3-d]pyrimidin-2-yl]-cyclohexane-1,2-diamine |
| "A37" | 5-[2-((1R,2S)-2-Amino-cyclohexylamino)-pyrido[4,3-d]pyrimidin-8-yl]-1,3-dihydro-benzimidazol-2-one |
| "A38" | (1S,2R)-N-[8-(1,2,3,6-Tetrahydro-pyridin-4-yl)-pyrido[4,3-d]-pyrimidin-2-yl]-cyclohexane-1,2-diamine |
| "A39" | (1S,2R)-N-[8-(3,6-Dihydro-2H-pyran-4-yl)-pyrido[4,3-d]pyrimidin-2-yl]-cyclohexane-1,2-diamine |
| "A40" | (1S,2R)-N-[8-(6-Methoxy-1H-indol-3-yl)-pyrido[4,3-d]pyrimidin-2-yl]-cyclohexane-1,2-diamine |
| "A41" | (1S,2R)-N-[8-(6-Trifluoromethyl-1H-indol-3-yl)-pyrido[4,3-d]-pyrimidin-2-yl]-cyclohexane-1,2-diamine |
| "A42" | (1S,2R)-N-[8-(6-Fluoro-1H-indol-2-yl)-pyrido[4,3-d]pyrimidin-2-yl]-cyclohexane-1,2-diamine |
| "A43" | (1S,2R)-N-[8-(6,7-Dihydro-4H-pyrazolo[5,1-c][1,4]oxazin-2-yl)-pyrido[4,3-d]pyrimidin-2-yl]-cyclohexane-1,2-diamine |
| "A44" | 3-[2-((1R,2S)-2-Amino-cyclohexylamino)-pyrido[4,3-d]pyrimidin-8-yl]-1H-indole-5-carbonitrile |
| "A45" | 3-[2-((1R,2S)-2-Amino-cyclohexylamino)-pyrido[4,3-d]pyrimidin-8-yl]-1H-indole-6-carbonitrile |
| "A46" | (1S,2R)-N-[8-(5-Fluoro-1H-indol-3-yl)-pyrido[4,3-d]pyrimidin-2-yl]-cyclohexane-1,2-diamine |
| "A47" | (1S,2R)-N-[8-(6-Fluoro-1H-indol-3-yl)-pyrido[4,3-d]pyrimidin-2-yl]-cyclohexane-1,2-diamine |
| "A48" | (R)-N1-[8-(1H-Indol-3-yl)-pyrido[4,3-d]pyrimidin-2-yl]-3-methoxy-propane-1,2-diamine |
| "A49" | cis-N3-[8-[6-(trifluoromethyl)-1H-indol-3-yl]pyrido[4,3-d]-pyrimidin-2-yl]tetrahydropyran-3,4-diamine |
| "A50" | cis-N4-[8-[6-(trifluoromethyl)-1H-indol-3-yl]pyrido[4,3-d]-pyrimidin-2-yl]tetrahydropyran-3,4-diamine |
| "A51" | cis-3,3-Difluoro-N1-[8-[6-(trifluoromethyl)-1H-indol-3-yl]pyrido[4,3-d]pyrimidin-2-yl]cyclohexane-1,2-diamine |
| "A52" | cis-3-Fluoro-N1-[8-[6-(trifluoromethyl)-1H-indol-3-yl]pyrido-[4,3-d]pyrimidin-2-yl]cyclohexane-1,2-diamine |
| "A53" | cis-4,4-Difluoro-N1-[8-[6-(trifluoromethyl)-1H-indol-3-yl]pyrido[4,3-d]pyrimidin-2-yl]cyclohexane-1,2-diamine |
| "A54" | cis-4-Fluoro-N1-[8-[6-(trifluoromethyl)-1H-indol-3-yl]pyrido-[4,3-d]pyrimidin-2-yl]cyclohexane-1,2-diamine |
| "A55" | cis-4,4-Difluoro-N2-[8-[6-(trifluoromethyl)-1H-indol-3-yl]pyrido[4,3-d]pyrimidin-2-yl]cyclohexane-1,2-diamine |
| "A56" | cis-4-Fluoro-N2-[8-[6-(trifluoromethyl)-1H-indol-3-yl]pyrido-[4,3-d]pyrimidin-2-yl]cyclohexane-1,2-diamine |
| "A57" | (1S,2S)-3,3-Difluoro-N2-[8-[6-(trifluoromethyl)-1H-indol-3-yl]pyrido[4,3-d]pyrimidin-2-yl]cyclohexane-1,2-diamine |

-continued

| Nr. | name |
|---|---|
| "A58" | cis-3-Fluoro-N2-[8-[6-(trifluoromethyl)-1H-indol-3-yl]pyrido[4,3-d]pyrimidin-2-yl]cyclohexane-1,2-diamine |
| "A59" | cis-2-[[8-[6-(Trifluoromethyl)-1H-indol-3-yl]pyrido[4,3-d]-pyrimidin-2-yl]amino]cyclohexanol |
| "A60" | 3,3,3-Trifluoro-N1-[8-[6-(trifluoromethyl)-1H-indol-3-yl]pyrido[4,3-d]pyrimidin-2-yl]propane-1,2-diamine |
| "A61" | (2R)-3-Methoxy-N1-[8-[6-(trifluoromethyl)-1H-indol-3-yl]-pyrido[4,3-d]pyrimidin-2-yl]propane-1,2-diamine |
| "A62" | (2R)-4-Methyl-2-[[8-[6-(trifluoromethyl)-1H-indol-3-yl]pyrido[4,3-d]pyrimidin-2-yl]amino]pentanamide |
| "A63" | cis-N2-[8-(7-Fluoro-1H-indol-3-yl)pyrido[4,3-d]pyrimidin-2-yl]cyclohexane-1,2-diamine |
| "A64" | N2-[8-[7-(Trifluoromethyl)-1H-indol-3-yl]pyrido[4,3-d]pyrimidin-2-yl]cyclohexane-1,2-diamine |
| "A65" | (R)-2-[8-[(6-Cyano-1H-indol-3-yl)-pyrido[4,3-d]pyrimidin-2-yl-amino]-4-methyl-pentanoic acid amide |
| "A66" | (1S,2R)-N-[8-(4-Methyl-1H-indol-2-yl)-pyrido[4,3-d]pyrimidin-2-yl]-cyclohexane-1,2-diamine |
| "A67" | 3-[2-((R)-2-Amino-3-methoxy-propylamino)-pyrido[4,3-d]-pyrimidin-8-yl]-1H-indole-6-carbonitrile |
| "A68" | (3R,4R)-N4-[8-(1H-Indol-3-yl)-pyrido[4,3-d]pyrimidin-2-yl]-tetrahydro-pyran-3,4-diamine |
| "A69" | 3-[2-((3R,4R)-3-Amino-tetrahydro-pyran-4-ylamino)-pyrido[4,3-d]pyrimidin-8-yl]-1H-indole-6-carbonitrile |
| "A70", "A71" | (cis)-2-[8-(1-benzenesulfonyl-1H-indol-3-yl)-pyrido-[4,3-d]pyrimidin-2-ylamino]-cyclohexanol |
| "A72" | 3-[2-((1R,2S)-2-amino-cyclohexylamino)-pyrido[4,3-d]pyrimidin-8-yl]-1H-indole-7-carbonitrile |
| "A73", "A74" | 3-[2-((cis)-2-hydroxy-cyclohexylamino)-pyrido[4,3-d]pyrimidin-8-yl]-1H-indole-6-carbonitrile |
| "A75" | 3-[2-((S)-5,5-difluoro-piperidin-3-ylamino)-pyrido[4,3-d]pyrimidin-8-yl]-1H-indole-6-carbonitrile |
| "A76" | (1S,2R)-N-[8-(1H-pyrrolo[2,3-c]pyridin-3-yl)-pyrido[4,3-d]pyrimidin-2-yl]-cyclohexane-1,2-diamine |
| "A77" | 3-[2-((1R,2S)-2-amino-cyclohexylamino)-pyrido[4,3-d]pyrimidin-8-yl]-1H-indole-6-carboxylic acid amide |
| "A78", "A79" | (3-fluoro-piperidin-3-ylmethyl)-[8-(6-trifluoromethyl-1H-indol-3-yl)-pyrido[4,3-d]pyrimidin-2-yl]-amine |
| "A80" | 3-(2-cyclohexylamino-pyrido[4,3-d]pyrimidin-8-yl)-1H-indole-6-carbonitrile |
| "A81" | (1S,2R)-N-[8-(7-fluoro-1H-indol-2-yl)-pyrido[4,3-d]pyrimidin-2-yl]-cyclohexane-1,2-diamine |
| "A82" | (1S,2R)-N-[5-difluoromethyl-8-(6-trifluoromethyl-1H-indol-3-yl)-pyrido[4,3-d]pyrimidin-2-yl]-cyclohexane-1,2-diamine |
| "A83" | 3-[2-(2-amino-3,3,3-trifluoro-propylamino)-pyrido[4,3-d]pyrimidin-8-yl]-1H-indole-6-carbonitrile |
| "A85" | 3-[2-((cis)-2-amino-cyclohexylamino)-5-methyl-pyrido[4,3-d]-pyrimidin-8-yl]-1H-indole-6-carbonitrile |
| "A86" | 2-((cis)-2-amino-cyclohexylamino)-8-(6-trifluoromethyl-1H-indol-3-yl)-6H-pyrido[4,3-d]pyrimidin-5-one |
| "A87" | 3-[2-((1R,2S)-2-amino-cyclohexylamino)-5-difluoromethyl-pyrido[4,3-d]pyrimidin-8-yl]-1H-indole-6-carbonitrile |
| "A88" | (1S,2R)-N-[5-methyl-8-(6-trifluoromethyl-1H-indol-3-yl)-pyrido[4,3-d]pyrimidin-2-yl]-cyclohexane-1,2-diamine |
| "A89" | (1R,2S)-N-[5-methyl-8-(6-trifluoromethyl-1H-indol-3-yl)-pyrido[4,3-d]pyrimidin-2-yl]-cyclohexane-1,2-diamine |
| "A90" | 2-((1S,2R)-2-amino-cyclohexylamino)-8-(1-methyl-1H-pyrazol-4-yl)-6H-pyrido[4,3-d]pyrimidin-5-one |
| "A91" | (1R,2S)-N-[5-difluoromethyl-8-(1-methyl-1H-pyrazol-4-yl)-pyrido-[4,3-d]pyrimidin-2-yl]-cyclohexane-1,2-diamine | and pharmaceutically acceptable solvates, salts, enantiomers, tautomers and stereoisomers thereof.

7. Process for the preparation of compounds of the formula I according to claim 1 and pharmaceutically acceptable salts, solvates, enantiomers, tautomers and stereoisomers thereof, comprising:

a) for the preparation of compounds of the formula I, wherein

R denotes NR⁴R⁴' and

R² denotes NR³Cyc, NR³CHR³CON(R³)₂, NR³[C(R³)₂]ₚCR³(NH₂)CH₂OA or NR³[C(R³)₂]ₚN(R³)₂, reacting a compound of the formula II

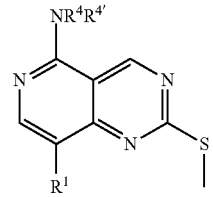

in which R¹, R⁴, R⁴' have the meanings indicated in claim 1, with a compound of the formula III

R²—NHR³    III in which R² and R³ have the meanings indicated in claim 1, or b) for the preparation of compounds of the formula I, wherein R denotes H, reacting a compound of the formula IV

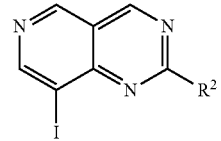

in which R² has the meanings indicated in claim 1, with a compound of the formula V

R¹-L    V in which R¹ has the meaning indicated in claim 1, and L denotes a boronic acid or a boronic acid ester group, in a Suzuki-type coupling, and/or converting a base or acid of the formula I into one of its salts.

8. A medicament composition comprising at least one compound of the formula I and/or pharmaceutically acceptable salts, solvates, enantiomers, tautomers and stereoisomers thereof, including mixtures thereof in all ratios, and optionally an pharmaceutically acceptable carrier, excipient or vehicle.

9. A medicaments composition comprising at least one compound of the formula I and/or pharmaceutically acceptable salts, solvates, enantiomers, tautomers and stereoisomers thereof, including mixtures thereof in all ratios, and at least one further medicament active ingredient.

10. A kit consisting of separate packs of
(a) an effective amount of a compound of the formula I and/or pharmaceutically acceptable salts, solvates, enantiomers, tautomers and stereoisomers thereof, including mixtures thereof in all ratios,
and
(b) an effective amount of a further medicament active ingredient.

11. A compound which is:

| "A86" | 2-((cis)-2-amino-cyclohexylamino)-8-(6-trifluoromethyl-1H-indol-3-yl)-6H-pyrido[4,3-d]pyrimidin-5-one |
|---|---|
| "A90" | 2-((1S,2R)-2-amino-cyclohexylamino)-8-(1-methyl-1H-pyrazol-4-yl)-6H-pyrido[4,3-d]pyrimidin-5-one | or a pharmaceutically acceptable salt, solvate, enantiomer, tautomer or stereoisomer thereof.

* * * * *